US010138507B2

(12) United States Patent
Bancel et al.

(10) Patent No.: US 10,138,507 B2
(45) Date of Patent: Nov. 27, 2018

(54) MANUFACTURING METHODS FOR PRODUCTION OF RNA TRANSCRIPTS

(71) Applicant: ModernaTX, Inc., Cambridge, MA (US)

(72) Inventors: Stephane Bancel, Cambridge, MA (US); William Joseph Issa, Roslindale, MA (US); John Grant Aunins, Cambridge, MA (US); Tirtha Chakraborty, Medford, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 14/777,190

(22) PCT Filed: Mar. 13, 2014

(86) PCT No.: PCT/US2014/026835
§ 371 (c)(1),
(2) Date: Sep. 15, 2015

(87) PCT Pub. No.: WO2014/152027
PCT Pub. Date: Sep. 25, 2014

(65) Prior Publication Data
US 2016/0024547 A1 Jan. 28, 2016

Related U.S. Application Data

(60) Provisional application No. 61/800,049, filed on Mar. 15, 2013.

(51) Int. Cl.
*C12P 19/34* (2006.01)
*C12Q 1/68* (2018.01)
*C12N 15/10* (2006.01)
*C12Q 1/6865* (2018.01)

(52) U.S. Cl.
CPC ............ *C12P 19/34* (2013.01); *C12N 15/101* (2013.01); *C12Q 1/6865* (2013.01)

(58) Field of Classification Search
None
See application file for complete search history.

(56) References Cited

U.S. PATENT DOCUMENTS 354,491 A 12/1886 Steinle
4,699,717 A 10/1987 Riesner et al.
5,057,426 A 10/1991 Henco et al.
5,338,448 A 8/1994 Gjerde
5,426,180 A 6/1995 Kool
5,489,677 A 2/1996 Sanghvi et al.
5,512,439 A 4/1996 Hornes et al.
5,591,722 A 1/1997 Montgomery et al.
5,599,667 A 2/1997 Arnold, Jr. et al.
5,637,459 A 6/1997 Burke et al.
5,639,873 A 6/1997 Barascut et al.
5,789,578 A 8/1998 Burton et al.
5,808,039 A 9/1998 Reddy et al.
5,989,911 A 11/1999 Fournier et al.
6,011,148 A 1/2000 Bussey et al.
6,022,715 A 2/2000 Merenkova et al.
6,022,737 A 2/2000 Niven et al.
6,248,268 B1 6/2001 Cook
6,303,378 B1 10/2001 Bridenbaugh et al.
6,391,542 B1 5/2002 Anderson et al.
6,423,492 B1 7/2002 Harbron
6,511,832 B1 1/2003 Guarino et al.
6,642,374 B2 11/2003 Gjerde et al.
6,812,341 B1 11/2004 Conrad
6,881,314 B1 4/2005 Wang et al.
7,691,569 B2 4/2010 Wohlgemuth et al.
8,075,780 B2 † 12/2011 Pearce
8,093,367 B2 1/2012 Kore et al.
8,664,194 B2 3/2014 de Fougerolles et al.
8,680,069 B2 3/2014 de Fougerolles et al.
8,710,200 B2 4/2014 Schrum et al.
8,716,465 B2 5/2014 Rossi et al.
8,802,438 B2 8/2014 Rossi et al.
8,822,663 B2 9/2014 Schrum et al.
8,883,506 B2 11/2014 Rossi et al.
8,898,864 B1 12/2014 Porter
8,980,864 B2 3/2015 Hoge et al.
8,999,380 B2 4/2015 Bancel et al.
9,050,297 B2 6/2015 Chakraborty et al.
9,061,059 B2 6/2015 Chakraborty et al.
9,089,604 B2 7/2015 Chakraborty et al.
9,095,552 B2 8/2015 Chakraborty et al.
(Continued)

FOREIGN PATENT DOCUMENTS

CA 2028849 A1 9/1991
CA 2473135 A1 6/2003
(Continued)

OTHER PUBLICATIONS

Weill et al., Nature Structural and Mol. Biol., 19, 6, 577-585, 2012.*
Extended European Search Report for European Application No. 14769839.3, dated Oct. 18, 2016 (10 pages).
Pascolo, Chapter 3: Vaccination With Messenger RNA. *Methods in Molecular Medicine*, vol. 127: *DNA Vaccines: Methods and Protocols: Second Edition.* Saltzman et al., Humana Press Inc., 23-40 (2006).
Vomelova et al., "Methods of RNA purification. All ways (should) lead to Rome," Folia Biol (Praha) 55(6):243-51 (2009).
Weiss et al., "Prophylactic mRNA vaccination against allergy," Curr Opin Allergy Clin Immunol. 10(6):567-74 (2010).
(Continued)

*Primary Examiner* — Nancy A Treptow
(74) *Attorney, Agent, or Firm* — Clark & Elbing LLP

(57) ABSTRACT

Described are methods for production of RNA transcripts using a non-amplified, linearized DNA template in an in vitro transcription reaction. Enzymatic 5' capping and oligo dT purification can also be included in the methods.

9 Claims, 11 Drawing Sheets

Specification includes a Sequence Listing.

(56) References Cited

U.S. PATENT DOCUMENTS

| | | | |
|---|---|---|---|
| 9,107,886 | B2 | 8/2015 | Chakraborty et al. |
| 9,114,113 | B2 | 8/2015 | Chakraborty et al. |
| 9,149,506 | B2 | 10/2015 | Chakraborty et al. |
| 9,428,535 | B2 | 8/2016 | de Fougerolles et al. |
| 9,533,047 | B2 | 1/2017 | de Fougerolles et al. |
| 9,675,668 | B2 | 6/2017 | Bancel et al. |
| 9,803,177 | B2 | 10/2017 | Rossi et al. |
| 2001/0025097 | A1 | 9/2001 | Sheridan et al. |
| 2002/0001812 | A1 | 1/2002 | Smith et al. |
| 2002/0016450 | A1 | 2/2002 | Laugharn et al. |
| 2002/0058256 | A1 | 5/2002 | Rothberg et al. |
| 2002/0114784 | A1 | 8/2002 | Li et al. |
| 2002/0130430 | A1 | 9/2002 | Castor |
| 2002/0153312 | A1 | 10/2002 | Gjerde et al. |
| 2003/0120035 | A1 | 6/2003 | Gao et al. |
| 2003/0120065 | A1 | 6/2003 | Froehler et al. |
| 2003/0170810 | A1 | 9/2003 | Vedadi et al. |
| 2003/0170876 | A1 | 9/2003 | Widner et al. |
| 2003/0170891 | A1 | 9/2003 | McSwiggen |
| 2003/0180754 | A1 | 9/2003 | Bergholtz et al. |
| 2003/0180779 | A1 | 9/2003 | Lofton-Day et al. |
| 2004/0038278 | A1 | 2/2004 | Tzertzinis et al. |
| 2004/0076978 | A1 | 4/2004 | Verfaillie |
| 2004/0142433 | A1 | 7/2004 | Padgett et al. |
| 2004/0220127 | A1 | 11/2004 | Sternberg et al. |
| 2004/0224425 | A1 | 11/2004 | Gjerde et al. |
| 2004/0259097 | A1 | 12/2004 | De Backer et al. |
| 2005/0003496 | A1 | 1/2005 | McGall et al. |
| 2005/0053942 | A1 | 3/2005 | Kauppinen et al. |
| 2005/0130196 | A1 | 6/2005 | Hofstadler et al. |
| 2006/0003371 | A1 | 1/2006 | Russell et al. |
| 2006/0058266 | A1 | 3/2006 | Manoharan et al. |
| 2006/0121441 | A1 | 6/2006 | Spira |
| 2006/0223081 | A1 | 10/2006 | Jarrell et al. |
| 2007/0020678 | A1 | 1/2007 | Ault-Riche et al. |
| 2007/0037148 | A1 | 2/2007 | Fong et al. |
| 2007/0037770 | A1 | 2/2007 | Gryaznov et al. |
| 2007/0244062 | A1 | 10/2007 | Laux et al. |
| 2007/0281336 | A1 | 12/2007 | Jendrisak et al. |
| 2008/0076910 | A1 | 3/2008 | Takkellapati et al. |
| 2008/0139801 | A1 | 6/2008 | Umansky et al. |
| 2008/0153078 | A1 | 6/2008 | Braman et al. |
| 2008/0171711 | A1 | 7/2008 | Hoerr et al. |
| 2008/0274463 | A1 | 11/2008 | Chen et al. |
| 2008/0311140 | A1 | 12/2008 | Lee et al. |
| 2009/0099041 | A1 | 4/2009 | Church et al. |
| 2009/0192303 | A1 | 7/2009 | Skagestad |
| 2009/0215125 | A1 | 8/2009 | Reed et al. |
| 2009/0264511 | A1 | 10/2009 | de Fougerolles et al. |
| 2009/0270278 | A1 | 10/2009 | Lim et al. |
| 2009/0286852 | A1 | 11/2009 | Kariko et al. |
| 2010/0015232 | A1 | 1/2010 | Besenbacher et al. |
| 2010/0047261 | A1 | 2/2010 | Hoerr et al. |
| 2010/0048883 | A1 | 2/2010 | Ketterer et al. |
| 2010/0178272 | A1 | 7/2010 | Hartmann et al. |
| 2010/0183639 | A1 | 7/2010 | Uhlmann et al. |
| 2010/0261231 | A1 | 10/2010 | Kore et al. |
| 2010/0317532 | A1 | 12/2010 | Liu et al. |
| 2011/0143397 | A1 | 6/2011 | Kariko et al. |
| 2011/0218170 | A1 | 9/2011 | Thottassery et al. |
| 2011/0244026 | A1 | 10/2011 | Guild et al. |
| 2011/0294205 | A1 | 12/2011 | Hukari et al. |
| 2011/0319506 | A1 | 12/2011 | Erbacher et al. |
| 2012/0046346 | A1 | 2/2012 | Rossi et al. |
| 2012/0100136 | A1 | 4/2012 | Patel et al. |
| 2012/0129261 | A1 | 5/2012 | Eberwine et al. |
| 2012/0140097 | A1 | 6/2012 | Morita et al. |
| 2012/0251618 | A1 | 10/2012 | Schrum et al. |
| 2013/0046084 | A1 | 2/2013 | Brown et al. |
| 2013/0052721 | A1 | 2/2013 | Hollander et al. |
| 2013/0058894 | A1 | 3/2013 | Maldonado et al. |
| 2013/0115272 | A1 | 5/2013 | de Fougerolles et al. |
| 2013/0123481 | A1 | 5/2013 | de Fougerolles et al. |
| 2013/0156849 | A1 | 6/2013 | de Fougerolles et al. |
| 2013/0165504 | A1 | 6/2013 | Bancel et al. |
| 2013/0197068 | A1 | 8/2013 | Kariko et al. |
| 2013/0203115 | A1 | 8/2013 | Schrum et al. |
| 2013/0244282 | A1 | 9/2013 | Schrum et al. |
| 2013/0245103 | A1 | 9/2013 | de Fougerolles et al. |
| 2013/0245106 | A1 | 9/2013 | de Fougerolles et al. |
| 2013/0251618 | A1 | 9/2013 | Li et al. |
| 2013/0259923 | A1 | 10/2013 | Bancel et al. |
| 2013/0259924 | A1 | 10/2013 | Bancel et al. |
| 2014/0010861 | A1 | 1/2014 | Bancel et al. |
| 2014/0105964 | A1 | 4/2014 | Bancel et al. |
| 2014/0105966 | A1 | 4/2014 | Bancel et al. |
| 2014/0147454 | A1 | 5/2014 | Chakraborty et al. |
| 2014/0200261 | A1 | 7/2014 | Hoge et al. |
| 2014/0206752 | A1 | 7/2014 | Afeyan et al. |
| 2014/0206852 | A1 | 7/2014 | Hoge et al. |
| 2014/0241956 | A1 | 8/2014 | Page et al. |
| 2014/0243399 | A1 | 8/2014 | Schrum et al. |
| 2014/0273230 | A1 | 9/2014 | Chen et al. |
| 2014/0275227 | A1 | 9/2014 | Hoge et al. |
| 2014/0343129 | A1 | 11/2014 | de Fougerolles et al. |
| 2014/0371302 | A1 | 12/2014 | Afeyan et al. |
| 2015/0005372 | A1 | 1/2015 | Hoge et al. |
| 2015/0017211 | A1 | 1/2015 | de Fougerolles et al. |
| 2015/0030576 | A1 | 1/2015 | Bancel |
| 2015/0044758 | A1 | 2/2015 | Amshey et al. |
| 2015/0050354 | A1 | 2/2015 | Bouchon et al. |
| 2015/0051268 | A1 | 2/2015 | Bancel et al. |
| 2015/0056253 | A1 | 2/2015 | Bancel et al. |
| 2015/0064235 | A1 | 3/2015 | Bancel et al. |
| 2015/0064236 | A1 | 3/2015 | Bancel et al. |
| 2015/0064725 | A1 | 3/2015 | Schrum et al. |
| 2015/0086614 | A1 | 3/2015 | Bancel et al. |
| 2015/0105275 | A1 | 4/2015 | Wong et al. |
| 2015/0111248 | A1 | 4/2015 | Bancel et al. |
| 2015/0141269 | A1 | 5/2015 | Soldatov et al. |
| 2015/0141499 | A1 | 5/2015 | Bancel et al. |
| 2015/0157781 | A1 | 6/2015 | Kyle et al. |
| 2015/0166616 | A1 | 6/2015 | Bancel et al. |
| 2015/0167017 | A1 | 6/2015 | Roy et al. |
| 2015/0211039 | A1 | 7/2015 | Wang et al. |
| 2015/0307542 | A1 | 10/2015 | Roy et al. |
| 2016/0017313 | A1 | 1/2016 | Spivak et al. |
| 2016/0024140 | A1 | 1/2016 | Issa et al. |
| 2016/0024141 | A1 | 1/2016 | Issa et al. |
| 2016/0024492 | A1 | 1/2016 | Issa et al. |
| 2016/0024547 | A1 | 1/2016 | Bancel et al. |
| 2016/0025630 | A1 | 1/2016 | Jensen et al. |
| 2016/0032273 | A1 | 2/2016 | Shahrokh et al. |
| 2016/0038612 | A1 | 2/2016 | Hoge et al. |
| 2016/0040154 | A1* | 2/2016 | Heartlein ........... C12N 15/1017 536/23.1 |
| 2016/0151516 | A1 | 6/2016 | Bancel et al. |
| 2016/0177295 | A1 | 6/2016 | Rudolph et al. |
| 2016/0194368 | A1 | 7/2016 | Hoge et al. |
| 2016/0194625 | A1 | 7/2016 | Hoge et al. |
| 2016/0237108 | A1 | 8/2016 | Fraley et al. |
| 2016/0244742 | A1 | 8/2016 | Linnarsson et al. |
| 2016/0326575 | A1 | 11/2016 | Von Der Mulbe et al. |
| 2016/0354490 | A1 | 12/2016 | Roy et al. |
| 2016/0354491 | A1 | 12/2016 | Roy et al. |
| 2016/0354492 | A1 | 12/2016 | Roy et al. |
| 2016/0354493 | A1 | 12/2016 | Roy et al. |
| 2017/0136131 | A1 | 5/2017 | Roy et al. |
| 2017/0136132 | A1 | 5/2017 | Roy et al. |
| 2017/0175129 | A1 | 6/2017 | Roy et al. |

FOREIGN PATENT DOCUMENTS

| | | | |
|---|---|---|---|
| EP | 0366400 | A2 | 5/1990 |
| EP | 1083232 | B1 | 2/2005 |
| EP | 1619254 | A1 | 1/2006 |
| EP | 1383556 | B9 | 3/2008 |
| EP | 2092064 | B1 | 9/2010 |
| EP | 2377938 | A1 | 10/2011 |
| EP | 2484770 | A1 | 8/2012 |
| EP | 2188379 | B1 | 1/2013 |
| EP | 2548960 | A1 | 1/2013 |
| JP | 2008-509168 | A | 3/2008 |
| JP | 2011-130725 | A | 7/2011 |

(56) References Cited

FOREIGN PATENT DOCUMENTS

| | | | |
|---|---|---|---|
| RU | 2540017 | C2 | 1/2015 |
| WO | WO-91/05058 | A1 | 4/1991 |
| WO | WO-93/03052 | A1 | 2/1993 |
| WO | WO-93/13121 | A1 | 7/1993 |
| WO | WO-97/07825 | A1 | 3/1997 |
| WO | 1998005673 | A1 † | 2/1998 |
| WO | WO-01/55306 | A2 | 8/2001 |
| WO | WO-01/81566 | A2 | 11/2001 |
| WO | WO-02/44399 | A2 | 6/2002 |
| WO | WO-03/039523 | A2 | 5/2003 |
| WO | WO-03/051881 | A1 | 6/2003 |
| WO | WO-2004/020575 | A2 | 3/2004 |
| WO | WO-2004/064782 | A2 | 8/2004 |
| WO | WO-2005/042716 | A2 | 5/2005 |
| WO | WO-2005/058933 | A1 | 6/2005 |
| WO | WO-2006/015445 | A1 | 2/2006 |
| WO | WO-2007/024708 | A2 | 3/2007 |
| WO | WO-2007/089607 | A2 | 8/2007 |
| WO | WO-2007/120863 | A2 | 10/2007 |
| WO | WO-2008/039669 | A1 | 4/2008 |
| WO | WO-2008/045505 | A2 | 4/2008 |
| WO | WO-2008/083949 | A2 | 7/2008 |
| WO | WO-2008/120016 | A1 | 10/2008 |
| WO | WO-2009/016431 | A1 | 2/2009 |
| WO | WO-2009/042971 | A2 | 4/2009 |
| WO | WO-2009/051451 | A2 | 4/2009 |
| WO | WO-2009/127060 | A1 | 10/2009 |
| WO | WO-2009/127230 | A1 | 10/2009 |
| WO | WO-2009/147519 | A1 | 12/2009 |
| WO | WO-2009/149253 | A2 | 12/2009 |
| WO | WO-2010/017510 | A1 | 2/2010 |
| WO | WO-2010/109289 | A1 | 9/2010 |
| WO | WO-2011/005850 | A1 | 1/2011 |
| WO | WO-2011/012316 | A2 | 2/2011 |
| WO | WO-2011/068810 | A1 | 6/2011 |
| WO | WO-2011/071931 | A2 | 6/2011 |
| WO | WO-2011/127933 | A1 | 10/2011 |
| WO | WO-2011/130624 | A2 | 10/2011 |
| WO | WO-2011/133868 | A2 | 10/2011 |
| WO | WO-2012/019168 | A2 | 2/2012 |
| WO | 2012077080 | A1 † | 6/2012 |
| WO | WO-2012/135805 | A2 | 10/2012 |
| WO | WO-2012/138530 | A1 | 10/2012 |
| WO | WO-2012/158736 | A1 | 11/2012 |
| WO | WO-2012/164565 | A1 | 12/2012 |
| WO | WO-2013/039857 | A1 | 3/2013 |
| WO | WO-2013/039861 | A2 | 3/2013 |
| WO | WO-2013/045434 | A1 | 4/2013 |
| WO | WO-2013/052523 | A1 | 4/2013 |
| WO | WO-2013/090186 | A1 | 6/2013 |
| WO | WO-2013/090294 | A1 | 6/2013 |
| WO | WO-2013/090648 | A1 | 6/2013 |
| WO | WO-2013/090897 | A1 | 6/2013 |
| WO | WO-2013/096709 | A2 | 6/2013 |
| WO | WO-2013/101690 | A1 | 7/2013 |
| WO | WO-2013/113326 | A1 | 8/2013 |
| WO | WO-2013/113501 | A1 | 8/2013 |
| WO | WO-2013/113502 | A1 | 8/2013 |
| WO | WO-2013/130161 | A1 | 9/2013 |
| WO | WO-2013/151663 | A1 | 10/2013 |
| WO | WO-2013/151664 | A1 | 10/2013 |
| WO | WO-2013/151665 | A2 | 10/2013 |
| WO | WO-2013/151666 | A2 | 10/2013 |
| WO | WO-2013/151667 | A1 | 10/2013 |
| WO | WO-2013/151668 | A2 | 10/2013 |
| WO | WO-2013/151669 | A1 | 10/2013 |
| WO | WO-2013/151670 | A2 | 10/2013 |
| WO | WO-2013/151671 | A1 | 10/2013 |
| WO | WO-2013/151672 | A2 | 10/2013 |
| WO | WO-2013/151736 | A2 | 10/2013 |
| WO | WO-2013/184976 | A2 | 12/2013 |
| WO | WO-2014/028429 | A2 | 2/2014 |
| WO | WO-2014/081507 | A1 | 5/2014 |
| WO | WO-2014/093574 | A1 | 6/2014 |
| WO | WO-2014/093924 | A1 | 6/2014 |
| WO | WO-2014/113089 | A2 | 7/2014 |
| WO | WO-2014/144039 | A1 | 9/2014 |
| WO | WO-2014/144711 | A1 | 9/2014 |
| WO | WO-2014/144767 | A1 | 9/2014 |
| WO | WO-2014/152027 | A1 | 9/2014 |
| WO | WO-2014/152030 | A1 | 9/2014 |
| WO | WO-2014/152211 | A1 | 9/2014 |
| WO | WO-2014/152513 | A1 | 9/2014 |
| WO | WO-2014/152540 | A1 | 9/2014 |
| WO | WO-2014/152659 | A1 | 9/2014 |
| WO | WO-2014/152673 | A1 | 9/2014 |
| WO | WO-2014/164253 | A1 | 10/2014 |
| WO | WO-2015/006747 | A2 | 1/2015 |
| WO | WO-2015/034925 | A1 | 3/2015 |
| WO | WO-2015/034928 | A1 | 3/2015 |
| WO | WO-2015/038892 | A1 | 3/2015 |
| WO | WO-2015/048744 | A2 | 4/2015 |
| WO | WO-2015/051169 | A2 | 4/2015 |
| WO | WO-2015/051173 | A2 | 4/2015 |
| WO | WO-2015/051214 | A1 | 4/2015 |
| WO | WO-2015/058069 | A1 | 4/2015 |
| WO | WO-2015/070413 | A1 | 5/2015 |
| WO | WO-2015/085318 | A2 | 6/2015 |
| WO | WO-2015/089511 | A2 | 6/2015 |
| WO | WO-2015/101416 | A1 | 7/2015 |
| WO | WO-2015/105926 | A1 | 7/2015 |
| WO | WO-2015/179598 | A2 | 11/2015 |
| WO | WO-2015/196118 | A1 | 12/2015 |
| WO | WO-2015/196128 | A2 | 12/2015 |
| WO | WO-2015/196130 | A2 | 12/2015 |
| WO | WO-2016/011222 | A2 | 1/2016 |
| WO | WO-2016/011226 | A1 | 1/2016 |
| WO | WO-2016/034620 | A1 | 3/2016 |
| WO | WO-2016/036902 | A1 | 3/2016 |
| WO | WO-2016/118724 | A1 | 7/2016 |
| WO | WO-2016/118725 | A1 | 7/2016 |

OTHER PUBLICATIONS

International Search Report and Written Opinion for International Application No. PCT/US12/58519, dated Feb. 28, 2013 (11 pages).

Karikó et al., "Incorporation of pseudouridine into mRNA yields superior nonimmunogenic vector with increased translational capacity and biological stability." Mol Ther. 16(11):1833-40 (2008).

Kore et al., "Synthesis and application of 2'-fluoro-substituted cap analogs." Bioorg Med Chem Letters. 17:5295-9 (2007).

Kormann et al., "Expression of therapeutic proteins after delivery of chemically modified mRNA in mice," Nat Biotechnol. 29(2):154-7 (2011) (6 pages).

Mestas et al., "Of mice and not men: differences between mouse and human immunology," J Immunol. 172(5):2731-8 (2004).

Partial European Search Report for European Patent Application No. 12838676.0, dated Jul. 9, 2015 (7 pages).

Tavernier et al., "mRNA as gene therapeutic: how to control protein expression," J Control Release. 150(3):238-47 (2011).

Warren et al., "Highly efficient reprogramming to pluripotency and directed differentiation of human cells with synthetic modified mRNA," Cell Stem Cell. 7(5):618-30 (2010).

Karikó et al., "mRNA is an endogenous ligand for Toll-like receptor 3," J Biol Chem. 279(13): 12542-50 (2004).

International Preliminary Report on Patentability for International Patent Application No. PCT/US2012/058519, dated Apr. 8, 2014 (8 pages).

International Preliminary Report on Patentability for International Patent Application No. PCT/US2013/075177, dated Jun. 16, 2015 (9 pages).

Grosjean, Modification and editing of RNA: historical overview and important facts to remember. *Fine-Tuning of RNA Functions by Modification and Editing*. Grosjean H, 1-22 (2005).

Extended European Search Report for European Application No. 13863642.8, dated Apr. 6, 2016 (6 pages).

PubChem Compound Summary for CID 262692, created Mar. 26, 2005. <URL: http://pubchem.ncbi.nlm.nih.gov/compound/262692> (11 pages).

(56) References Cited

OTHER PUBLICATIONS

PubChem Compound Summary for CID 479886, created Aug. 1, 2005. <URL: http://pubchem.ncbi.nlm.nih.gov/compound/479886> (12 pages).
Hikishima et al., "Synthesis of 1,8-naphthyridine C-nucleosides and their base-pairing properties in oligodeoxynucleotides: thermally stable naphthyridine:imidazopyridopyrimidine base-pairing motifs," Angew Chem Int Ed. 44:596-8 (2005).
"CRISPR RNA maturation by trans-encoded small RNA and host factor RNase III," available in PMC Sep. 30, 2011, published in final edited form as: Nature 471(7340):602-7 (2011) (54 pages).
Derrigo et al., "RNA-protein interactions in the control of stability and localization of messenger RNA (review)," Int J Mol Med. 5(2):111-23 (2000).
Gaj et al., "ZFN, TALEN, and CRISPR/Cas-based methods for genome engineering," Trends Biotechnol. 31(7):397-405 (2013).
Gilbert et al., "CRISPR-mediated modular RNA-guided regulation of transcription in eukaryotes," Cell 154(2):442-51 (2013) (15 pages).
Maeder et al., "CRISPR RNA-guided activation of endogenous human genes," Nat Methods 10(10):977-9 (2013).
Perez-Pinera et al., "RNA-guided gene activation by CRISPR-Cas9-based transcription factors," Nat Methods 10(10):973-6 (2013).
Wang et al., "One-step generation of mice carrying mutations in multiple genes by CRISPR/Cas-mediated genome engineering," Cell 153(4):910-8 (2013).
International Preliminary Report on Patentability and Written Opinion for International Patent Application No. PCT/US2014/026835, dated Sep. 15, 2015 (8 pages).
International Search Report for International Patent Application No. PCT/US2014/026835, dated Aug. 28, 2014 (4 pages).
"Potato spindle tuber viroid," Wikipedia, <https://en.wikipedia.org/wiki/Potato_spindle_tuber_viroid>, accessed Jan. 19, 2017 (2 pages).
Farrow et al., "Combinatorial recombination of gene fragments to construct a library of chimeras," Curr Protoc Protein Sci. Chapter 26, Unit 26.2 (2010) (20 pages).
Hansen et al., "Circular RNA and miR-7 in Cancer," Cancer Res. 73(18):5609-12 (2013).
Hansen et al., "Natural RNA circles function as efficient microRNA sponges," Nature. 495(7441):384-8 (2013) (7 pages).
Kanwar et al., "Chimeric aptamers in cancer cell-targeted drug delivery," Crit Rev Biochem Mol Bio. 46(6):459-77 (2011).
Kazantsev et al., "Crystal structure of a bacterial ribonuclease P RNA," Proc Natl Acad Sci U.S.A. 102(38):13392-7 (2005).
Kluiver et al., "Rapid generation of MicroRNA Sponges for MicroRNA Inhibition ," PLoS One. 7(1):E29275(2012) (8 pages).
Kuwahara et al., "Molecular evolution of functional nucleic acids with chemical modifications," Molecules. 15:5423-44 (2010).
Liu et al., "Construction of circular miRNA sponges targeting miR-21 or miR-221 and demonstration of their excellent anticancer effects on malignant melanoma cells," Int J Biochem Cell Biol. 45(11):2643-50 (2013).
Memczak et al., "Circular RNAs are a large class of animal RNAs with regulatory potency," Nature. 495(7441):333-8 (2013) (10 pages).
Qiu et al., "Creating a flexible multiple microRNA expression vector by linking precursor microRNAs," Biochem Biophys Res Commun. 411(2):276-80 (2011).
Salfen et al., "Effects of exogenous ghrelin on feed intake, weight gain, behavior, and endocrine responses in weanling pigs," J Anim Sci. 82(7):1957-66 (2004).
Wilusz et al., "Molecular Biology. A circuitous route to noncoding RNA," Science. 340(6131):440-1 (2013).
Yanagawa et al., "Overexpression of autocrine motility factor in metastatic tumor cells: possible association with augmented expression of KIF3A and GDI-beta," Lab Invest. 84(4):513-22 (2004).
Jeck et al., "Circular RNAs are abundant, conserved, and associated with ALU repeats," RNA 19(2):141-57 (2013) (19 pages).
Minuth et al., "A nucleobase analogue that pairs strongly with adenine," Angew Chem Int Ed Engl. 52(41):10874-7 (2013).
Irier et al., "Translational regulation of GluR2 mRNAs in rat hippocampus by alternative 3' untranslated regions," available in PMC Aug. 17, 2009, published in final edited form as: J Neurochem. 109(2):584-594 (2009) (18 pages).
Anderson et al., "Incorporation of pseudouridine into mRNA enhances translation by diminishing PKR activation," Nucleic Acids Res. 38(17):5884-92 (2010).
Anderson et al., "Nucleoside modifications in RNA limit activation of 2'-5'-oligoadenylate synthetase and increase resistance to cleavage by RNase L," Nucleic Acids Res. 39(21): 9329-38 (2011) (10 pages).
Andries et al., "N1-methylpseudouridine-incorporated mRNA outperforms pseudouridine-incorporated mRNA by providing enhanced protein expression and reduced immunogenicity in mammalian cell lines and mice," J Control Release. 217:337-44 (2015).
Azarani et al., "RNA analysis by ion-pair reversed-phase high performance liquid chromatography," Nucleic Acids Res. 29(2):E7 (2001) (9 pages).
Bangs et al., "Mass Spectrometry of mRNA cap 4 from trypanosomatids reveals two novel nucleosides," J Biol Chem. 267(14):9805-15 (1992).
Bellon et al., "4'-Thio-oligo-beta-D-ribonucleotides: synthesis of beta-4'-thio-oligouridylates, nuclease resistance, base pairing properties, and interaction with HIV-1 reverse transcriptase," Nucleic Acids Res. 21(7):1587-93 (1993).
Bellon et al., "Sugar modified oligonucleotides: synthesis, nuclease resistance and base pairing of oligodeoxynucleotides containing 1-(4'-thio-beta-D-ribofuranosyl)-thymine," Biochem Biophys Res Commun. 184(2):797-803 (1992).
Berensmeier, "Magnetic particles for the separation and purification of nucleic acids," Appl Microbiol Biotechnol. 73:495-504 (2006).
Bhaduri et al., "Procedure for the preparation of milligram quantities of adenovirus messenger ribonucleic acid," J Virol. 10(6):1126-9 (1972).
Bynum et al., "Characterization of subcellular poly(A) RNA populations by poly(U) sepharose chromatography and discontinuous elution," Anal Biochem. 107(2):406-16 (1980).
Carmody et al., Purity and Content Analysis of Oligonucleotides by Capillary Gel Electrophoresis. Handbook of Analysis of Oligonucleotides and Related Products. Bonilla and Srivatsa, 243-264, retrieved from <http://www.nbchem.de/mediapool/120/1202675/data/K11050_C007.pdf> on Jul. 18, 2014 (2011).
Chen et al., "LC/MS analysis of cellular RNA reveals NAD-linked RNA," Nat Chem Biol. 5(12):879-81 (2009).
Chien et al., "RNA:DNA hybrids are more stable than DNA:DNA duplexes in concentrated perchlorate and trichloroacetate solutions," Nucleic Acids Res. 5(5):1627-37 (1978).
Colpan et al., "Large-scale purification of viroid RNA using Cs2SO4 gradient centrifugation and high-performance liquid chromatography," Anal Biochem. 131(1):257-65 (1983).
Communication pursuant to Article 94(3) EPC for European Application No. 14769839.3, dated Mar. 28, 2018 (5 pages).
Crain, "Preparation and enzymatic hydrolysis of DNA and RNA for mass spectrometry," Methods Enzymol. 193:782-90 (1990).
Cross et al., "Analysis of small nuclear ribonucleoproteins (RNPs) in Trypanosoma brucei: structural organization and protein components of the spliced leader RNP," Mol Cell Biol. 11(11):5516-5526 (1991).
Dickman "Ion Pair Reverse-Phase Chromatography: A Versatile Platform for the Analysis of RNA" <http://www.chromatographytoday.com/articles/prep-chiral-green-incsfc-gpc-ion/33/m._j._dickman/ion_pair_reverse-phase_chromatography_a_versatile_platform_for_the_analysis_of_rna/984/> retrieved on Oct. 16, 2015 (5 pages).
Farrell, Related Techniques. RNA Methodologies: A Laboratory Guide for Isolation and Characterization. Third Edition. p. 475 (2005) (6 pages).
Fath et al., "Multiparameter RNA and codon optimization: a standardized tool to assess and enhance autologous mammalian gene expression," PLoS One 6(3):e17596 (2011) (14 pages).
Gjerde et al. RNA Purification and Analysis: Sample Preparation, Extraction, Chromatography, <http://onlinelibrary.wiley.com/book/10.1002/9783527627196> retrieved on Jul. 18, 2014 (203 pages).

(56) References Cited

OTHER PUBLICATIONS

Haeberli et al., "Syntheses of 4'-thioribonucleosides and thermodynamic stability and crystal structure of RNA oligomers with incorporated 4'-thiocytosine," Nucleic Acids Res. 33(13):3965-75 (2005).
Hamaguchi et al., "Direct reverse transcription-PCR on oligo(dT)-immobilized polypropylene microplates after capturing total mRNA from crude cell lysates," Clin Chem. 44(11):2256-63 (1998).
Trier et al., "Translational regulation of GluR2 mRNAs in rat hippocampus by alternative 3' untranslated regions," available in PMC Aug. 17, 2009, published in final edited form as: J Neurochem. 109(2):584-594 (2009) (18 pages).
Jakobsen et al., "Direct mRNA Isolation Using Magnetic Oligo (dT) Beads: A Protocol for All Types of Cell Cultures, Animal and Plant Tissues," Advances in Biomagnetic Separation. ed. Uhlén et al., Eaton Publishing, 61-71 (1994) (15 pages).
Jakobsen et al., "Purification of mRNA directly from crude plant tissues in 15 minutes using magnetic oligo dT microspheres," Nucleic Acids Res. 18(12):3669 (1990).
Jani et al., "In vitro transcription and capping of Gaussia luciferase mRNA followed by HeLa cell transfection," J Vis Exp. 61:e3702 (2012) (9 pages).
Karikó et al., "Suppression of RNA recognition by Toll-like receptors: the impact of nucleoside modification and the evolutionary origin of RNA," Immunity. 23(2):165-75 (2005).
Kim et al. "Rapid purification of RNAs using fast performance liquid chromatography (FPLC)." RNA. 13(2):289-94 (2007).
Kumar et al., "Template-directed oligonucleotide strand ligation, covalent intramolecular DNA circularization and catenation using click chemistry," J Am Chem Soc. 129(21):6859-64 (2007).
Kuwahara et al., "Molecular evolution of functional nucleic acids with chemical modifications," Molecules. 15(8):5423-44 (2010).
Lapham et al., "RNase H cleavage for processing of in vitro transcribed RNA for NMR studies and RNA ligation," RNA. 2(3):289-96 (1996).
Liu et al., "In vitro transcription on DNA templates immobilized to streptavidin MagneSphere(r) paramagnetic particles," Promega Notes 64:21 (1997) (6 pages).
McCarthy et al. "Reversed-phase ion-pair liquid chromatography analysis and purification of small interfering RNA" Anal Biochem. 390(2):181-8 (2009).
McKenna et al. "Purification and characterization of transcribed RNAs using gel filtration chromatography." Nat Protoc. 2(12):3270-7 (2007).
Melton et al., "Efficient in vitro synthesis of biologically active RNA and RNA hybridization probes from plasmids containing a bacteriophage SP6 promoter," Nucleic Acids Res. 12(18):7035-56 (1984).
Mitra, "Using analytical ultracentrifugation (AUC) to measure global conformational changes accompanying equilibrium tertiary folding of RNA molecules," Methods in Enzymology, 2009(469):209-36 (2009).
Mészáros et al., "Subtractive hybridization strategy using paramagnetic oligo(dT) beads and PCR," Biotechniques 20(3):413-9 (1996).
Olesiak et al., "The synthesis of di- and oligo-nucleotides containing a phosphorodithioate internucleotide linkage with one of the sulfur atoms in a 5'-bridging position," Org Biomol Chem. 7(10):2162-9 (2009).
Pardi et al., "Expression kinetics of nucleoside-modified mRNA delivered in lipid nanoparticles to mice by various routes," available in PMC Nov. 10, 2016, published in final edited form as: J Control Release. 217:345-51 (2015) (18 pages).
Park et al., "Reverse transcriptase-coupled quantitative real time PCR analysis of cell-free transcription on the chromatin-assembled p21 promoter," PLoS One 6(8):e23617 (2011) (6 pages).

Pomerantz et al., "Analysis of RNA hydrolyzates by liquid chromatography-mass spectrometry," Methods Enzymol. 193:796-824 (1990).
Reyes-Engel et al., "Direct quantification of specific mRNA using a selected biotinylated oligonucleotide by free solution capillary electrophoresis," Nucleic Acids Res. 21(3):759-60 (1993).
Safarik et al., "Large-scale separation of magnetic bioaffinity adsorbents," Biotechnology Letters. 23:1953-6 (2001).
Sasaki et al., "Construction of a normalized cDNA library by introduction of a semi-solid mRNA-cDNA hybridization system," Nucleic Acids Res. 22(6):987-92 (1994).
Shimelis et al., "Nuclease P1 digestion/high-performance liquid chromatography, a practical method for DNA quantitation," J Chromatogr A. 1117(2):132-6 (2006).
Slater, Chapter 16: The Purification of Poly(A)-Containing RNA by Affinity Chromatography. Methods in Molecular Biology. ed. Walker, Springer Verlag,117-20 (1985).
Smith et al., "Purification of polynucleotide phosphorylase by affinity chromatography and some properties of the purified enzymes," Nucleic Acids Res. 1(12):1763-73 (1974).
St. Claire, "Positive ion electrospray ionization tandem mass spectrometry coupled to ion-pairing high-performance liquid chromatography with a phosphate buffer for the quantitative analysis of intracellular nucleotides," Rapid Commun Mass Spectrom. 14(17):1625-34 (2000).
Theus et al., "A simple assay for determining the capping efficiencies of RNA polymerases used for in vitro transcription," Biotechniques. 9(5):610-2, 614-5 (1990).
Valadi et al., "Exosome-mediated transfer of mRNAs and microRNAs is a novel mechanism of genetic exchange between cells," Nat Cell Biol. 9(6):654-9 (2007) (17 pages).
Vera et al., "Combination of in vitro capping and ribonuclease protection improves the detection of transcription start sites in chloroplasts," Plant Mol Biol. 19(2):309-11 (1992).
Wang et al., "Characterization of mutation spectra with ultra-deep pyrosequencing: application to HIV-1 drug resistance," Genome Res. 17(8):1195-201 (2007).
Xu, "Tutorial: Capillary Electrophoresis," The Chemical Educator. 1(2): 1-14 (1996) (14 pages), retrieved from <http://web.colby.edu/ch332public/files/2012/02/CE_tutorial.pdf> on Jul. 18, 2014.
Yamamoto et al., "Current prospects for mRNA gene delivery," Eur J Pharm Biopharm. 71(3):484-9 (2009).
Nielsen et al., "An mRNA is capped by a 2',5' lariat catalyzed by a group I-like ribozyme," Science. 309(5740):1584-7 (2005).
Moretti et al., "Mechanism of translational regulation by miR-2 from sites in the 5' untranslated region or the open reading frame," RNA. 16(12):2493-502 (2010).
Henke et al., "microRNA-122 stimulates translation of hepatitis C virus RNA," EMBO J. 27(24):3300-10 (2008).
Stocher ands Berg, "Removal of template DNA from cRNA preparations by combined oligo (dT) affinity chromatography and DNase I digestion," Biotechniques, 36(3):480-482, 2004.†
Azarani and Hecker, "RNA analysis by ion-pair reversed-phase high performance liquid chromatography," Nucleic Acids Research, 29(2):e7, 2001.†
Lukavsky and Puglisi, "Large-scale preparation and purification of polyacrylyamide-free RNA oligonucleotides," RNA, 10:889-893, 2004.†
Jani and Fuchs, "In vitro transcription and capping of Gaussia luciferase mRNA followed by HeLa cell transfection," J. Vis. Exp. 61:e3702, 2012.†

\* cited by examiner
† cited by third party

Sequence

| | | | | | | | |
|---|---|---|---|---|---|---|---|
| 1 | GGTCTCCTAT | ACGTCTCTTA | TACGACATCA | CCGATGGGGA | ACCCAGACGC | TGAGTACGTA | TTCTAAATGC |
| 71 | ATAATAAATA | CTGATAACAT | CTTATAGTTT | GTATTATATT | TTGTATTATC | GTTGACATGT | ATAATTTTGA |
| 141 | TATCAAAAAC | TGATTTTCCC | TTTATTATTT | TCGAGATTTA | TTTTCTTAAT | TCTCTTTAAC | AAACTAGAAA |
| 211 | TATTGTATAT | ACAAAAAATC | ATAAATAATA | GATGAATAGT | TTAATTATAG | GTGTTCATCA | ATCGAAAAAG |
| 281 | CAACGTATCT | TATTTAAAGT | GCGTTGCTTT | TTTCTCATTT | ATAAGGTTAA | ATAATTCTCA | TATATCAAGC |
| 351 | AAAGTGACAG | GCGCCCTTAA | ATATTCTGAC | AAATGCTCTT | TCCCTAAACT | CCCCCCATAA | AAAAACCCGC |
| 421 | CGAAGCGGGT | TTTTACGTTA | TTTGCGGATT | AACGATTACT | CGTTATCAGA | ACCGCCCAGG | GGGCCCGAGC |
| 491 | TTAAGACTGG | CCGTCGTTTT | ACAACACAGA | AAGAGTTTGT | AGAAACGCAA | AAAGGCCATC | CGTCAGGGGC |
| 561 | CTTCTGCTTA | GTTTGATGCC | TGGCAGTTCC | CTACTCTCGC | CTTCCGCTTC | CTCGCTCACT | GACTCGCTGC |
| 631 | GCTCGGTCGT | TCGGCTGCGG | CGAGCGGTAT | CAGCTCACTC | AAAGGCGGTA | ATACGGTTAT | CCACAGAATC |
| 701 | AGGGGATAAC | GCAGGAAAGA | ACATGTGAGC | AAAAGGCCAG | CAAAAGGCCA | GGAACCGTAA | AAAGGCCGCG |
| 771 | TTGCTGGCGT | TTTTCCATAG | GCTCCGCCCC | CCTGACGAGC | ATCACAAAAA | TCGACGCTCA | AGTCAGAGGT |
| 841 | GGCGAAACCC | GACAGGACTA | TAAAGATACC | AGGCGTTTCC | CCCTGGAAGC | TCCCTCGTGC | GCTCTCCTGT |
| 911 | TCCGACCCTG | CCGCTTACCG | GATACCTGTC | CGCCTTTCTC | CCTTCGGGAA | GCGTGGCGCT | TTCTCATAGC |
| 981 | TCACGCTGTA | GGTATCTCAG | TTCGGTGTAG | GTCGTTCGCT | CCAAGCTGGG | CTGTGTGCAC | GAACCCCCCG |
| 1051 | TTCAGCCCGA | CCGCTGCGCC | TTATCCGGTA | ACTATCGTCT | TGAGTCCAAC | CCGGTAAGAC | ACGACTTATC |
| 1121 | GCCACTGGCA | GCAGCCACTG | GTAACAGGAT | TAGCAGAGCC | AGGTATGTAG | GCGGTGCTAC | AGAGTTCTTC |
| 1191 | AAGTGGTGGG | CTAACTACGG | CTACACTAGA | AGAACAGTAT | TTGGTATCTG | CGCTCTGCTG | AAGCCAGTTA |
| 1261 | CCTTCGGAAA | AAGAGTTGGT | AGCTCTTGAT | CCGGCAAACA | AACCACCGCT | GGTAGCGGTG | GTTTTTTTGT |
| 1331 | TTGCAAGCAG | CAGATTACGC | GCAGAAAAAA | AGGATCTCAA | GAAGATCCTT | TGATCTTTTC | TACGGGGTCT |
| 1401 | GACGCTCAGT | GGAACGACGC | GCGCGTAACT | CACGTTAAGG | GATTTTGGTC | ATGAGCTTGC | GCCGTCCCGT |
| 1471 | CAAGTCAGCG | TAATGCTCTG | CTTTTACCAA | TGCTTAATCA | GTGAGGCACC | TATCTCAGCG | ATCTGTCTAT |
| 1541 | TTCGTTCATC | CATAGTTGCC | TGACTCCCCG | TCGTGTAGAT | AACTACGATA | CGGGAGGGCT | TACCATCTGG |
| 1611 | CCCCAGCGCT | GCGATGATAC | CGCGAGAACC | ACGCTCACCG | GCTCCGGATT | TATCAGCAAT | AAACCAGCCA |
| 1681 | GCCGGAAGGG | CCGAGCGCAG | AAGTGGTCCT | GCAACTTTAT | CCGCCTCCAT | CCAGTCTATT | AATTGTTGCC |
| 1751 | GGAAGCTAG | AGTAAGTAGT | TCGCCAGTTA | ATAGTTTGCG | CAACGTTGTT | GCCATCGCTA | CAGGCATCGT |
| 1821 | GGTGTCACGC | TCGTCGTTTG | GTATGGCTTC | ATTCAGCTCC | GGTTCCCAAC | GATCAAGGCG | AGTTACATGA |
| 1891 | TCCCCCATGT | TGTGCAAAAA | AGCGGTTAGC | TCCTTCGGTC | CTCCGATCGT | TGTCAGAAGT | AAGTTGGCCG |
| 1961 | CAGTGTTATC | ACTCATGGTT | ATGGCAGCAC | TGCATAATTC | TCTTACTGTC | ATGCCATCCG | TAAGATGCTT |
| 2031 | TTCTGTGACT | GGTGAGTACT | CAACCAAGTC | ATTCTGAGAA | TAGTGTATGC | GGCGACCGAG | TTGCTCTTGC |
| 2101 | CCGGCGTCAA | TACGGGATAA | TACCGCGCCA | CATAGCAGAA | CTTTAAAAGT | GCTCATCATT | GGAAAACGTT |
| 2171 | CTTCGGGGCG | AAAACTCTCA | AGGATCTTAC | CGCTGTTGAG | ATCCAGTTCG | ATGTAACCCA | CTCGTGCACC |
| 2241 | CAACTGATCT | TCAGCATCTT | TTACTTTCAC | CAGCGTTTCT | GGGTGAGCAA | AAACAGGAAG | GCAAAATGCC |
| 2311 | GCAAAAAAGG | GAATAAGGGC | GACACGGAAA | TGTTGAATAC | TCATATTCTT | CCTTTTTCAA | TATTATTGAA |
| 2381 | GCATTTATCA | GGGTTATTGT | CTCATGAGCG | GATACATATT | TGAATGTATT | TAGAAAAATA | AACAAATAGG |
| 2451 | GGTCAGTGTT | ACAACCAATT | AACCAATTCT | GAACATTATC | GCGAGCCCAT | TTATACCTGA | ATATGGCTCA |
| 2521 | TAACACCCCT | TGTTTGCCTG | GCGGCAGTAG | CGCGGTGGTC | CCACCTGACC | CCATGCCGAA | CTCAGAAGTG |
| 2591 | AAACGCCGTA | GCGCCGATGG | TAGTGTGGGG | ACTCCCCATG | CGAGAGTAGG | GAACTGCCAG | GCATCAAATA |
| 2661 | AAACGAAAGG | CTCAGTCGAA | AGACTGGGCC | TTTCGCCCGG | CCTAATTAGG | GGGGCTGGAT | CGCTTCGTGT |
| 2731 | TCCCCATCGG | TGATGTCGTA | TAGGAAGCAG | TATACGAGAC | CTATAGGAGA | CGTATATGGT | CTTCTTTTCT |
| 2801 | AGATTTTTTT | TTTTTTTTTT | TTTTTTTTTT | TTTTTTTTTT | TTTTTTTTTT | TTTTTTTTTT | TTTTTTTTTT |
| 2871 | TTTTTTTTTT | TTTTTTTTTT | TTTTTTTTTT | TTTTTTTTTT | TTTTTTTTTT | TTTTTTTTTT | TTTTTTTTTT |
| 2941 | TTTTGCATGC | TCGAGCGGCC | GCCTTCCTAC | TCAGGCTTTA | TTCAAAGACC | AAGAGGTACA | GGTGCAAGGG |
| 3011 | AGAGAAGAAG | GGCATGGCCA | GAAGGCAAGC | CCCGCAGAAG | GCAGCTTATC | ACGGCTGCGC | AAGATGTCTC |
| 3081 | AGCACCCGGT | ACGAGACTTC | CAAAAATGAT | TGAAGGTGGC | TCGCTACGAG | GACTCCACCC | GCCCTGCGCT |
| 3151 | GAAACGCGGA | CGCAAAGGCC | GGCATTGCCC | CCTGCGTGGG | CTGCAGCGCG | GGTGCCATCC | CCAGTTCCTC |
| 3221 | CATCTGCTGC | CAGATGGTTG | TTGCGAAATC | CGCCACGTCG | AGCTGCAACG | TGTCCAGCGT | CGGGCCCAAT |
| 3291 | TCTGGCGAGA | TTCCCTCAAG | GGCTTGCACC | AGTCCCTGAT | ACAAGAACAA | ACCGGAGTGG | AGCTGGGAAA |
| 3361 | GGCACCCTGC | CAACTGCAAA | GCCTGCGACG | GACAGGACGA | GAGAGGAGCC | CAGGGAATCC | CCAAGCTGTT |
| 3431 | CCCGAGCAGT | ACGAGCTCCT | CGGGATGGCA | AAGTTTGTAT | GTCGCGCACA | GCTTCTCTTG | GAGTGCCCCT |
| 3501 | CCATCGCCCT | GAATCTTTCG | CACCTGCTCC | AGACACTTCA | AAAGGAATGA | CTGCGGCAAC | GATGAGGCAC |
| 3571 | GTCCGAGAGG | AGTCGCTTCT | TGGACTGTCC | AGAGGGCCGA | GTGCCAAAGC | AGCAACTGCA | GGGCCATAAG |
| 3641 | TTTCATGGGG | CTTTGGGTCG | CGGGACCGGC | CATGGTGGCT | CTTATATTTC | TTCTTACTCT | TCTTTTCTCT |
| 3711 | CTTATTTCCC | TATAGTGAGT | CGTATTAGCT | TCTGTACGAG | GGTCCAAAAG | CTTGACCCCC | AAGACACTAT |
| 3781 | A | | | | | | |

FIG. 6

Sequence

1 AAAAGATCAA AGGATCTTCT TGAGATCCTT TTTTTCTGCG CGTAATCTGC TGCTTGCAAA
61 CAAAAAAACC ACCGCTACCA GCGGTGGTTT GTTTGCCGGA TCAAGAGCTA CCAACTCTTT
121 TTCCGAAGGT AACTGGCTTC AGCAGAGCGC AGATACCAAA TACTGTTCTT CTAGTGTAGC
181 CGTAGTTAGC CCACCACTTC AAGAACTCTG TAGCACCGCC TACATACCTC GCTCTGCTAA
241 TCCTGTTACC AGTGGCTGCT GCCAGTGGCG ATAAGTCGTG TCTTACCGGG TTGGACTCAA
301 GACGATAGTT ACCGGATAAG GCGCAGCGGT CGGGCTGAAC GGGGGGTTCG TGCACACAGC
361 CCAGCTTGGA GCGAACGACC TACACCGAAC TGAGATACCT ACAGCGTGAG CTATGAGAAA
421 GCGCCACGCT TCCCGAAGGG AGAAAGGCGG ACAGGTATCC GGTAAGCGGC AGGGTCGGAA
481 CAGGAGAGCG CACGAGGGAG CTTCCAGGGG GAAACGCCTG GTATCTTTAT AGTCCTGTCG
541 GGTTTCGCCA CCTCTGACTT GAGCGTCGAT TTTTGTGATG CTCGTCAGGG GGGCGGAGCC
601 TATGGAAAAA CGCCAGCAAC GCGGCCTTTT TACGGTTCCT GGCCTTTTGC TGGCCTTTTG
661 CTCACATGTT CTTTCCTGCG TTATCCCCTG ATTCTGTGGA TAACCGTATT ACCGCCTTTG
721 AGTGAGCTGA TACCGCTCGC CGCAGCCGAA CGACCGAGCG CAGCGAGTCA GTGAGCGAGG
781 AAGCGGAAGG CGAGAGTAGG GAACTGCCAG GCATCAAACT AAGCAGAAGG CCCCTGACGG
841 ATGGCCTTTT TGCGTTTCTA CAAACTCTTT CTGTGTTGTA AAACGACGGC CAGTCTTAAG
901 CTCGGGCCCC CTGGGCGGTT CTGATAACGA GTAATCGTTA ATCCGCAAAT AACGTAAAAA
961 CCCGCTTCGG CGGGTTTTTT TATGGGGGGA GTTTAGGGAA AGAGCATTTG TCAGAATATT
1021 TAAGGGCGCC TGTCACTTTG CTTGATATAT GAGAATTATT TAACCTTATA AATGAGAAAA
1081 AAGCAACGCA CTTTAAATAA GATACGTTGC TTTTTCGATT GATGAACACC TATAATTAAA
1141 CTATTCATCT ATTATTTATG ATTTTTTGTA TATACAATAT TTCTAGTTTG TTAAAGAGAA
1201 TTAAGAAAAT AAATCTCGAA AATAATAAAG GGAAAATCAG TTTTTGATAT CAAAATTATA
1261 CATGTCAACG ATAATACAAA ATATAATACA AACTATAAGA TGTTATCAGT ATTTATTATG
1321 CATTTAGAAT AAATTTTGTG TCGCCCTTCG CTGAATCAAG CTTTTGGACC CTCGTACAGA
1381 AGCTAATACG ACTCACTATA GGGAAATAAG AGAGAAAAGA AGAGTAAGAA GAAATATAAG
1441 AGCCACCATG CAGCGCGTCA ACATGATTAT GGCCGAATCG CCGGGACTCA TCACAATCTG
1501 CCTCTTGGGT TATCTCTTGT CGGCAGAATG TACCGTGTTC TTGGATCACG AAAACGCGAA
1561 CAAAATTCTT AATCGCCCGA AGCGGTATAA CTCCGGGAAA CTTGAGGAGT TTGTGCAGGG
1621 CAATCTTGAA CGAGAGTGCA TGGAGGAGAA ATGCTCCTTT GAGGAGGCGA GGGAAGTGTT
1681 TGAAAACACA GAGCGAACAA CGGAGTTTTG GAAGCAATAC GTAGATGGGG ACCAGTGTGA
1741 GTCGAATCCG TGCCTCAATG GGGGATCATG TAAAGATGAC ATCAATAGCT ATGAATGCTG
1801 GTGCCCGTTT GGGTTTGAAG GGAAGAACTG TGAGCTGGAT GTGACGTGCA ACATCAAAAA
1861 CGGACGCTGT GAGCAGTTTT GTAAGAACTC GGCTGACAAT AAGGTAGTAT GCTCGTGCAC
1921 AGAGGGATAC CGGCTGGCGG AGAACCAAAA ATCGTGCGAG CCCGCAGTCC CGTTCCCTTG
1981 TGGGAGGGTG AGCGTGTCAC AGACTAGCAA GTTGACGAGA GCGGAGACTG TATTCCCCGA
2041 CGTGGACTAC GTCAACAGCA CCGAAGCCGA AACAATCCTC GATAACATCA CGCAGAGCAC
2101 TCAGTCCTTC AATGACTTTA CGAGGGTCGT AGGTGGTGAG GACGCGAAAC CCGGTCAGTT
2161 CCCCTGGCAG GTGGTATTGA ACGGAAAAGT CGATGCCTTT TGTGGAGGTT CCATTGTCAA
2221 CGAGAAGTGG ATTGTCACAG CGGCACACTG CGTAGAAACA GGAGTGAAAA TCACGGTAGT
2281 GGCGGGAGAG CATAACATTG AAGAGACAGA GCACACGGAA CAAAAGCGAA ATGTCATCAG
2341 AATCATTCCA CACCATAACT ATAACGCGGC AATCAATAAG TACAATCACG ACATCGCACT
2401 TTTGGAGCTT GACGAACCTT TGGTGCTTAA TTCGTACGTC ACCCCTATTT GTATTGCCGA
2461 CAAAGAGTAT ACAAACATCT TCTTGAAATT CGGCTCCGGG TACGTATCGG GCTGGGGCAG
2521 AGTGTTCCAT AAGGGTAGAT CCGCACTGGT GTTGCAATAC CTCAGGGTGC CCCTCGTGGA
2581 TCGAGCCACT TGTCTGCGGT CCACCAAATT CACAATCTAC AACAATATGT TCTGTGCGGG
2641 ATTCCATGAA GGTGGGAGAG ATAGCTGCCA GGGAGACTCA GGGGGTCCCC ACGTGACGGA
2701 AGTCGAGGGG ACGTCATTTC TGACGGGAAT TATCTCATGG GGAGAGGAAT GTGCGATGAA
2761 GGGGAAATAT GGCATCTACA CTAAAGTGTC ACGGTATGTC AATTGGATCA AGGAAAAGAC
2821 GAAACTCACG TGATAATAGG CTGGAGCCTC GGTGGCCATG CTTCTTGCCC CTTGGGCCTC
2881 CCCCCAGCCC CTCCTCCCCT TCCTGCACCC GTACCCCCGT GGTCTTTGAA TAAAGTCTGA
2941 GTGGGCGGCA AAAAAAAAAA AAAAAAAAAA AAAAAAAAAA AAAAAAAAAA AAAAAAAAAA
3001 AAAAAAAAAA AAAAAAAAAA AAAAAAAAAA AAAAAAAAAA AAAAAAAAAA AAAAAAAAAA
3061 AAAAAAAAAA AAAAAAAAAA AAAAAAAAAG AAGAGCCGTC AATCGAGTTC GTACCTAAGG
3121 GCGACACCCC ATAATTAGCC CGGGCGAAAG GCCCAGTCTT TCGACTGAGC CTTTCGTTTT
3181 ATTTGATGCC TGGCAGTTCC CTACTCTCGC ATGGGGAGTC CCCACACTAC CATCGGCGCT
3241 ACGGCGTTTC ACTTCTGAGT TCGGCATGGG GTCAGGTGGG ACCACCGCGC TACTGCCGCC
3301 AGGCAAACAA GGGGTGTTAT GAGCCATATT CAGGTATAAA TGGGCTCGCG ATAATGTTCA
3361 GAATTGGTTA ATTGGTTGTA ACACTGACCC CTATTTGTTT ATTTTTCTAA ATACATTCAA
3421 ATATGTATCC GCTCATGAGA CAATAACCCT GATAAATGCT TCAATAATAT TGAAAAAGGA
3481 AGAATATGAG TATTCAACAT TTCCGTGTCG CCCTTATTCC CTTTTTTGCG GCATTTTGCC
3541 TTCCTGTTTT TGCTCACCCA GAAACGCTGG TGAAAGTAAA AGATGCTGAA GATCAGTTGG
3601 GTGCACGAGT GGGTTACATC GAACTGGATC TCAACAGCGG TAAGATCCTT GAGAGTTTTC
3661 GCCCCGAAGA ACGTTTTCCA ATGATGAGCA CTTTTAAAGT TCTGCTATGT GGCGCGGTAT
3721 TATCCCGTAT TGACGCCGGG CAAGAGCAAC TCGGTCGCCG CATACACTAT TCTCAGAATG
3781 ACTTGGTTGA GTACTCACCA GTCACAGAAA AGCATCTTAC GGATGGCATG ACAGTAAGAG
3841 AATTATGCAG TGCTGCCATA ACCATGAGTG ATAACACTGC GGCCAACTTA CTTCTGACAA
3901 CGATCGGAGG ACCGAAGGAG CTAACCGCTT TTTTGCACAA CATGGGGGAT CATGTAACTC
3961 GCCTTGATCG TTGGGAACCG GAGCTGAATG AAGCCATACC AAACGACGAG CGTGACACCA
4021 CGATGCCTGT AGCGATGGCA ACAACGTTGC GCAAACTATT AACTGGCGAA CTACTTACTC
4081 TAGCTTCCCG GCAACAATTA ATAGACTGGA TGGAGGCGGA TAAAGTTGCA GGACCACTTC
4141 TGCGCTCGGC CCTTCCGGCT GGCTGGTTTA TTGCTGATAA ATCCGGAGCC GGTGAGCGTG
4201 GTTCTCGCGG TATCATCGCA GCGCTGGGGC CAGATGGTAA GCCCTCCCGT ATCGTAGTTA
4261 TCTACACGAC GGGGAGTCAG GCAACTATGG ATGAACGAAA TAGACAGATC GCTGAGATAG
4321 GTGCCTCACT GATTAAGCAT TGGTAAAAGC AGAGCATTAC GCTGACTTGA CGGGACGGCG
4381 CAAGCTCATG ACCAAAATCC CTTAACGTGA GTTACGCGCG CGTCGTTCCA CTGAGCGTCA
4441 GACCCCGTAG

FIG. 11B

MANUFACTURING METHODS FOR PRODUCTION OF RNA TRANSCRIPTS

CROSS REFERENCE TO RELATED APPLICATIONS

Not applicable.

REFERENCE TO A SEQUENCE LISTING

This application contains a Sequence Listing in computer readable form. The computer readable form is incorporated herein by reference.

STATEMENT REGARDING FEDERALLY SPONSORED RESEARCH OR DEVELOPMENT

Not applicable.

BACKGROUND OF THE INVENTION

Field of the Invention

The invention relates to methods useful for manufacture of RNA transcripts, e.g., mRNA.

Description of the Related Art

The manufacturing process used to produce clinical grade chemically modified mRNA therapeutics must be able to generate mRNA of high purity and potency, consistently, reproducibly, and in compliance with current good manufacturing practices (cGMP). The RNA must be as homogeneous as possible; this includes obtaining a uniform cap structure/5' terminus, correct sequence, correct poly A tail length and minimizing the formation of product related impurities.

To generate poly A tail containing mRNAs, several approaches have been taken utilizing in vitro transcription. The first is transcription using a "tailless" DNA template. A 3' Poly A tail is added, post-transcriptionally using a Poly A polymerase. Tails greater than 100 bases are typically generated. The downfall of this approach is the difficulty of controlling tail length and the evolution of tail length distribution in the RNA.

The use of PCR to generate DNA templates containing a Poly A:T tract is another approach. The poly A:T tracts are introduced via PCR primers, introducing another step for creation of impurities.

SUMMARY OF THE INVENTION

Disclosed is a method for production of an RNA transcript, e.g., mRNA, using a non-amplified, linearized DNA template in an in vitro transcription reaction to generate the RNA transcript. In some embodiments the RNA transcript is capped via enzymatic capping. The method results in production of homogeneous RNA transcripts with high purity and potency. In some embodiments the RNA transcript is purified via chromatographic methods, e.g., use of an oligo dT substrate. In one embodiment the method excludes the use of DNase.

BRIEF DESCRIPTION OF THE SEVERAL VIEWS OF THE DRAWINGS

FIG. 6 is a DNA sequence of plasmid pJ344:91543-TC-GCSF-pA-V1, according to one embodiment.

FIG. 11B is a DNA sequence of plasmid pJ204:109475-TC-FIX-Hs-3-pA140-Sap, according to one embodiment.

DETAILED DESCRIPTION OF THE INVENTION

Figure 1:
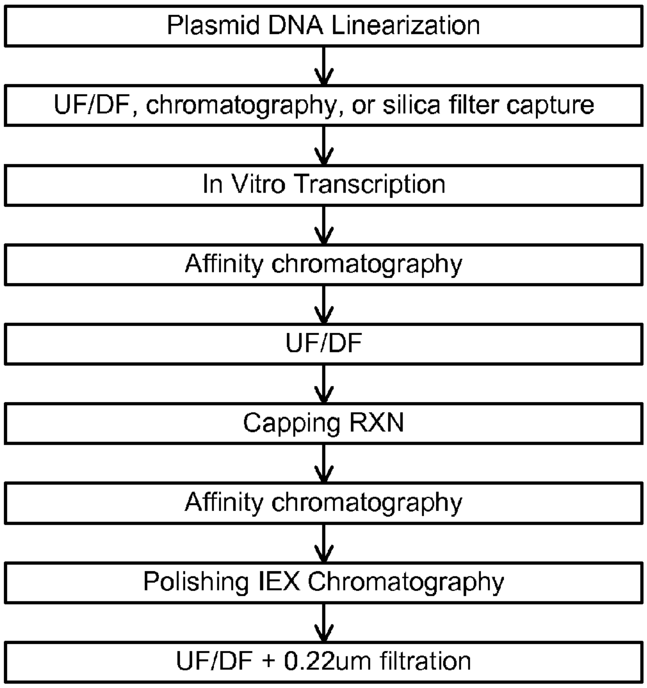
FIG. 1 is a flow chart of one embodiment of the method.

Disclosed are methods for production of RNA transcripts, e.g., mRNA, useful for producing clinical grade mRNA of high purity and potency, consistently, reproducibly, and in compliance with current good manufacturing practices (cGMP). The method uses a non-amplified, linearized DNA template in an in vitro transcription reaction to generate the RNA transcript. In some embodiments the RNA transcript is purified via oligo dT substrate without the use of DNase. Enzymatic capping is used for 5' capping of the RNA transcript.

PCR generated DNA templates have disadvantages that can be mitigated using linearized whole plasmid DNA templates A PCR-free process has the following advantages:

Scalability: Plasmid DNA template can be produced at microgram, milligram and gram scale in a cGMP compliant fashion. Large scale production of PCR generated templates is not commercially viable.

Higher purity mRNA transcripts than with PCR product templates: There is lower risk that no additional aberrant species are transcribed when using a linearized, non-amplified DNA template. Additionally, PCR amplification creates another intermediate in the manufacturing process where additional impurities may be introduced. When using PCR amplification, the gene of interest is amplified and typically does not contain a poly A tail. The poly A tail is introduced via the reverse primer, not encoded in the plasmid template. Utilizing linearized plasmid DNA template produces RNA transcripts of higher quality and purity Increased process efficiency: An additional unit operation (PCR) is removed from the process increasing throughput and reducing production time.

Whole plasmid allows for simple DNA/RNA separation: Use of whole plasmid DNA template is more amenable to SEC and IEX chromatographic separations compared to use of PCR product due to larger disparity in size and charge density between DNA and RNA. Whole plasmid can also be removed using a poly dT based affinity purification in the flowthrough fraction.

In addition, there are advantages to the methods use of enzymatic capping. For large scale manufacturing, 5' capping of RNA transcripts is typically performed using a chemical cap analog. This is performed co-transcriptionally where the cap analog: GTP molar ratio in the reaction is ~4:1. This typically results in ~80% capping efficiency, as well as reduced RNA transcript yields due to consumption of GTP. This high abundance of uncapped species is undesirable when developing therapeutic RNA. Since only capped mRNA is translated into protein, the presence of a high abundance of uncapped species (ie 20%) is problematic as efficacy (protein production/mg RNA) is reduced by 20% and 20% of the final drug substance is an inert impurity, decreasing process productivity.

The presence of uncapped species is also potentially immunogenic: Presence of a 5' triphosphate motif on uncapped RNAs can be potentially immunostimulatory (see Hornung et. al and Abbas et. al). Use of cap analogs requires additional phosphatase treatment to remove the 5'-triphosphate motif from the RNAs.

In contrast, the use of enzymatic capping for clinical grade mRNA production is a nearly quantitative capping process that is much more efficient than co-transcriptional capping using cap analogs. This increases potency, process productivity, as well as reduces the potential for immunogenicity.

Definitions

Terms used in the claims and specification are defined as set forth below unless otherwise specified.

Polynucleotide. The term "polynucleotide" is interchangeable with nucleic acid, and includes any compound and/or substance that comprise a polymer of nucleotides. RNA transcripts produced by the method of the invention and DNA templates used in the methods of the invention are polynucleotides. Exemplary polynucleotides include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

RNA transcript. As used herein, an "RNA transcript" refers to a ribonucleic acid produced by an in vitro transcription reaction using a DNA template and an RNA polymerase. As described in more detail below, an RNA transcript typically includes the coding sequence for a gene of interest and a poly A tail. RNA transcript includes an mRNA. The RNA transcript can include modifications, e.g., modified nucleotides. As used herein, the term RNA transcript includes and is interchangeable with mRNA, modified mRNA "mmRNA" or modified mRNA, and primary construct.

Gene of interest. As used herein, "gene of interest" refers to a polynucleotide which encodes a polypeptide or protein of interest. Depending on the context, the gene of interest refers to a deoxyribonucleic acid, e.g., a gene of interest in a DNA template which can be transcribed to an RNA transcript, or a ribonucleic acid, e.g., a gene of interest in an RNA transcript which can be translated to produce the encoded polypeptide of interest in vitro, in vivo, in situ or ex vivo. As described in more detail below, a polypeptide of interest includes but is not limited to, biologics, antibodies, vaccines, therapeutic proteins or peptides, etc.

DNA template. As used herein, a DNA template refers to a polynucleotide template for RNA polymerase. Typically a DNA template includes the sequence for a gene of interest operably linked to a RNA polymerase promoter sequence.

Operably linked: As used herein, the phrase "operably linked" refers to a functional connection between two or more molecules, constructs, transcripts, entities, moieties or the like. For example, a gene of interest operably linked to an RNA polymerase promoter allows transcription of the gene of interest.

Poly A tail. As used herein, "poly A tail" refers to a chain of adenine nucleotides. The term can refer to poly A tail that is to be added to an RNA transcript, or can refer to the poly A tail that already exists at the 3' end of an RNA transcript. As described in more detail below, a poly A tail is typically 5-300 nucleotides in length.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

It must be noted that, as used in the specification and the appended claims, the singular forms "a," "an" and "the" include plural referents unless the context clearly dictates otherwise.

Methods of the Invention

Disclosed is a method for production of an RNA transcript, e.g., mRNA, using a non-amplified, linearized DNA template in an in vitro transcription reaction to generate the RNA transcript. In some embodiments the RNA transcript is capped via enzymatic capping. The method results in production of homogeneous RNA transcripts with high purity and potency. In some embodiments the RNA transcript is purified via chromatographic methods, e.g., use of an oligo dT substrate. In one embodiment the method excludes the use of DNase.

In one embodiment, an RNA transcript is synthesized from a non-amplified, linear DNA template coding for the gene of interest via an enzymatic in vitro transcription reaction utilizing a T7 phage polymerase and nucleotide triphosphates of the desired chemistry. The RNA transcript is enzymatically capped post transcriptionally at the 5' end using Vaccinia guanylyltransferase, guanosine triphosphate and s-adenosyl-L-methionine to yield cap 0 structure, i.e., an inverted 7-methylguanosine cap is added via a 5' to 5' triphosphate bridge. Alternatively, use of an 2'O-methyltransferase with the Vaccinia guanylyltransferase yields a cap 1 structure where in addition to the cap 0 structure, the 2'OH group is methylated on the penultimate nucleotide. In some embodiments the RNA transcript is chromatographically purified during the manufacturing process using affinity and/or anion exchange methods and diafiltered into the appropriate formulation buffer. This process is PCR free.

DNA Templates

The method used a non amplified, linearized plasmid DNA as the template for in vitro transcription. Cells, e.g., bacterial cells, e.g., *E. coli*, e.g., DH-1 cells are transfected with the plasmid DNA template. The transfected cells are cultured to replicate the plasmid DNA which is then isolated and purified.

The plasmid DNA template includes a gene of interest coding for, e.g., a polypeptide of interest. A detailed description of genes of interest is found below. In one embodiment, the gene of interest is a GCSF (granular colony stimulating factor) gene. In another embodiment, the gene of interest codes is a Factor IX gene. In another embodiment the gene of interest is a EP (erythropoietin) gene.

The plasmid DNA template also includes a RNA polymerase promoter, e.g., a T7 promoter located 5' to and operably linked to the gene of interest. Also included is a sequence coding for a poly A tail located 3' to the gene of interest. Additional description of promoters and poly A tails is found below.

Figure 2:
FIG. 2 illustrates overhangs of linearized plasmid DNA template with different endonucleases, according to one embodiment.

Immediately downstream of the poly A tail coding sequence on the plasmid DNA template is a recognition site for a restriction endonuclease to linearize the plasmid. Linearization of the plasmid mitigates transcriptional readthrough. In one embodiment, the endonuclease produces a 5' overhang on the linearized DNA template. In another embodiment, the endonuclease produces a blunt end on the linearized DNA template. In another embodiment, the endonuclease produces 3' overhang on the linearized DNA template. Examples of endonucleases resulting in 5' overhangs include XbaI, SapI, NotI, EcoRI, HindIII, and SPEI. FIG. 2 shows examples of such overhangs. Examples of endonucleases resulting in blunt ends include SPE1. Additional endonucleases are well known to one of skill in the art and can be used depending on the application.

In one embodiment, XbaI is utilized as the restriction endonuclease with a recognition site of 5'TCTAGA3'. The five base overhang left on the DNA template sequence results in additional bases on the 3' end of the RNA transcript post-transcription. In other embodiments, the restriction endonuclease SAP I is used. The resulting overhang on the linearized DNA template sequence does not generate additional bases on the 3' end of the RNA transcript.

The plasmid into which the gene of interest, promoter, poly A tail sequence, and 5' and 3' UTR, and linearization restriction sites are inserted can be, e.g., one knows to one of skill in the art. Examples include but are not limited to pUC57, pJ204 (from DNA 2.0) and pJ344 (from DNA 2.0).

Examples of DNA templates to be used in the methods of the invention include, e.g., pJ344:91543 (including a GCSF gene and XbaI site) and pJ204:109475 (including a Factor IX gene and a SAPI site). Both plasmids are described in detail below.

In some embodiments, following linearization, the plasmid DNA template is filtered into an appropriate solvent, e.g., water, TE (Tris-EDTA), 10 mM Tris HCl pH 7.5, HEPES/phosphate and the like. Filtration occurs via, e.g., ultrafiltration, diafiltration, or, e.g., tangential flow ultrafiltration/diafiltration.

The linearized DNA template can be purified before use as a template for in vitro transcription. For example, the linearized DNA template can be purified chromatographically, or purified using a silica filter based DNA capture method.

In Vitro Transcription

The linearized DNA template is used in an in vitro transcription (IVT) system. The system typically comprises a transcription buffer, nucleotide triphosphates (NTPs), an RNase inhibitor and an RNA polymerase. The NTPs may be manufactured in house, may be selected from a supplier, or may be synthesized as described herein. The NTPs may be selected from, but are not limited to, those described herein including natural and unnatural (modified) NTPs. Additional description of modified nucleotides is found below.

RNA Polymerases

Any number of RNA polymerases or variants may be used in the method of the present invention. The polymerase may be selected from, but is not limited to, a phage RNA polymerase, e.g., a T7 RNA polymerase, a T3 RNA polymerase, an SP6 RNa polymerase, and/or mutant polymerases such as, but not limited to, polymerases able to incorporate modified nucleic acids.

RNA polymerases may be modified by inserting or deleting amino acids of the RNA polymerase sequence. As a non-limiting example, the RNA polymerase may be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants may be obtained by evolving an RNA polymerase, optimizing the RNA polymerase amino acid and/or nucleic acid sequence and/or by using other methods known in the art. As a non-limiting example, T7 RNA polymerase variants may be evolved using the continuous directed evolution system set out by Esvelt et al. (Nature (2011) 472(7344):499-503; herein incorporated by reference in its entirety) where clones of T7 RNA polymerase may encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants may encode at least mutation as described in U.S. Pub. Nos. 20100120024 and 20070117112; herein incorporated by reference in their entireties. Variants of RNA polymerase may also include, but are not limited to, substitutional variants, conservative amino acid substitution, insertional variants, deletional variants and/or covalent derivatives.

In one embodiment, the RNA transcript may be designed to be recognized by the wild type or variant RNA polymerases. In doing so, the RNA transcript may be modified to contain sites or regions of sequence changes from the wild type or parent primary construct.

Transcription Reaction Conditions

Typical reaction conditions for in vitro transcription can be as follows. One of skill in the art understands that parameters can be changed according to the application, e.g., the polymerase and nucleotides used.

The in vitro transcription reaction includes the following: an RNA polymerase, e.g., a T7 RNA polymerase at a final concentration of, e.g., 1000-12000 U/mL, e.g., 7000 U/mL; the DNA template at a final concentration of, e.g., 10-70 nM, e.g., 40 nM; nucleotides (NTPs) at a final concentration of e.g., 0.5-10 nM, e.g., 7.5 nM each; magnesisum at a final concentration of, e.g., 12-60 mM, e.g., magnesium acetate at 40 mM; a buffer such as, e.g., HEPES or Tris at a pH of, e.g., 7-8.5, e.g. 40 mM Tris HCl, pH 8

In some embodiments 5 mM dithiothreitol (DTT) and/or 1 mM spermidine is included. In some embodiments, an RNase inhibitor is included in the in vitro transcription reaction to ensure no RNase induced degradation during the transcription reaction. For example, murine RNase inhibitor can be utilized at a final concentration of 1000 U/mL, In some embodiments a pyrophosphatase is included in the in vitro transcription reaction to cleave the inorganic pyrophosphate generated following each nucleotide incorporation into two units of inorganic phosphate. This ensures that magnesium, which is essential for transcription, remains in solution and does not precipitate as magnesium pyrophosphate. For example, an E. *Coli* inorganic pyrophosphatase can utilized at a final concentration of 1 U/mL.

The in vitro transcription reaction is allowed to proceed, for example, under constant mixing at 37° C. for 4 hours. Typical yields can be, e.g., 5 mg of RNA per mL of transcription reaction.

A typical in vitro transcription reaction might have the following properties:

| | Stock Concentration | | | | effective concentration | | |
|---|---|---|---|---|---|---|---|
| Lot # | | | | | | | |
| Template: | | | | | | | |
| Process: | | | | | | | |
| Duration/Temp: | | | | | | | |
| Projected Total RNA Yield | 30 mg | | | | | 20 uL/rxnP | |
| | | 300 RXns | **Enter | | | | |
| water | | 2170.1 uL | | | | | |
| DNA template | 1450 ng/uL | 379.9 uL | or | 550.8 ug | 40 nM | enter** | 91.8 ug/mL DNA |
| T7 Buffer | 10 X | 600.0 uL | | | 1 X | | |
| ATP (100 mM) | 100 mM | 450.0 uL | | | 7.5 mM | | 1.84 ug/rxn DNA template |
| GTP (100 mM) | 100 mM | 450.0 uL | | | 7.5 mM | | |
| CTP (100 mM) | 100 mM | 450.0 uL | | | 7.5 mM | | |
| UTP (100 mM) | 100 mM | 450.0 uL | | | 7.5 mM | | |
| RNase inhibitor | 40,000 U/mL | 150.0 uL | | | 1000 U/mL | | |
| T7 Polymerase | 50000 U/mL | 840.0 uL | | | 7000 U/mL | | |
| pyrophosphatase | 100 U/mL | 60.0 uL | | | 1 U/mL | | |
| Total Volume | | 6000 uL | | | | | |
| Conc of DNA template: | | 1450 ng/uL | | **Enter | | Do not use DNASe if using whole plasmid as a DNA template | |
| RNA yield projection | | 5 mg RNA/mL IVT | | | 30 mg | | 15.9 uM RNA in Solution |
| Length of RNA | | 922 bases | | **Enter | | | |
| RNA MW | | 313,480 Da | | | | | |
| DNA MW | | 2,295,067 Da | | | | | |
| Length of DNA Template | | 3,781 BPa | | For Plasmid: Enter length of whole Plasmid<br>For PCR: Enter length of PCR Product calculated below | | | |

Nucleotides

The In Vitro Transcription Reaction Includes Nucleotides (NTPs). The Nucleotides can be unmodified NTPs, e.g., A, C, C, and U ribonucleotides, or modified nucleotides, or a combination. A more detailed description of modified nucleotides is found below. Examples of nucleotide combinations useful for in vitro transcription are found in the table below.

Example combinations of nucleotides for in vitro transcription.

| Chemistry | A | G | ε | U |
|---|---|---|---|---|
| Gen 0 | ATP | GTP | CTP | UTP |
| Gen 1 | ATP | GTP | 5mCTP | ψTP |
| Gen 2 | ATP | GTP | 5mCTP | N-1-meψTP |
| Gen 3 | ATP | GTP | 5mCTP | 2-thio UTP |
| Gen 4 | ATP | GTP | CTP | ψTP |
| Gen 5 | ATP | GTP | CTP | N-1-meψTP |

Key:
ATP = Adenosine triphosphate;
GTP = Guanosine triphosphate;
CTP = Cytidine Triphosphate;
UTP = Uridine Triphosphate;
5mCTP = 5-methylcytidine triphosphate;
2-thio UTP = 2-thiouridine triphosphate;
ψTP = pseudouridine triphosphate;
N-1-meψTP =1-methylpseudouridine triphosphate.

Capping of RNA Transcripts

In some embodiments the RNA transcript is enzymatically capped at the 5/end after in vitro transcription. Capping can be performed either before or after further purification of the RNA transcript, e.g., oligo dT purification. If not performing purification prior to capping, an ultrafiltration/diafiltration step must be performed (e.g., buffer exchange).

Figure 3:
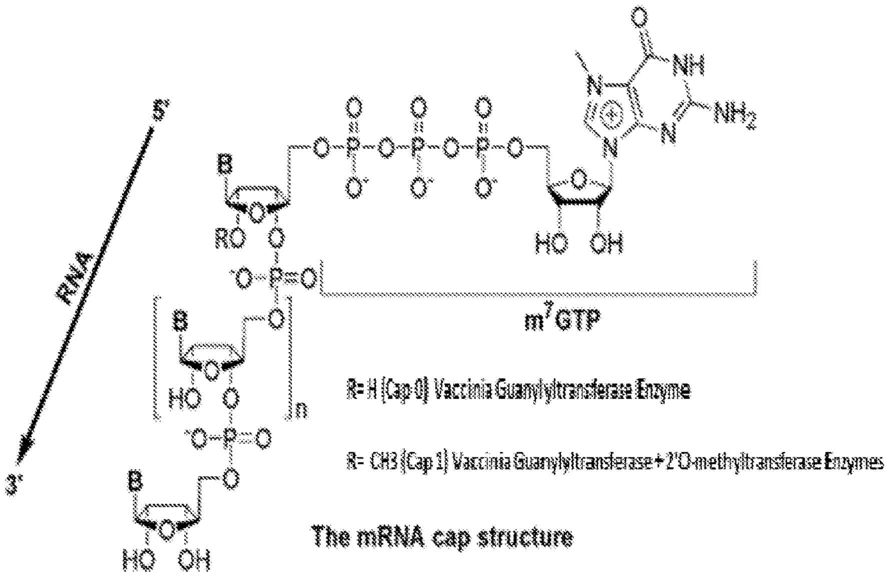
FIG. 3 illustrates an mRNA cap structure, according to one embodiment.

Non-limiting examples of 5' cap structures are those which, among other things, have enhanced binding of cap binding proteins, increased half life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of an mRNA and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N,pN2p (cap 0), 7mG(5')ppp(5')N1mpNp (cap 1), and 7mG(5')-ppp(5')N1mpN2mp (cap 2). An example of a cap structure is illustrated in FIG. 3.

For example, the RNA transcript can be enzymatically capped at the 5' end using Vaccinia guanylyltransferase, guanosine triphosphate and s-adenosyl-L-methionine to yield cap 0 structure. An inverted 7-methylguanosine cap is added via a 5' to 5' triphosphate bridge. Alternatively, use of a 2'O-methyltransferase with Vaccinia guanylyltransferase yields the cap 1 structure where in addition to the cap 0 structure, the 2'OH group is methylated on the penultimate nucleotide. S-adenosyl-L-methionine (SAM) is a cofactor utilized as a methyl transfer reagent.

In one embodiment enzymatic 5' capping is performed as follows. S-adenosylmethione chloride*2HCl is dissolved at 20 mM in 5 mM HCl 10/90 v/v % ethanol/water as a prepared stock. RNase inhibitor are utilized as a safeguard to ensure no RNase degradation is observed during the reaction. The final 1× buffer conditions consist of the following: 50 mM Tris HCl pH 8, 5 mM KCl, 1 mM MgCl2, and 1 mM dithiothreitol. The reaction is run under constant mixing at 37° C. for 2 hours. Enzymatic capping is of considerably higher efficiency than performing co-transcription through the use of dinucleotide cap analogs.

In another embodiment, the RNA transcript is co-transcriptional capped. The 5' terminal caps may include endogenous caps or cap analogs. A 5' terminal cap may comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

RNA Transcripts

An RNA transcript is the polynucleotide product of the in vitro transcription reaction. Typically the RNA transcript includes a gene of interest and a poly-A tail. In some embodiments, the RNA transcript includes a 5'UTR and a 3'UTR. In one embodiment the RNA transcript includes a 5' cap, typically added post transcriptionally.

Figure 4:
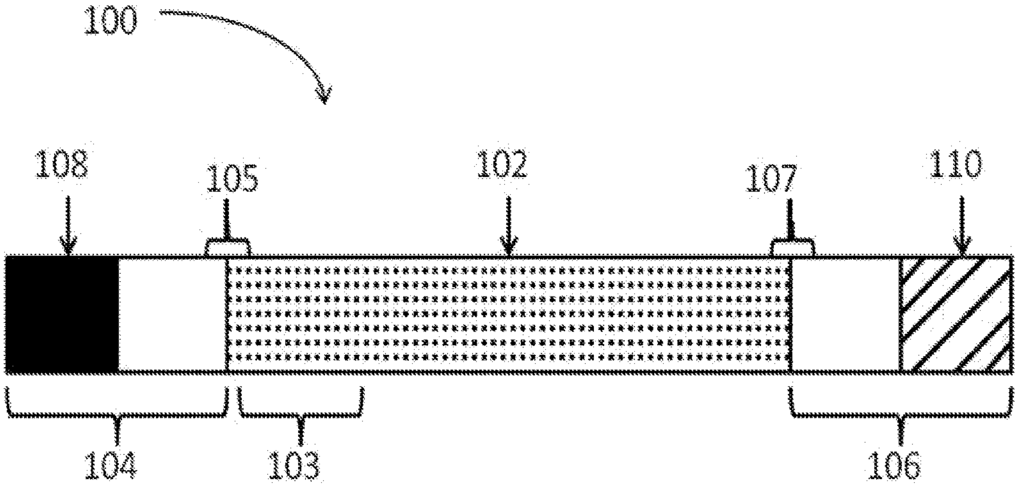
FIG. 4 illustrates an exemplary RNA transcript diagram, according to one embodiment.

FIG. 4 illustrates an exemplary RNA transcript. The RNA transcript 100 here contains a first region of linked nucleotides 102 that is flanked by a first flanking region 104 and a second flaking region 106. As used herein, the "first region" may be referred to as a "coding region" or "region encoding" or simply the "first region." This first region may include, but is not limited to, the gene of interest. The polypeptide of interest may comprise at its 5' terminus one or more signal sequences which are encoded by a signal sequence region 103. The flanking region 104 may comprise a region of linked nucleotides comprising one or more complete or incomplete 5' UTRs sequences. The flanking region 104 may also comprise a 5' terminal cap 108. The second flanking region 106 may comprise a region of linked nucleotides comprising one or more complete or incomplete 3' UTRs. The flanking region 106 may also comprise a 3' tailing sequence 110, e.g., a poly A tail sequence.

Bridging the 5' terminus of the first region 102 and the first flanking region 104 is a first operational region 105. Traditionally this operational region comprises a Start codon. The operational region may alternatively comprise any translation initiation sequence or signal including a Start codon.

Bridging the 3' terminus of the first region 102 and the second flanking region 106 is a second operational region 107. Traditionally this operational region comprises a Stop codon. The operational region may alternatively comprise any translation initiation sequence or signal including a Stop codon. According to the present invention, multiple serial stop codons may also be used.

Generally, the shortest length of the first region of the RNA transcript, e.g., the gene of interest can be the length of a nucleic acid sequence that is sufficient to encode for a dipeptide, a tripeptide, a tetrapeptide, a pentapeptide, a hexapeptide, a heptapeptide, an octapeptide, a nonapeptide, or a decapeptide. In another embodiment, the length may be sufficient to encode a peptide of 2-30 amino acids, e.g. 5-30, 10-30, 2-25, 5-25, 10-25, or 10-20 amino acids. The length may be sufficient to encode for a peptide of at least 11, 12, 13, 14, 15, 17, 20, 25 or 30 amino acids, or a peptide that is no longer than 40 amino acids, e.g. no longer than 35, 30, 25, 20, 17, 15, 14, 13, 12, 11 or 10 amino acids. Examples of dipeptides that the polynucleotide sequences can encode or include, but are not limited to, carnosine and anserine.

Generally, the length of the first region encoding the polypeptide of interest of the present invention is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the RNA transcript includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

In some embodiments, the first and second flanking regions may range independently from 15-1,000 nucleotides in length (e.g., greater than 30, 40, 45, 50, 55, 60, 70, 80, 90, 100, 120, 140, 160, 180, 200, 250, 300, 350, 400, 450, 500, 600, 700, 800, and 900 nucleotides or at least 30, 40, 45, 50, 55, 60, 70, 80, 90, 100, 120, 140, 160, 180, 200, 250, 300, 350, 400, 450, 500, 600, 700, 800, 900, and 1,000 nucleotides).

The tailing sequence may range from 1 to 500 nucleotides in length (e.g., at least 60, 70, 80, 90, 120, 140, 160, 180, 200, 250, 300, 350, 400, 450, or 500 nucleotides). Where the tailing region is a polyA tail, the length may be determined in units of or as a function of polyA Binding Protein binding. In this embodiment, the polyA tail is long enough to bind at least 4 monomers of PolyA Binding Protein. PolyA Binding Protein monomers bind to stretches of approximately 38 nucleotides. As such, it has been observed that polyA tails of about 80 nucleotides and 160 nucleotides are functional.

According to the present invention, the capping region may comprise a single cap or a series of nucleotides forming the cap. In this embodiment the capping region may be from 1 to 10, e.g. 2-9, 3-8, 4-7, 1-5, 5-10, or at least 2, or 10 or fewer nucleotides in length. In some embodiments, the cap is absent.

According to the present invention, the first and second operational regions may range from 3 to 40, e.g., 5-30, 10-20, 15, or at least 4, or 30 or fewer nucleotides in length and may comprise, in addition to a Start and/or Stop codon, one or more signal and/or restriction sequences.

The RNA transcripts can comprise one or more structural and/or chemical modifications or alterations which impart useful properties to the polynucleotide including, in some embodiments, the lack of a substantial induction of the innate immune response of a cell into which the polynucleotide is introduced. As used herein, a "structural" feature or modification is one in which two or more linked nucleotides are inserted, deleted, duplicated, inverted or randomized in an RNA transcript without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" may be chemically modified to "AT-5meC-G". The same polynucleotide may be structurally modified from "ATCG" to "ATCCCG". Here, the dinucleotide "CC" has been inserted, resulting in a structural modification to the polynucleotide.

Removal of DNA Template from RNA Transcript

The linearized plasmid DNA template is removed from the in vitro transcription, e.g., the DNA template is separated from the RNA transcript. In one embodiment, the DNA template is removed chromatographically using an poly A capture, e.g., oligo dT, based affinity purification step. The RNA transcript binds affinity substrate while the DNA template flow through and is removed.

It is typical to utilize DNase I to enzymatically digest DNA template immediately following in vitro transcription. In the methods of the invention, DNase is not utilized. Whole plasmid removal is preferred to enzymatic digestion due to the fact that the risk of degraded DNA fragments hybridizing to the transcribed mRNA is mitigated.

In one embodiment the poly A capture based affinity purification is oligo dT purification. For example, a polythymidine ligand is immobilized to a derivatized chromatography resin. The mechanism of purification involves hybridization of the poly A tail of the RNA transcript to the oligonucleotide ligand. The DNA template will not bind. In addition, RNA transcripts that do not contain Poly A stretches (short aborts and other truncates formed during in vitro transcription) will not bind to the resin and will not form a duplex with the affinity ligand. Poly Adenylated RNA can then be eluted from the resin utilizing a low ionic strength buffer or a competitive binding oligonucleotide solution. A one pot purification method can yield highly purified poly A containing RNA with recoveries >80% actively removes endotoxin, DNA template, and enzymes utilized in the production of RNA using a simple capture and elute methodology with no subsequent fraction of captured poly A containing RNA. This purification increases mRNA product purity and in turn significantly increases target protein expression.

Additional Purification Steps

The method for production of an RNA transcript can include additional purification steps after the in vitro transcription, e.g., an ion exchange chromatography step.

Characterization and Analysis of RNA Transcript

The RNA transcript produced by the methods of the invention can be analyzed and characterized using any number of methods. Analysis can be performed before or after capping. Alternatively, analysis can be performed before or after poly A capture based affinity purification. In another embodiment, analysis can be performed before or after additional purification steps, e.g., anion exchange chromatography and the like.

For example, RNA template quality can be determined using Bioanalyzer chip based electrophoresis system. In other embodiments, RNA template purity is analysed using analytical reverse phase HPLC respectively. Capping efficiency can be analyzed using, e.g., total nuclease digestion followed by MS/MS quantitation of the dinucleotide cap species vs. uncapped GTP species. In vitro efficacy can be analyzed by, e.g., transfecting RNA transcript into a human cell line, e.g., HeLA, PBMC, BJ Fibroblasts, Hek 293). Protein expression of the polypeptide of interest can be quantified using methods such as ELISA or flow cytometry. Immunogenicity can be analyzed by, e.g., transfecting RNA transcripts into cell lines that indicate innate immune stimulation, e.g., PBMCs. Cytokine induction can be analyzed using, e.g., methods such as ELISA to quantify a cytokine, e.g., Interferon-α.

The method of producing RNA transcript of the invention can produce RNA transcript that is at least 30% full length transcript, or at least 35, 40, 45, 50, 55, 60, 65, 70, 75, 80, 85, 90, or at least 95% full length transcript. Purity can be determined as described herein, e.g., via reverse phase HPLC or Bioanalyzer chip based electrophoresis and measure by, e.g., peak area of full length RNA transcript relative to total peak.

Genes of Interest

The DNA template and resulting RNA transcript of the present invention include a gene of interest. The gene of interest encodes a polypeptide of interest selected from, e.g., biologics, antibodies, vaccines, therapeutic proteins or peptides, cell penetrating peptides, secreted proteins, plasma membrane proteins, cytoplasmic or cytoskeletal proteins, intracellular membrane bound proteins, nuclear proteins, proteins associated with human disease, targeting moieties or those proteins encoded by the human genome for which no therapeutic indication has been identified but which nonetheless have utility in areas of research and discovery. The sequence for a particular gene of interest is readily identified by one of skill in the art using public and private databases, e.g., GenBank.

In one embodiment the gene of interest may encode variant polypeptides which have a certain identity with a reference polypeptide sequence. As used herein, a "reference polypeptide sequence" refers to a starting polypeptide sequence. Reference sequences may be wild type sequences or any sequence to which reference is made in the design of another sequence.

The term "identity" as known in the art, refers to a relationship between the sequences of two or more peptides, as determined by comparing the sequences. In the art, identity also means the degree of sequence relatedness between peptides, as determined by the number of matches between strings of two or more amino acid residues. Identity measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the polypeptide variant may have the same or a similar activity as the reference polypeptide. Alternatively, the variant may have an altered activity (e.g., increased or decreased) relative to a reference polypeptide. Generally, variants of a particular polynucleotide or polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.) Other tools are described herein, specifically in the definition of "Identity."

Default parameters in the BLAST algorithm include, for example, an expect threshold of 10, Word size of 28, Match/Mismatch Scores 1, −2, Gap costs Linear. Any filter can be applied as well as a selection for species specific repeats, e.g., *Homo sapiens*.

Biologics

The gene of interest can encode one or more biologics. As used herein, a "biologic" is a polypeptide-based molecule produced by the methods provided herein and which may be used to treat, cure, mitigate, prevent, or diagnose a serious or life-threatening disease or medical condition. Biologics, according to the present invention include, but are not limited to, allergenic extracts (e.g. for allergy shots and tests), blood components, gene therapy products, human tissue or cellular products used in transplantation, vaccines, monoclonal antibodies, cytokines, growth factors, enzymes, thrombolytics, and immunomodulators, among others.

According to the present invention, one or more biologics currently being marketed or in development may be encoded by the polynucleotides, primary constructs or mmRNA of the present invention. While not wishing to be bound by theory, it is believed that incorporation of the encoding polynucleotides of a known biologic into the primary constructs or mmRNA of the invention will result in improved therapeutic efficacy due at least in part to the specificity, purity and/or selectivity of the construct designs.

Antibodies

The gene of interest can encode one or more antibodies or fragments thereof. The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules), as well as antibody fragments. The term "immunoglobulin" (Ig) is used interchangeably with "antibody" herein. As used herein, the term "monoclonal antibody" refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity. Chimeric antibodies of interest herein include, but are not limited to, "primatized" antibodies comprising variable domain antigen-binding sequences derived from a non-human primate (e.g., Old World Monkey, Ape etc.) and human constant region sequences.

An "antibody fragment" comprises a portion of an intact antibody, preferably the antigen binding and/or the variable region of the intact antibody. Examples of antibody fragments include Fab, Fab', F(ab')2 and Fv fragments; diabodies; linear antibodies; nanobodies; single-chain antibody molecules and multispecific antibodies formed from antibody fragments.

Any of the five classes of immunoglobulins, IgA, IgD, IgE, IgG and IgM, may be encoded by the mmRNA of the invention, including the heavy chains designated alpha, delta, epsilon, gamma and mu, respectively. Also included are polynucleotide sequences encoding the subclasses, gamma and mu. Hence any of the subclasses of antibodies may be encoded in part or in whole and include the following subclasses: IgG1, IgG2, IgG3, IgG4, IgA1 and IgA2.

In one embodiment, the gene of interest can encode monoclonal antibodies and/or variants thereof. Variants of antibodies may also include, but are not limited to, substitutional variants, conservative amino acid substitution, insertional variants, deletional variants and/or covalent derivatives. In one embodiment, the primary construct and/or mmRNA disclosed herein may encode an immunoglobulin Fc region. In another embodiment, the primary constructs and/or mmRNA may encode a variant immunoglobulin Fc region. As a non-limiting example, the primary constructs and/or mmRNA may encode an antibody having a variant immunoglobulin Fc region as described in U.S. Pat. No. 8,217,147 herein incorporated by reference in its entirety.

Vaccines

The gene of interest can encode one or more vaccines. As used herein, a "vaccine" is a biological preparation that improves immunity to a particular disease or infectious agent. According to the present invention, one or more vaccines currently being marketed or in development may be encoded by the polynucleotides, primary constructs or mmRNA of the present invention. While not wishing to be bound by theory, it is believed that incorporation into the primary constructs or mmRNA of the invention will result in improved therapeutic efficacy due at least in part to the specificity, purity and selectivity of the construct designs.

Vaccines encoded in the polynucleotides, primary constructs or mmRNA of the invention may be utilized to treat conditions or diseases in many therapeutic areas such as, but not limited to, cardiovascular, CNS, dermatology, endocrinology, oncology, immunology, respiratory, and anti-infective.

Therapeutic Proteins or Peptides

The gene of interest can encode one or more validated or "in testing" therapeutic proteins or peptides. "Therapeutic protein" refers to a protein that, when administered to a cell has a therapeutic, diagnostic, and/or prophylactic effect and/or elicits a desired biological and/or pharmacological effect.

Therapeutic proteins and peptides may be utilized to treat conditions or diseases in many therapeutic areas such as, but not limited to, blood, cardiovascular, CNS, poisoning (including antivenoms), dermatology, endocrinology, genetic, genitourinary, gastrointestinal, musculoskeletal, oncology, and immunology, respiratory, sensory and anti-infective.

Cell-Penetrating Polypeptides

The gene of interest can encode one or more cell-penetrating polypeptides. As used herein, "cell-penetrating polypeptide" or CPP refers to a polypeptide which may facilitate the cellular uptake of molecules. A cell-penetrating polypeptide of the present invention may contain one or more detectable labels. The polypeptides may be partially labeled or completely labeled throughout. The gene of interest can encode the detectable label completely, partially or not at all. The cell-penetrating peptide may also include a signal sequence. As used herein, a "signal sequence" refers to a sequence of amino acid residues bound at the amino terminus of a nascent protein during protein translation. The signal sequence may be used to signal the secretion of the cell-penetrating polypeptide.

In one embodiment, the gene of interest can encode a fusion protein. The fusion protein may be created by operably linking a charged protein to a therapeutic protein. As used herein, "operably linked" refers to the therapeutic protein and the charged protein being connected in such a way to permit the expression of the complex when introduced into the cell. As used herein, "charged protein" refers to a protein that carries a positive, negative or overall neutral electrical charge. Preferably, the therapeutic protein may be covalently linked to the charged protein in the formation of the fusion protein. The ratio of surface charge to total or surface amino acids may be approximately 0.1, 0.2, 0.3, 0.4, 0.5, 0.6, 0.7, 0.8 or 0.9.

The cell-penetrating polypeptide may form a complex after being translated. The complex may comprise a charged protein linked, e.g. covalently linked, to the cell-penetrating polypeptide.

In one embodiment, the cell-penetrating polypeptide may comprise a first domain and a second domain. The first domain may comprise a supercharged polypeptide. The second domain may comprise a protein-binding partner. As used herein, "protein-binding partner" includes, but is not limited to, antibodies and functional fragments thereof, scaffold proteins, or peptides. The cell-penetrating polypeptide may further comprise an intracellular binding partner for the protein-binding partner. The cell-penetrating polypeptide may be capable of being secreted from a cell where the polynucleotide, primary construct or mmRNA may be introduced. The cell-penetrating polypeptide may also be capable of penetrating the first cell.

In a further embodiment, the cell-penetrating polypeptide is capable of penetrating a second cell. The second cell may be from the same area as the first cell, or it may be from a different area. The area may include, but is not limited to, tissues and organs. The second cell may also be proximal or distal to the first cell.

In one embodiment, the cell-penetrating polypeptide which may comprise a protein-binding partner. The protein binding partner may include, but is not limited to, an antibody, a supercharged antibody or a functional fragment. The polynucleotides, primary constructs or mmRNA may be introduced into the cell where a cell-penetrating polypeptide comprising the protein-binding partner is introduced.

Additional Proteins

The gene of interest can encode a secreted protein. The secreted proteins may be selected from, e.g., those in US Patent Publication, 20100255574, the contents of which are incorporated herein by reference in their entirety.

Alternatively, the gene of interest can encode a protein of the plasma membrane; a cytoplasmic or cytoskeletal proteins; a intracellular membrane bound proteins; or a nuclear protein; a targeting moiety (e.g., a protein-binding partner or a receptor on the surface of the cell, which functions to target the cell to a specific tissue space or to interact with a specific moiety); antimicrobial peptides (AMP) or antiviral peptides (AVP).

Flanking Regions: Untranslated Regions (UTRs)

The DNA template and RNA transcript can include UTRs. Untranslated regions (UTRs) of a gene are transcribed but not translated. The 5'UTR starts at the transcription start site and continues to the start codon but does not include the start codon; whereas, the 3'UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides, primary constructs and/or mmRNA of the present invention to enhance the stability of the molecule. The specific features can also be incorporated to ensure controlled down-regulation of the transcript in case they are misdirected to undesired organs sites.

5' UTR and Translation Initiation

Natural 5'UTRs bear features which play roles in translation initiation. They harbor signatures like Kozak sequences which are commonly known to be involved in the process by which the ribosome initiates translation of many genes. Kozak sequences have the consensus CCR(A/G) CCAUGG, where R is a purine (adenine or guanine) three bases upstream of the start codon (AUG), which is followed by another 'G'. 5'UTR also have been known to form secondary structures which are involved in elongation factor binding.

By engineering the features typically found in abundantly expressed genes of specific target organs, one can enhance the stability and protein production of the polynucleotides, primary constructs or mmRNA of the invention. For example, introduction of 5' UTR of liver-expressed mRNA, such as albumin, serum amyloid A, Apolipoprotein A/B/E, transferrin, alpha fetoprotein, erythropoietin, or Factor VIII, could be used to enhance expression of a nucleic acid molecule, such as a mmRNA, in hepatic cell lines or liver. Likewise, use of 5' UTR from other tissue-specific mRNA to improve expression in that tissue is possible for muscle (MyoD, Myosin, Myoglobin, Myogenin, Herculin), for endothelial cells (Tie-1, CD36), for myeloid cells (C/EBP, AML1, G-CSF, GM-CSF, CD11b, MSR, Fr-1, i-NOS), for leukocytes (CD45, CD18), for adipose tissue (CD36, GLUT4, ACRP30, adiponectin) and for lung epithelial cells (SP-A/B/C/D).

Other non-UTR sequences may be incorporated into the 5' (or 3' UTR) UTRs. For example, introns or portions of introns sequences may be incorporated into the flanking regions of the polynucleotides, primary constructs or mmRNA of the invention. Incorporation of intronic sequences may increase protein production as well as mRNA levels.

3' UTR and the AU Rich Elements

3' UTRs are known to have stretches of Adenosines and Uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and TNF-a. Class III ARES are less well defined. These U rich regions do not contain an AUUUA motif c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides, primary constructs or mmRNA of the invention. When engineering specific polynucleotides, primary constructs or mmRNA, one or more copies of an ARE can be introduced to make polynucleotides, primary constructs or mmRNA of the invention less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using polynucleotides, primary constructs or mmRNA of the invention and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

Incorporating microRNA Binding Sites microRNAs (or miRNA) are 19-25 nucleotide long noncoding RNAs that bind to the 3'UTR of nucleic acid molecules and down-regulate gene expression either by reducing nucleic acid molecule stability or by inhibiting translation. The polynucleotides, primary constructs or mmRNA of the invention may comprise one or more microRNA target sequences, microRNA sequences, or microRNA seeds. Such sequences may correspond to any known microRNA such as those taught in US Publication US2005/0261218 and US Publication US2005/0059005, the contents of which are incorporated herein by reference in their entirety.

A microRNA sequence comprises a "seed" region, i.e., a sequence in the region of positions 2-8 of the mature microRNA, which sequence has perfect Watson-Crick complementarity to the miRNA target sequence. A microRNA seed may comprise positions 2-8 or 2-7 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenine (A) opposed to microRNA position 1. See for example, Grimson A, Farh K K, Johnston W K, Garrett-Engele P, Lim L P, Bartel D P; Mol Cell. 2007 Jul. 6; 27(1):91-105; each of which is herein incorporated by reference in their entirety. The bases of the microRNA seed have complete complementarity with the target sequence. By engineering microRNA target sequences into the 3'UTR of RNA transcripts of the invention one can target the molecule for degradation or reduced translation, provided the microRNA in question is available. This process will reduce the hazard of off target effects upon nucleic acid molecule delivery. Identification of microRNA, microRNA target regions, and their expression patterns and role in biology have been reported (Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/1eu.2011.356); Bartel Cell 2009 136:215-233; Landgraf et al, Cell, 2007 129:1401-1414; each of which is herein incorporated by reference in its entirety).

For example, if the nucleic acid molecule is an mRNA and is not intended to be delivered to the liver but ends up there, then miR-122, a microRNA abundant in liver, can inhibit the expression of the gene of interest if one or multiple target sites of miR-122 are engineered into the 3' UTR of the RNA transcripts. Introduction of one or multiple binding sites for different microRNA can be engineered to further decrease the longevity, stability, and protein translation of a RNA transcripts.

As used herein, the term "microRNA site" refers to a microRNA target site or a microRNA recognition site, or any nucleotide sequence to which a microRNA binds or associates. It should be understood that "binding" may follow traditional Watson-Crick hybridization rules or may reflect any stable association of the microRNA with the target sequence at or adjacent to the microRNA site.

Conversely, for the purposes of the RNA transcripts of the present invention, microRNA binding sites can be engineered out of (i.e. removed from) sequences in which they naturally occur in order to increase protein expression in specific tissues. For example, miR-122 binding sites may be removed to improve protein expression in the liver. Regulation of expression in multiple tissues can be accomplished through introduction or removal or one or several microRNA binding sites.

Examples of tissues where microRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126). MicroRNA can also regulate complex biological processes such as angiogenesis (miR-132) (Anand and Cheresh Curr Opin Hematol 2011 18:171-176; herein incorporated by reference in its entirety). In the RNA transcripts of the present invention, binding sites for microRNAs that are involved in such processes may be removed or introduced, in order to tailor the expression of the RNA transcripts expression to biologically relevant cell types or to the context of relevant biological processes. A listing of MicroRNA, miR sequences and miR binding sites is listed in Table 9 of U.S. Provisional Application No. 61/753,661 filed Jan. 17, 2013, in Table 9 of U.S. Provisional Application No. 61/754,159 filed Jan. 18, 2013, and in Table 7 of U.S. Provisional Application No. 61/758,921 filed Jan. 31, 2013, each of which are herein incorporated by reference in their entireties. g Lastly, through an understanding of the expression patterns of microRNA in different cell types, RNA transcripts can be engineered for more targeted expression in specific cell types or only under specific biological conditions. Through introduction of tissue-specific microRNA binding sites, RNA transcripts could be designed that would be optimal for protein expression in a tissue or in the context of a biological condition.

Transfection experiments can be conducted in relevant cell lines, using engineered RNA transcripts and protein production can be assayed at various time points post-transfection. For example, cells can be transfected with different microRNA binding site-engineering RNA transcripts and by using an ELISA kit to the relevant protein and assaying protein produced at 6 hour, 12 hour, 24 hour, 48 hour, 72 hour and 7 days post-transfection. In vivo experiments can also be conducted using microRNA-binding site-engineered molecules to examine changes in tissue-specific expression of formulated RNA transcripts.

Viral Sequences

Additional viral sequences such as, but not limited to, the translation enhancer sequence of the barley yellow dwarf virus (BYDV-PAV), the Jaagsiekte sheep retrovirus (JSRV) and/or the Enzootic nasal tumor virus (See e.g., International Pub. No. WO2012129648; herein incorporated by reference in its entirety) can be engineered and inserted in the 3' UTR of the RNA transcripts of the invention and can stimulate the translation of the construct in vitro and in vivo. Transfection experiments can be conducted in relevant cell lines at and protein production can be assayed by ELISA at 12 hr, 24 hr, 48 hr, 72 hr and day 7 post-transfection.

IRES Sequences

Further, provided are RNA transcripts which may contain an internal ribosome entry site (IRES). First identified as a feature Picorna virus RNA, IRES plays an important role in initiating protein synthesis in absence of the 5' cap structure. An IRES may act as the sole ribosome binding site, or may serve as one of multiple ribosome binding sites of an mRNA. RNA transcripts containing more than one functional ribosome binding site may encode several peptides or polypeptides that are translated independently by the ribosomes ("multicistronic nucleic acid molecules"). When RNA transcripts are provided with an IRES, further optionally provided is a second translatable region. Examples of IRES sequences that can be used according to the invention include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

Poly-A Tails

During RNA processing, a long chain of adenine nucleotides (poly-A tail) may be added to a polynucleotide such as an mRNA molecules in order to increase stability. Immediately after transcription, the 3' end of the transcript may be cleaved to free a 3' hydroxyl. Then poly-A polymerase adds a chain of adenine nucleotides to the RNA. The process, called polyadenylation, adds a poly-A tail that can be between, for example, approximately 100 and 250 residues long.

It has been discovered that unique poly-A tail lengths provide certain advantages to the RNA transcripts of the present invention.

In one embodiment the poly A tail is 5-300 nucleotides in length. In another embodiment, the poly A tail is 60-160 nucleotides in length.

In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides). In some embodiments, the polynucleotide, primary construct, or mmRNA includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In one embodiment, the poly-A tail is designed relative to the length of the overall RNA transcripts. This design may be based on the length of the coding region, the length of a particular feature or region (such as the first or flanking regions), or based on the length of the ultimate product expressed from the RNA transcripts.

In this context the poly-A tail may be 10, 20, 30, 40, 50, 60, 70, 80, 90, or 100% greater in length than the RNA transcripts or feature thereof. The poly-A tail may also be designed as a fraction of RNA transcripts to which it belongs. In this context, the poly-A tail may be 10, 20, 30, 40, 50, 60, 70, 80, or 90% or more of the total length of the construct or the total length of the construct minus the poly-A tail. Further, engineered binding sites and conjugation of RNA transcripts for Poly-A binding protein may enhance expression.

Additionally, multiple distinct RNA transcripts may be linked together to the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In one embodiment, the polynucleotide primary constructs of the present invention are designed to include a polyA-G Quartet. The G-quartet is a cyclic hydrogen bonded array of four guanine nucleotides that can be formed by G-rich sequences in both DNA and RNA. In this embodiment, the G-quartet is incorporated at the end of the poly-A tail. The resultant mmRNA construct is assayed for stability, protein production and other parameters including half-life at various time points. It has been discovered that the polyA-G quartet results in protein production equivalent to at least 75% of that seen using a poly-A tail of 120 nucleotides alone.

Modified Nucleotides

Herein, in a polynucleotide (such as a primary construct or an mRNA molecule), the terms "modification" or, as appropriate, "modified" refer to modification with respect to A, G, U or C ribonucleotides. Generally, herein, these terms are not intended to refer to the ribonucleotide modifications in naturally occurring 5'-terminal mRNA cap moieties. In a polypeptide, the term "modification" refers to a modification as compared to the canonical set of 20 amino acids, moiety)

The modifications may be various distinct modifications. In some embodiments, the coding region, the flanking regions and/or the terminal regions may contain one, two, or more (optionally different) nucleoside or nucleotide modifications. In some embodiments, a modified polynucleotide, primary construct, or mmRNA introduced to a cell may exhibit reduced degradation in the cell, as compared to an unmodified polynucleotide, primary construct, or mmRNA.

The polynucleotides, primary constructs, and mmRNA can include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro).

In certain embodiments, modifications (e.g., one or more modifications) are present in each of the sugar and the internucleoside linkage. Modifications according to the present invention may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

As described herein, the polynucleotides, primary constructs, and mmRNA of the invention do not substantially induce an innate immune response of a cell into which the mRNA is introduced. Features of an induced innate immune response include 1) increased expression of pro-inflammatory cytokines, 2) activation of intracellular PRRs (RIG-I, MDA5, etc, and/or 3) termination or reduction in protein translation.

In certain embodiments, it may desirable to intracellularly degrade a modified nucleic acid molecule introduced into the cell. For example, degradation of a modified nucleic acid molecule may be preferable if precise timing of protein production is desired. Thus, in some embodiments, the invention provides a modified nucleic acid molecule containing a degradation domain, which is capable of being acted on in a directed manner within a cell. In another aspect, the present disclosure provides polynucleotides comprising a nucleoside or nucleotide that can disrupt the binding of a major groove interacting, e.g. binding, partner with the polynucleotide (e.g., where the modified nucleotide has decreased binding affinity to major groove interacting partner, as compared to an unmodified nucleotide).

The polynucleotides, primary constructs, and mmRNA can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, vectors, etc.). In some embodiments, the polynucleotides, primary constructs, or mmRNA may include one or more messenger RNAs (mRNAs) and one or more modified nucleoside or nucleotides (e.g., mmRNA molecules). Details for these polynucleotides, primary constructs, and mmRNA follow.

Polynucleotides and Primary Constructs

The polynucleotides, primary constructs, and mmRNA of the invention includes a first region of linked nucleosides encoding a polypeptide of interest, a first flanking region located at the 5' terminus of the first region, and a second flanking region located at the 3' terminus of the first region.

In some embodiments, the polynucleotide, primary construct, or mmRNA (e.g., the first region, first flanking region, or second flanking region) includes n number of linked nucleosides having Formula (Ia) or Formula (Ia-1):

(Ia)

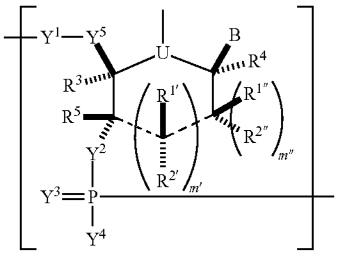

-continued (Ia-1)

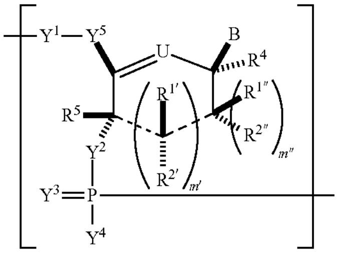

or a pharmaceutically acceptable salt or stereoisomer thereof, wherein

U is O, S, N(RU)nu, or C(RU)nu, wherein nu is an integer from 0 to 2 and each RU is, independently, H, halo, or optionally substituted alkyl;

- - - is a single bond or absent;

each of R1', R2', R1", R2", R1, R2, R3, R4, and R5 is, independently, if present, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; wherein the combination of R3 with one or more of R1', R1", R2', R2", or R5 (e.g., the combination of R1' and R3, the combination of R1" and R3, the combination of R2' and R3, the combination of R2" and R3, or the combination of R5 and R3) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); wherein the combination of R5 with one or more of R1', R1", R2', or R2" (e.g., the combination of R1' and R5, the combination of R1" and R5, the combination of R2' and R5, or the combination of R2" and R5) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); and wherein the combination of R4 and one or more of R1', R1", R2', R2", R3, or R5 can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); each of m' and m" is, independently, an integer from 0 to 3 (e.g., from 0 to 2, from 0 to 1, from 1 to 3, or from 1 to 2);

each of Y1, Y2, and Y3, is, independently, O, S, Se, —NRN1-, optionally substituted alkylene, or optionally substituted heteroalkylene, wherein RN1 is H, optionally substituted alkyl, optionally substituted alkenyl, optionally substituted alkynyl, optionally substituted aryl, or absent;

each Y4 is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each Y5 is, independently, O, S, Se, optionally substituted alkylene (e.g., methylene), or optionally substituted heteroalkylene;

n is an integer from 1 to 100,000; and

B is a nucleobase (e.g., a purine, a pyrimidine, or derivatives thereof), wherein the combination of B and R1', the combination of B and R2', the combination of B and R1", or the combination of B and R2" can, taken together with the carbons to which they are attached, optionally form a bicyclic group (e.g., a bicyclic heterocyclyl) or wherein the combination of B, R1", and R3 or the combination of B, R2", and R3 can optionally form a tricyclic or tetracyclic group (e.g., a tricyclic or tetracyclic heterocyclyl, such as in Formula (IIo)-(IIp) herein). In some embodiments, the polynucleotide, primary construct, or mmRNA includes a modified ribose. In some embodiments, the polynucleotide, primary construct, or mmRNA (e.g., the first region, the first flanking region, or the second flanking region) includes n number of linked nucleosides having Formula (Ia-2)-(Ia-5) or a pharmaceutically acceptable salt or stereoisomer thereof.

(Ia-2)

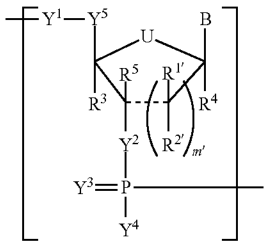

(Ia-3)

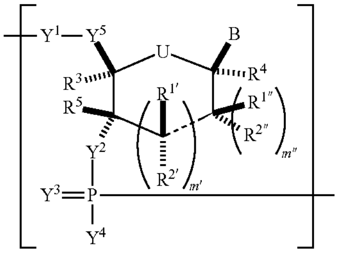

(Ia-4)

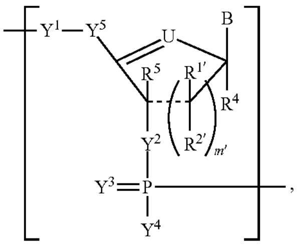

, (Ia-5)

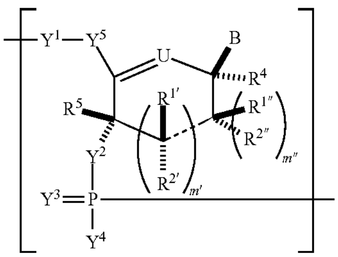

.

In some embodiments, the polynucleotide, primary construct, or mmRNA (e.g., the first region, the first flanking region, or the second flanking region) includes n number of linked nucleosides having Formula (Ib) or Formula (Ib-1):

(Ib)

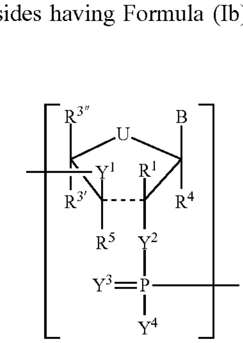

, (Ib-1)

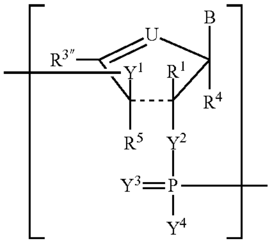

or a pharmaceutically acceptable salt or stereoisomer thereof, wherein

U is O, S, N(RU)nu, or C(RU)nu, wherein nu is an integer from 0 to 2 and each RU is, independently, H, halo, or optionally substituted alkyl;

- - - is a single bond or absent;

each of R1, R3', R3", and R4 is, independently, H, halo, hydroxy, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; and wherein the combination of R1 and R3' or the combination of R1 and R3" can be taken together to form optionally substituted alkylene or optionally substituted heteroalkylene (e.g., to produce a locked nucleic acid);

each R5 is, independently, H, halo, hydroxy, optionally substituted alkyl, optionally substituted alkoxy, optionally substituted alkenyloxy, optionally substituted alkynyloxy, optionally substituted aminoalkoxy, optionally substituted alkoxyalkoxy, or absent;

each of Y1, Y2, and Y3 is, independently, O, S, Se, —NRN1-, optionally substituted alkylene, or optionally substituted heteroalkylene, wherein RN1 is H, optionally substituted alkyl, optionally substituted alkenyl, optionally substituted alkynyl, or optionally substituted aryl;

each Y4 is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkoxy, or optionally substituted amino;

n is an integer from 1 to 100,000; and

B is a nucleobase.

In some embodiments, the polynucleotide, primary construct, or mmRNA (e.g., the first region, first flanking region, or second flanking region) includes n number of linked nucleosides having Formula (Ic):

(Ic)

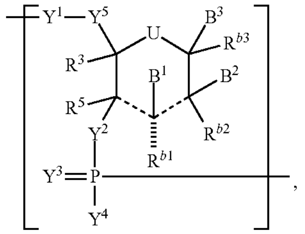

or a pharmaceutically acceptable salt or stereoisomer thereof, wherein

U is O, S, N(RU)nu, or C(RU)nu, wherein nu is an integer from 0 to 2 and each RU is, independently, H, halo, or optionally substituted alkyl;

- - - is a single bond or absent;

each of B1, B2, and B3 is, independently, a nucleobase (e.g., a purine, a pyrimidine, or derivatives thereof, as described herein), H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, or optionally substituted aminoalkynyl, wherein one and only one of B1, B2, and B3 is a nucleobase;

each of Rb1, Rb2, Rb3, R3, and R5 is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl or optionally substituted aminoalkynyl;

each of Y1, Y2, and Y3, is, independently, O, S, Se, —NRN1-, optionally substituted alkylene, or optionally substituted heteroalkylene, wherein RN1 is H, optionally substituted alkyl, optionally substituted alkenyl, optionally substituted alkynyl, or optionally substituted aryl;

each Y4 is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each Y5 is, independently, O, S, Se, optionally substituted alkylene (e.g., methylene), or optionally substituted heteroalkylene;

n is an integer from 1 to 100,000; and wherein the ring including U can include one or more double bonds.

In particular embodiments, the ring including U does not have a double bond between U-CB3Rb3 or between CB3Rb3-CB2Rb2.

In some embodiments, the polynucleotide, primary construct, or mmRNA (e.g., the first region, first flanking region, or second flanking region) includes n number of linked nucleosides having Formula (Id):

(Id)

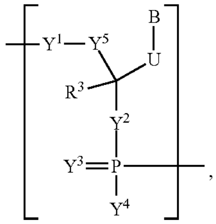

or a pharmaceutically acceptable salt or stereoisomer thereof, wherein

U is O, S, N(RU)nu, or C(RU)nu, wherein nu is an integer from 0 to 2 and each RU is, independently, H, halo, or optionally substituted alkyl;

each R3 is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, or optionally substituted aminoalkynyl;

each of Y1, Y2, and Y3, is, independently, O, S, Se, —NRN1-, optionally substituted alkylene, or optionally substituted heteroalkylene, wherein RN1 is H, optionally substituted alkyl, optionally substituted alkenyl, optionally substituted alkynyl, or optionally substituted aryl;

each Y4 is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each Y5 is, independently, O, S, optionally substituted alkylene (e.g., methylene), or optionally substituted heteroalkylene;

n is an integer from 1 to 100,000; and

B is a nucleobase (e.g., a purine, a pyrimidine, or derivatives thereof).

In some embodiments, the polynucleotide, primary construct, or mmRNA (e.g., the first region, first flanking region, or second flanking region) includes n number of linked nucleosides having Formula (Ie):

(Ie)

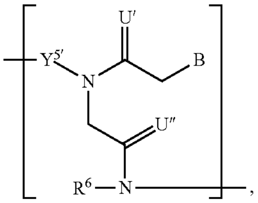

or a pharmaceutically acceptable salt or stereoisomer thereof, wherein each of U' and U" is, independently, O, S, N(RU)nu, or C(RU)nu, wherein nu is an integer from 0 to 2 and each RU is, independently, H, halo, or optionally substituted alkyl;

each R6 is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, or optionally substituted aminoalkynyl;

each Y5' is, independently, O, S, optionally substituted alkylene (e.g., methylene or ethylene), or optionally substituted heteroalkylene;

n is an integer from 1 to 100,000; and

B is a nucleobase (e.g., a purine, a pyrimidine, or derivatives thereof).

In some embodiments, the polynucleotide, primary construct, or mmRNA (e.g., the first region, first flanking region, or second flanking region) includes n number of linked nucleosides having Formula (If) or (If-1):

(If)

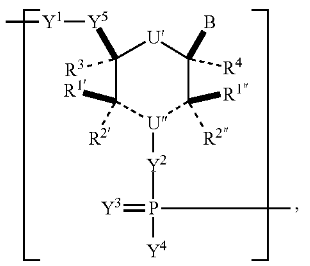

(If-1)

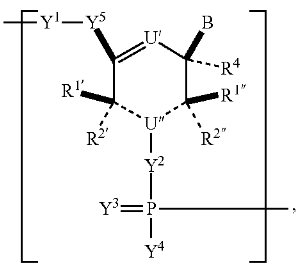

or a pharmaceutically acceptable salt or stereoisomer thereof, wherein each of U' and U" is, independently, O, S, N, N(RU)nu, or C(RU)nu, wherein nu is an integer from 0 to 2 and each RU is, independently, H, halo, or optionally substituted alkyl (e.g., U' is O and U" is N);

- - - is a single bond or absent;

each of R1', R2', R1", R2", R3, and R4 is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; and wherein the combination of R1' and R3, the combination of R1" and R3, the combination of R2' and R3, or the combination of R2" and R3 can be taken together to form optionally substituted alkylene or optionally substituted heteroalkylene (e.g., to produce a locked nucleic acid); each of m' and m" is, independently, an integer from 0 to 3 (e.g., from 0 to 2, from 0 to 1, from 1 to 3, or from 1 to 2);

each of Y1, Y2, and Y3, is, independently, O, S, Se, —NRN1-, optionally substituted alkylene, or optionally substituted heteroalkylene, wherein RN1 is H, optionally substituted alkyl, optionally substituted alkenyl, optionally substituted alkynyl, optionally substituted aryl, or absent;

each Y4 is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each Y5 is, independently, O, S, Se, optionally substituted alkylene (e.g., methylene), or optionally substituted heteroalkylene;

n is an integer from 1 to 100,000; and

B is a nucleobase (e.g., a purine, a pyrimidine, or derivatives thereof).

In some embodiments of the polynucleotides, primary constructs, or mmRNA (e.g., Formulas (Ia), (Ia-1)-(Ia-3), (Ib)-(If), and (IIa)-(IIp)), the ring including U has one or two double bonds.

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), each of R1, R1', and R1", if present, is H. In further embodiments, each of R2, R2', and R2", if present, is, independently, H, halo (e.g., fluoro), hydroxy, optionally substituted alkoxy (e.g., methoxy or ethoxy), or optionally substituted alkoxyalkoxy. In particular embodiments, alkoxyalkoxy is —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl). In some embodiments, s2 is 0, s1 is 1 or 2, s3 is 0 or 1, and R' is C1-6 alkyl.

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), each of R2, R2', and R2", if present, is H. In further embodiments, each of R1, R1', and R1", if present, is, independently, H, halo (e.g., fluoro), hydroxy, optionally substituted alkoxy (e.g., methoxy or ethoxy), or optionally substituted alkoxyalkoxy. In particular embodiments, alkoxyalkoxy is —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl). In some embodiments, s2 is 0, s1 is 1 or 2, s3 is 0 or 1, and R' is C1-6 alkyl.

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), each of R3, R4, and R5 is, independently, H, halo (e.g., fluoro), hydroxy, optionally substituted alkyl, optionally substituted alkoxy (e.g., methoxy or ethoxy), or optionally substituted alkoxyalkoxy. In particular embodiments, R3 is H, R4 is H, R5 is H, or R3, R4, and R5 are all H. In particular embodiments, R3 is C1-6 alkyl, R4 is C1-6 alkyl, R5 is C1-6 alkyl, or R3, R4, and R5 are all C1-6 alkyl. In particular embodiments, R3 and R4 are both H, and R5 is C1-6 alkyl.

In some embodiments of the polynucleotides, primary constructs, or mmRNA (e.g., Formulas (Ia)-(Ia-5), (Ib)-(If- 1), (IIa)-(IIp), (IIb-1), (IIb-2), (IIc-1)-(IIc-2), (IIn-1), (IIn-2), (IVa)-(IV1), and (IXa)-(IXr)), R3 and R5 join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl, such as trans-3',4' analogs, wherein R3 and R5 join together to form heteroalkylene (e.g., —(CH2)b1O(CH2)b2O(CH2)b3-, wherein each of b1, b2, and b3 are, independently, an integer from 0 to 3).

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), R3 and one or more of R1', R1", R2', R2", or R5 join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl, R3 and one or more of R1', R1", R2', R2", or R5 join together to form heteroalkylene (e.g., —(CH2)b1O(CH2)b2O(CH2)b3-, wherein each of b1, b2, and b3 are, independently, an integer from 0 to 3).

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), R5 and one or more of R1', R1", R2', or R2" join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl, R5 and one or more of R1', R1", R2', or R2" join together to form heteroalkylene (e.g., —(CH2)b1O(CH2)b2O(CH2)b3-, wherein each of b1, b2, and b3 are, independently, an integer from 0 to 3).

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), each Y2 is, independently, O, S, or —NRN1-, wherein RN1 is H, optionally substituted alkyl, optionally substituted alkenyl, optionally substituted alkynyl, or optionally substituted aryl. In particular embodiments, Y2 is NRN1-, wherein RN1 is H or optionally substituted alkyl (e.g., C1-6 alkyl, such as methyl, ethyl, isopropyl, or n-propyl).

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), each Y3 is, independently, O or S.

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), R1 is H; each R2 is, independently, H, halo (e.g., fluoro), hydroxy, optionally substituted alkoxy (e.g., methoxy or ethoxy), or optionally substituted alkoxyalkoxy (e.g., —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl, such as wherein s2 is 0, s1 is 1 or 2, s3 is 0 or 1, and R' is C1-6 alkyl); each Y2 is, independently, O or —NRN1-, wherein RN1 is H, optionally substituted alkyl, optionally substituted alkenyl, optionally substituted alkynyl, or optionally substituted aryl (e.g., wherein RN1 is H or optionally substituted alkyl (e.g., C1-6 alkyl, such as methyl, ethyl, isopropyl, or n-propyl)); and each Y3 is, independently, O or S (e.g., S). In further embodiments, R3 is H, halo (e.g., fluoro), hydroxy, optionally substituted alkyl, optionally substituted alkoxy (e.g., methoxy or ethoxy), or optionally substituted alkoxyalkoxy. In yet further embodiments, each Y1 is, independently, O or —NRN1-, wherein RN1 is H, optionally substituted alkyl, optionally substituted alkenyl, optionally substituted alkynyl, or optionally substituted aryl (e.g., wherein RN1 is H or optionally substituted alkyl (e.g., C1-6 alkyl, such as methyl, ethyl, isopropyl, or n-propyl)); and each Y4 is, independently, H, hydroxy, thiol, optionally substituted alkyl, optionally substituted alkoxy, optionally substituted thioalkoxy, optionally substituted alkoxyalkoxy, or optionally substituted amino.

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), each R1 is, independently, H, halo (e.g., fluoro), hydroxy, optionally substituted alkoxy (e.g., methoxy or ethoxy), or optionally substituted alkoxyalkoxy (e.g., —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl, such as wherein s2 is 0, s1 is 1 or 2, s3 is 0 or 1, and R' is C1-6 alkyl); R2 is H; each Y2 is, independently, O or —NRN1-, wherein RN1 is H, optionally substituted alkyl, optionally substituted alkenyl, optionally substituted alkynyl, or optionally substituted aryl (e.g., wherein RN1 is H or optionally substituted alkyl (e.g., C1-6 alkyl, such as methyl, ethyl, isopropyl, or n-propyl)); and each Y3 is, independently, O or S (e.g., S). In further embodiments, R3 is H, halo (e.g., fluoro), hydroxy, optionally substituted alkyl, optionally substituted alkoxy (e.g., methoxy or ethoxy), or optionally substituted alkoxyalkoxy. In yet further embodiments, each Y1 is, independently, O or —NRN1-, wherein RN1 is H, optionally substituted alkyl, optionally substituted alkenyl, optionally substituted alkynyl, or optionally substituted aryl (e.g., wherein RN1 is H or optionally substituted alkyl (e.g., C1-6 alkyl, such as methyl, ethyl, isopropyl, or n-propyl)); and each Y4 is, independently, H, hydroxy, thiol, optionally substituted alkyl, optionally substituted alkoxy, optionally substituted thioalkoxy, optionally substituted alkoxyalkoxy, or optionally substituted amino.

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), the ring including U is in the β-D (e.g., β-D-ribo) configuration.

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), the ring including U is in the α-L (e.g., α-L-ribo) configuration.

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), one or more B is not pseudouridine (ψ) or 5-methyl-cytidine (m5C). In some embodiments, about 10% to about 100% of n number of B nucleobases is not w or m5C (e.g., from 10% to 20%, from 10% to 35%, from 10% to 50%, from 10% to 60%, from 10% to 75%, from 10% to 90%, from 10% to 95%, from 10% to 98%, from 10% to 99%, from 20% to 35%, from 20% to 50%, from 20% to 60%, from 20% to 75%, from 20% to 90%, from 20% to 95%, from 20% to 98%, from 20% to 99%, from 20% to 100%, from 50% to 60%, from 50% to 75%, from 50% to 90%, from 50% to 95%, from 50% to 98%, from 50% to 99%, from 50% to 100%, from 75% to 90%, from 75% to 95%, from 75% to 98%, from 75% to 99%, and from 75% to 100% of n number of B is not ψor m5C). In some embodiments, B is not ψor m5C.

In some embodiments of the polynucleotides, primary constructs, or mmRNA (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IV1), and (IXa)-(IXr)), when B is an unmodified nucleobase selected from cytosine, guanine, uracil and adenine, then at least one of Y1, Y2, or Y3 is not 0.

In some embodiments, the polynucleotide, primary construct, or mmRNA includes a modified ribose. In some embodiments, the polynucleotide, primary construct, or mmRNA (e.g., the first region, the first flanking region, or the second flanking region) includes n number of linked nucleosides having Formula (IIa)-(IIc):

(IIa)

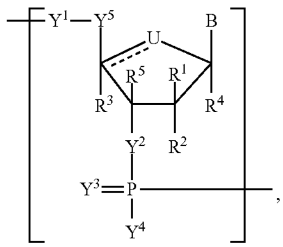

, (IIb)

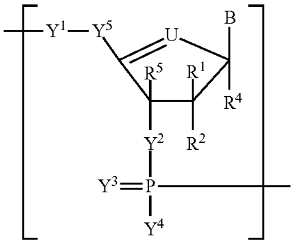

, or (IIc)

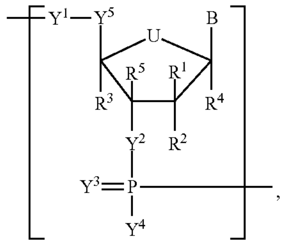

, or a pharmaceutically acceptable salt or stereoisomer thereof. In particular embodiments, U is O or C(RU)nu, wherein nu is an integer from 0 to 2 and each RU is, independently, H, halo, or optionally substituted alkyl (e.g., U is —CH2- or —CH—). In other embodiments, each of R1, R2, R3, R4, and R5 is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent (e.g., each R1 and R2 is, independently, H, halo, hydroxy, optionally substituted alkyl, or optionally substituted alkoxy; each R3 and R4 is, independently, H or optionally substituted alkyl; and R5 is H or hydroxy), and - - - is a single bond or double bond.

In particular embodiments, the polynucleotidesor mmRNA includes n number of linked nucleosides having Formula (IIb-1)-(IIb-2):

(IIb-1)

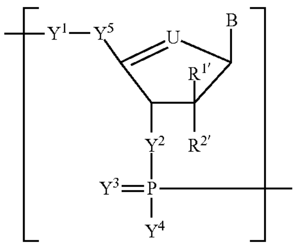

or (IIb-2)

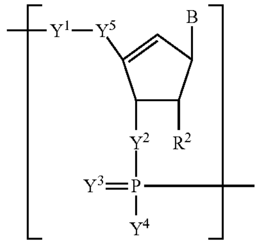

or a pharmaceutically acceptable salt or stereoisomer thereof. In some embodiments, U is O or C(RU)nu, wherein nu is an integer from 0 to 2 and each RU is, independently, H, halo, or optionally substituted alkyl (e.g., U is —CH2- or —CH—). In other embodiments, each of R1 and R2 is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent (e.g., each R1 and R2 is, independently, H, halo, hydroxy, optionally substituted alkyl, or optionally substituted alkoxy, e.g., H, halo, hydroxy, alkyl, or alkoxy). In particular embodiments, R2 is hydroxy or optionally substituted alkoxy (e.g., methoxy, ethoxy, or any described herein).

In particular embodiments, the polynucleotide, primary construct, or mmRNA includes n number of linked nucleosides having Formula (IIc-1)-(IIc-4):

(IIc-1)

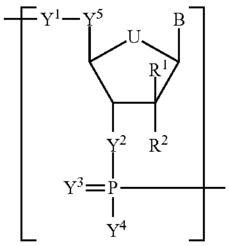

,

-continued (IIc-2)

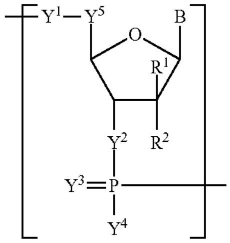

, (IIc-3)

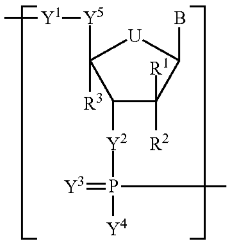

, or (IIc-4)

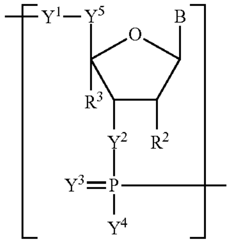

, or a pharmaceutically acceptable salt or stereoisomer thereof. In some embodiments, U is O or C(RU)nu, wherein nu is an integer from 0 to 2 and each RU is, independently, H, halo, or optionally substituted alkyl (e.g., U is —CH2- or —CH—). In some embodiments, each of R1, R2, and R3 is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent (e.g., each R1 and R2 is, independently, H, halo, hydroxy, optionally substituted alkyl, or optionally substituted alkoxy, e.g., H, halo, hydroxy, alkyl, or alkoxy; and each R3 is, independently, H or optionally substituted alkyl)). In particular embodiments, R2 is optionally substituted alkoxy (e.g., methoxy or ethoxy, or any described herein). In particular embodiments, R1 is optionally substituted alkyl, and R2 is hydroxy. In other embodiments, R1 is hydroxy, and R2 is optionally substituted alkyl. In further embodiments, R3 is optionally substituted alkyl.

In some embodiments, the polynucleotide, primary construct, or mmRNA includes an acyclic modified ribose. In some embodiments, the polynucleotide, primary construct, or mmRNA (e.g., the first region, the first flanking region, or the second flanking region) includes n number of linked nucleosides having Formula (IId)-(IIf):

(IId)

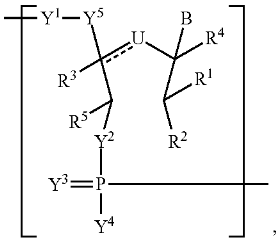

, (IIe)

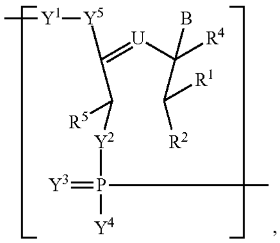

, or (IIf)

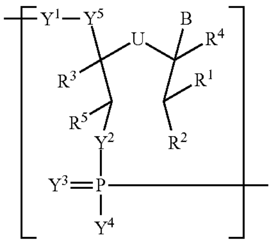

, or a pharmaceutically acceptable salt or stereoisomer thereof.

In some embodiments, the polynucleotide, primary construct, or mmRNA includes an acyclic modified hexitol. In some embodiments, the polynucleotide, primary construct, or mmRNA (e.g., the first region, the first flanking region, or the second flanking region) includes n number of linked nucleosides Formula (IIg)-(IIj):

(IIg)

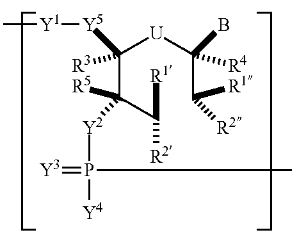

, (IIh)

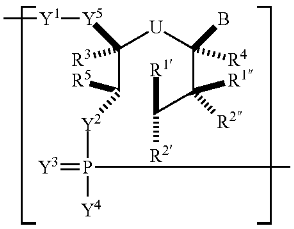

,

-continued (IIi)

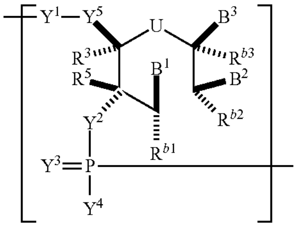

, or (IIj)

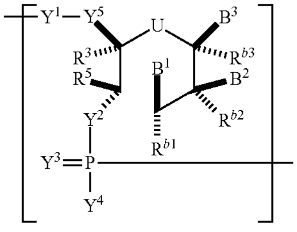

, or a pharmaceutically acceptable salt or stereoisomer thereof.

In some embodiments, the polynucleotide, primary construct, or mmRNA includes a sugar moiety having a contracted or an expanded ribose ring. In some embodiments, the polynucleotide, primary construct, or mmRNA (e.g., the first region, the first flanking region, or the second flanking region) includes n number of linked nucleosides having Formula (IIk)-(IIm):

(IIk)

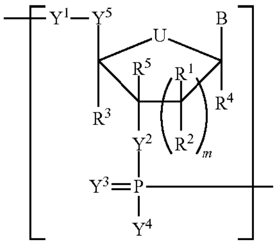

, (IIl)

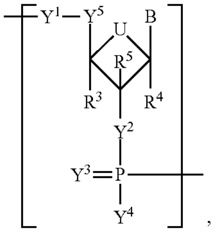

, or (IIm)

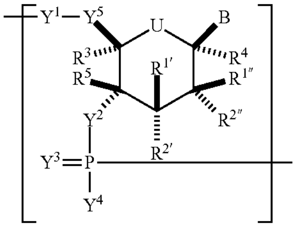

, or a pharmaceutically acceptable salt or stereoisomer thereof, wherein each of R1', R1", R2', and R2" is, independently, H, halo, hydroxy, optionally substituted alkyl, optionally substituted alkoxy, optionally substituted alkenyloxy, optionally substituted alkynyloxy, optionally substituted aminoalkoxy, optionally substituted alkoxyalkoxy, or absent; and wherein the combination of R2' and R3 or the combination of R2" and R3 can be taken together to form optionally substituted alkylene or optionally substituted heteroalkylene.

In some embodiments, the polynucleotide, primary construct, or mmRNA includes a locked modified ribose. In some embodiments, the polynucleotide, primary construct, or mmRNA (e.g., the first region, the first flanking region, or the second flanking region) includes n number of linked nucleosides having Formula (IIn):

(IIn)

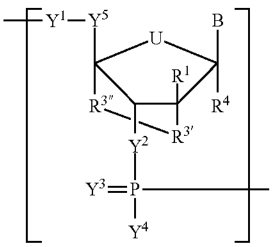

, or a pharmaceutically acceptable salt or stereoisomer thereof, wherein R3' is O, S, or —NRN1-, wherein RN1 is H, optionally substituted alkyl, optionally substituted alkenyl, optionally substituted alkynyl, or optionally substituted aryl and R3" is optionally substituted alkylene (e.g., —CH2-, —CH2CH2-, or —CH2CH2CH2-) or optionally substituted heteroalkylene (e.g., —CH2NH—, —CH2CH2NH—, —CH2OCH2-, or —CH2CH2OCH2-) (e.g., R3' is O and R3" is optionally substituted alkylene (e.g., —CH2-, —CH2CH2-, or —CH2CH2CH2-)).

In some embodiments, the polynucleotide, primary construct, or mmRNA includes n number of linked nucleosides having Formula (IIn-1)-(II-n2):

(IIn-1)

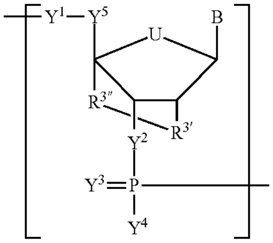

or (IIn-2)

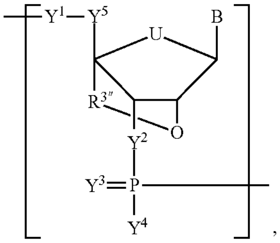

, or a pharmaceutically acceptable salt or stereoisomer thereof, wherein R3' is O, S, or —NRN1-, wherein RN1 is H, optionally substituted alkyl, optionally substituted alkenyl, optionally substituted alkynyl, or optionally substituted aryl and R3" is optionally substituted alkylene (e.g., —CH2-, —CH2CH2-, or —CH2CH2CH2-) or optionally substituted heteroalkylene (e.g., —CH2NH—, —CH2CH2NH—, —CH2OCH2-, or —CH2CH2OCH2-) (e.g., R3' is O and R3" is optionally substituted alkylene (e.g., —CH2-, —CH2CH2-, or —CH2CH2CH2-)).

In some embodiments, the polynucleotide, primary construct, or mmRNA includes a locked modified ribose that forms a tetracyclic heterocyclyl. In some embodiments, the polynucleotide, primary construct, or mmRNA (e.g., the first region, the first flanking region, or the second flanking region) includes n number of linked nucleosides having Formula (IIo):

(IIo)

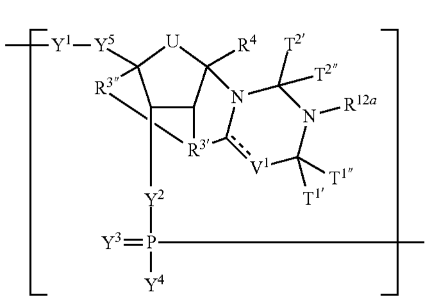

or (IIp)

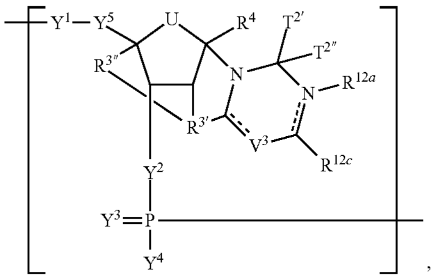

, or a pharmaceutically acceptable salt or stereoisomer thereof, wherein R12a, R12c, T1', T1", T2', T2", V1, and V3 are as described herein.

Any of the formulas for the polynucleotides, primary constructs, or mmRNA can include one or more nucleobases described herein (e.g., Formulas (b1)-(b43).

In one embodiment, the present invention provides methods of preparing a polynucleotide, primary construct, or mmRNA, wherein the polynucleotide comprises n number of nucleosides having Formula (Ia), as defined herein:

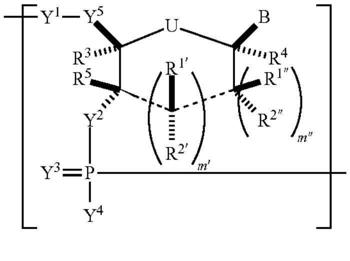

, the method comprising reacting a compound of Formula (IIIa), as defined herein:

(IIIa)

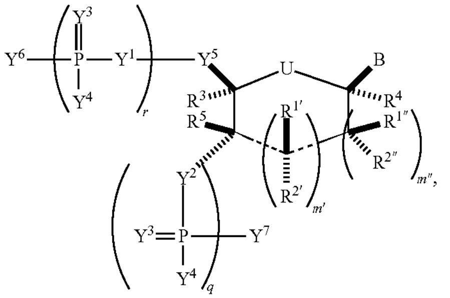

with an RNA polymerase, and a cDNA template.

In a further embodiment, the present invention provides methods of amplifying a polynucleotide, primary construct, or mmRNA comprising at least one nucleotide (e.g., mmRNA molecule), the method comprising: reacting a compound of Formula (IIIa), as defined herein, with a primer, a cDNA template, and an RNA polymerase.

In one embodiment, the present invention provides methods of preparing a polynucleotide, primary construct, or mmRNA comprising at least one nucleotide (e.g., mmRNA molecule), wherein the polynucleotide comprises n number of nucleosides having Formula (Ia), as defined herein:

(Ia-1)

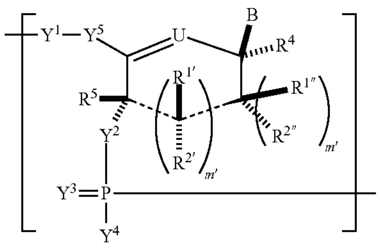

, the method comprising reacting a compound of Formula (IIIa-1), as defined herein:

(IIIa-1)

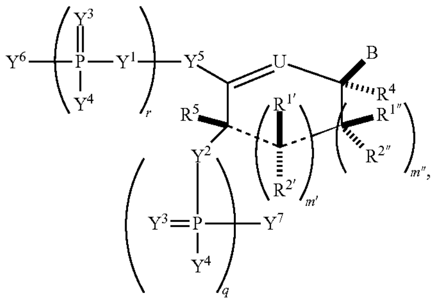

with an RNA polymerase, and a cDNA template.

In a further embodiment, the present invention provides methods of amplifying a polynucleotide, primary construct, or mmRNA comprising at least one nucleotide (e.g., mmRNA molecule), the method comprising:

reacting a compound of Formula (IIIa-1), as defined herein, with a primer, a cDNA template, and an RNA polymerase.

In one embodiment, the present invention provides methods of preparing a modified mRNA comprising at least one nucleotide (e.g., mmRNA molecule), wherein the polynucleotide comprises n number of nucleosides having Formula (Ia-2), as defined herein:

(Ia-2)

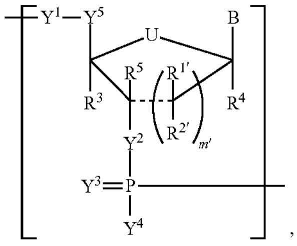

the method comprising reacting a compound of Formula (IIIa-2), as defined herein:

(IIIa-2)

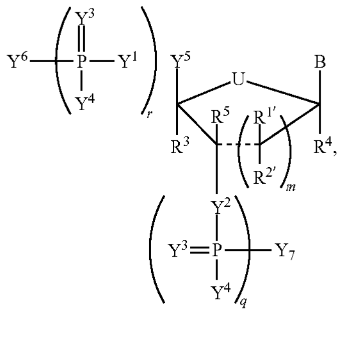

with an RNA polymerase, and a cDNA template.

In a further embodiment, the present invention provides methods of amplifying a modified mRNA comprising at least one nucleotide (e.g., mmRNA molecule), the method comprising: reacting a compound of Formula (IIIa-2), as defined herein, with a primer, a cDNA template, and an RNA polymerase.

In some embodiments, the reaction may be repeated from 1 to about 7,000 times. In any of the embodiments herein, B may be a nucleobase of Formula (b1)-(b43).

The polynucleotides, primary constructs, and mmRNA can optionally include 5' and/or 3' flanking regions, which are described herein.

Modified RNA (mmRNA) Molecules

The present invention also includes building blocks, e.g., modified ribonucleosides, modified ribonucleotides, of modified RNA (mmRNA) molecules. For example, these building blocks can be useful for preparing the polynucleotides, primary constructs, or mmRNA of the invention.

In some embodiments, the building block molecule has Formula (IIIa) or (IIIa-1):

(IIIa)

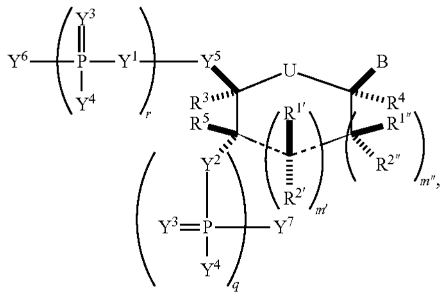

(IIIa-1)

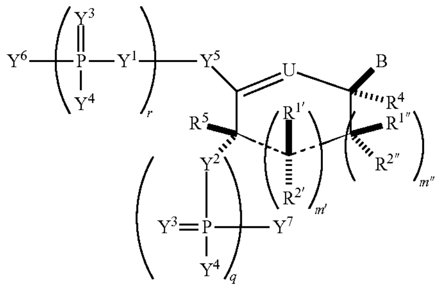

or a pharmaceutically acceptable salt or stereoisomer thereof, wherein the substituents are as described herein (e.g., for Formula (Ia) and (Ia-1)), and wherein when B is an unmodified nucleobase selected from cytosine, guanine, uracil and adenine, then at least one of Y1, Y2, or Y3 is not O.

In some embodiments, the building block molecule, which may be incorporated into a polynucleotide, primary construct, or mmRNA, has Formula (IVa)-(IVb):

(IVa)

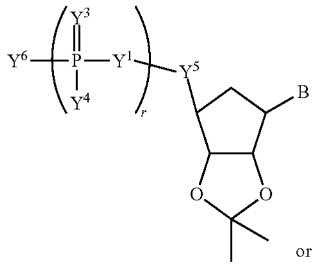

or (IVb)

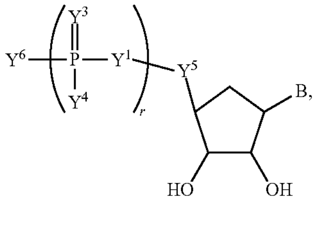

or a pharmaceutically acceptable salt or stereoisomer thereof, wherein B is as described herein (e.g., any one of (b1)-(b43)). In particular embodiments, Formula (IVa) or (IVb) is combined with a modified uracil (e.g., any one of formulas (b1)-(b9), (b21)-(b23), and (b28)-(b31), such as formula (b1), (b8), (b28), (b29), or (b30). In particular embodiments, Formula (IVa) or (IVb) is combined with a modified cytosine (e.g., any one of formulas (b10)-(b14), (b24), (b25), and (b32)-(b36), such as formula (b10) or (b32). In particular embodiments, Formula (IVa) or (IVb) is combined with a modified guanine (e.g., any one of formulas (b15)-(b17) and (b37)-(b40)). In particular embodiments, Formula (IVa) or (IVb) is combined with a modified adenine (e.g., any one of formulas (b18)-(b20) and (b41)-(b43)).

In some embodiments, the building block molecule, which may be incorporated into a polynucleotide, primary construct, or mmRNA, has Formula (IVc)-(IVk):

(IVc)

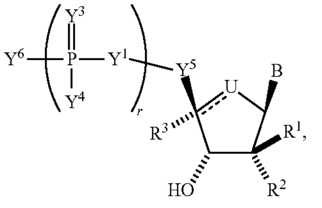

(IVd)

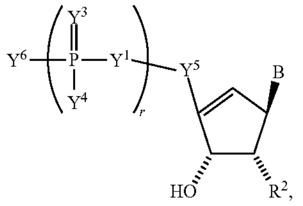

(IVe)

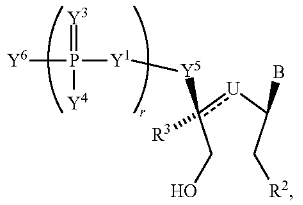

(IVf)

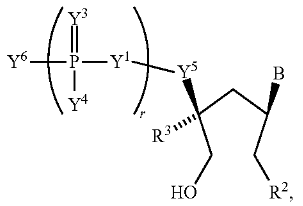

(IVg)

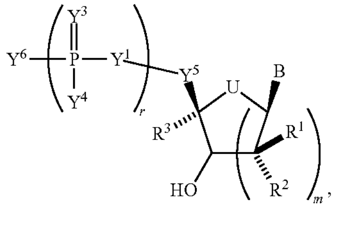

(IVh)

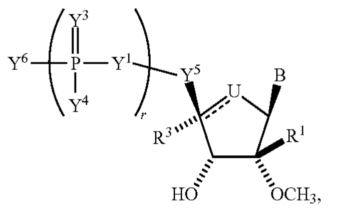

-continued (IVi)

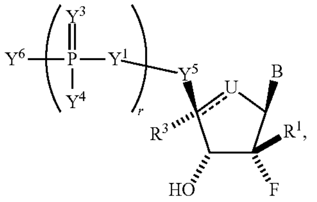

(IVj)

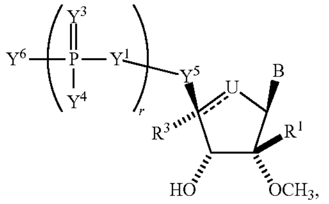

(IVk)

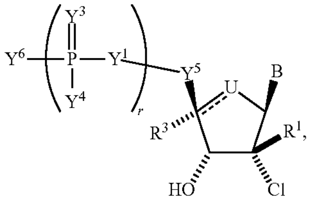

or (IVl)

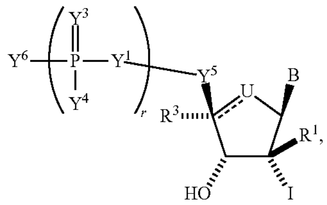

or a pharmaceutically acceptable salt or stereoisomer thereof, wherein B is as described herein (e.g., any one of (b1)-(b43)). In particular embodiments, one of Formulas (IVc)-(IVk) is combined with a modified uracil (e.g., any one of formulas (b1)-(b9), (b21)-(b23), and (b28)-(b31), such as formula (b1), (b8), (b28), (b29), or (b30)). In particular embodiments, one of Formulas (IVc)-(IVk) is combined with a modified cytosine (e.g., any one of formulas (b10)-(b14), (b24), (b25), and (b32)-(b36), such as formula (b10) or (b32)). In particular embodiments, one of Formulas (IVc)-(IVk) is combined with a modified guanine (e.g., any one of formulas (b15)-(b17) and (b37)-(b40)). In particular embodiments, one of Formulas (IVc)-(IVk) is combined with a modified adenine (e.g., any one of formulas (b18)-(b20) and (b41)-(b43)).

In other embodiments, the building block molecule, which may be incorporated into a polynucleotide, primary construct, or mmRNA, has Formula (Va) or (Vb):

(Va)

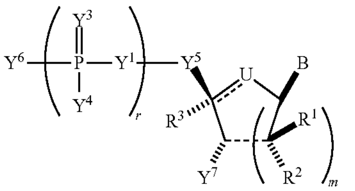

or

-continued (Vb)

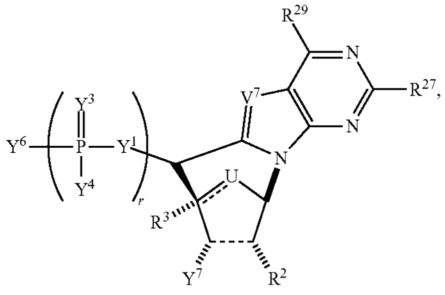

or a pharmaceutically acceptable salt or stereoisomer thereof, wherein B is as described herein (e.g., any one of (b1)-(b43)).

In other embodiments, the building block molecule, which may be incorporated into a polynucleotide, primary construct, or mmRNA, has Formula (IXa)-(IXd):

(IXa)

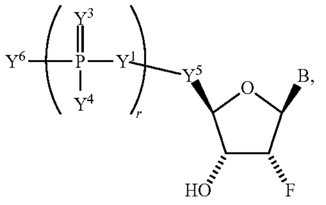

(IXb)

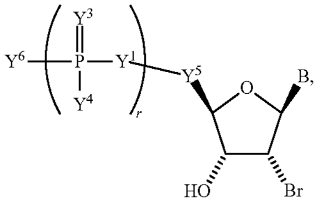

(IXc)

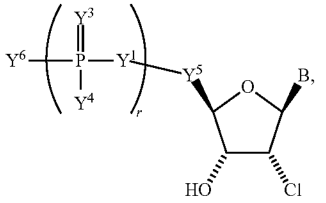

or (IXd)

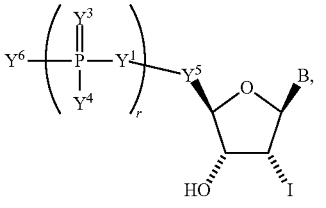

or a pharmaceutically acceptable salt or stereoisomer thereof, wherein B is as described herein (e.g., any one of (b1)-(b43)). In particular embodiments, one of Formulas (IXa)-(IXd) is combined with a modified uracil (e.g., any one of formulas (b1)-(b9), (b21)-(b23), and (b28)-(b31), such as formula (b1), (b8), (b28), (b29), or (b30)). In particular embodiments, one of Formulas (IXa)-(IXd) is combined with a modified cytosine (e.g., any one of formulas (b10)-(b14), (b24), (b25), and (b32)-(b36), such as formula (b10) or (b32)). In particular embodiments, one of Formulas (IXa)-(IXd) is combined with a modified guanine (e.g., any one of formulas (b15)-(b17) and (b37)-(b40)). In particular embodiments, one of Formulas (IXa)-(IXd) is combined with a modified adenine (e.g., any one of formulas (b18)-(b20) and (b41)-(b43)).

In other embodiments, the building block molecule, which may be incorporated into a polynucleotide, primary construct, or mmRNA, has Formula (IXe)-(IXg):

(IXe)

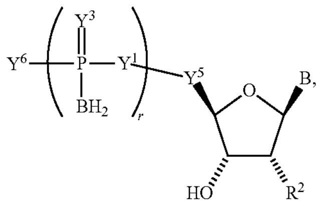

(IXf)

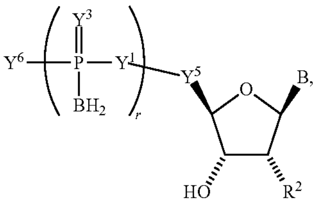

or (IXg)

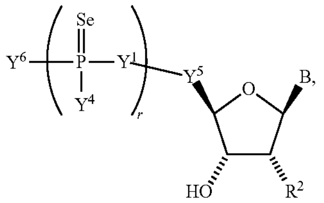

or a pharmaceutically acceptable salt or stereoisomer thereof, wherein B is as described herein (e.g., any one of (b1)-(b43)). In particular embodiments, one of Formulas (IXe)-(IXg) is combined with a modified uracil (e.g., any one of formulas (b1)-(b9), (b21)-(b23), and (b28)-(b31), such as formula (b1), (b8), (b28), (b29), or (b30)). In particular embodiments, one of Formulas (IXe)-(IXg) is combined with a modified cytosine (e.g., any one of formulas (b10)-(b14), (b24), (b25), and (b32)-(b36), such as formula (b10) or (b32)). In particular embodiments, one of Formulas (IXe)-(IXg) is combined with a modified guanine (e.g., any one of formulas (b15)-(b17) and (b37)-(b40)). In particular embodiments, one of Formulas (IXe)-(IXg) is combined with a modified adenine (e.g., any one of formulas (b18)-(b20) and (b41)-(b43)).

In other embodiments, the building block molecule, which may be incorporated into a polynucleotide, primary construct, or mmRNA, has Formula (IXh)-(IXk):

(IXh)

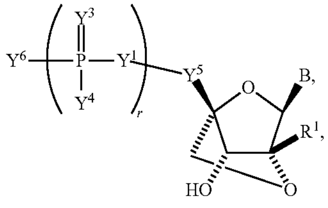

-continued (IXi)

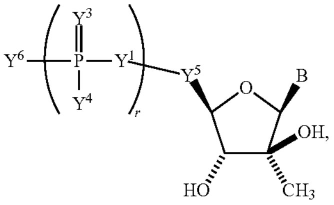

(IXj)

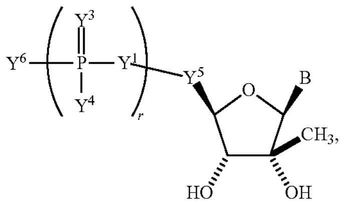

or (IXk)

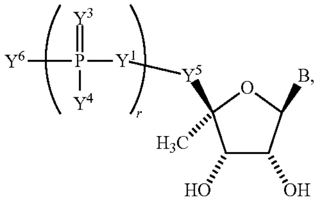

or a pharmaceutically acceptable salt or stereoisomer thereof, wherein B is as described herein (e.g., any one of (b1)-(b43)). In particular embodiments, one of Formulas (IXh)-(IXk) is combined with a modified uracil (e.g., any one of formulas (b1)-(b9), (b21)-(b23), and (b28)-(b31), such as formula (b1), (b8), (b28), (b29), or (b30)). In particular embodiments, one of Formulas (IXh)-(IXk) is combined with a modified cytosine (e.g., any one of formulas (b10)-(b14), (b24), (b25), and (b32)-(b36), such as formula (b10) or (b32)). In particular embodiments, one of Formulas (IXh)-(IXk) is combined with a modified guanine (e.g., any one of formulas (b15)-(b17) and (b37)-(b40)). In particular embodiments, one of Formulas (IXh)-(IXk) is combined with a modified adenine (e.g., any one of formulas (b18)-(b20) and (b41)-(b43)).

In other embodiments, the building block molecule, which may be incorporated into a polynucleotide, primary construct, or mmRNA, has Formula (IXl)-(IXr):

(IXl)

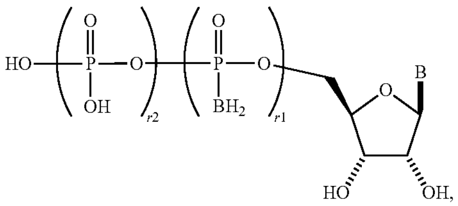

(IXm)

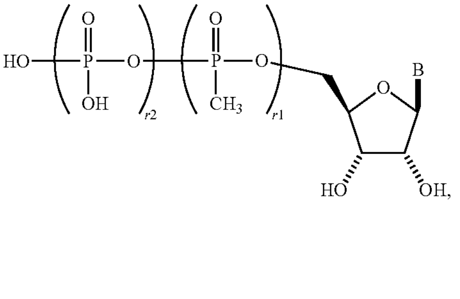

-continued (IXn)

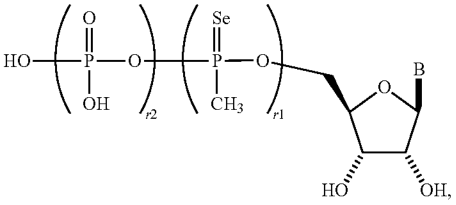

(IXo)

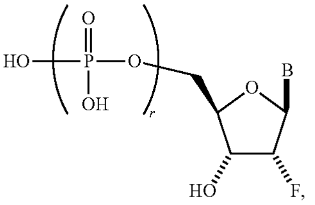

(IXp)

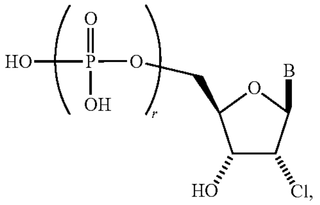

(IXq)

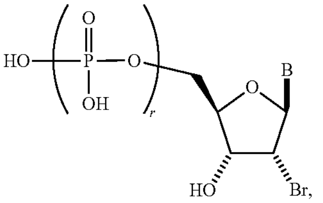

or (IXr)

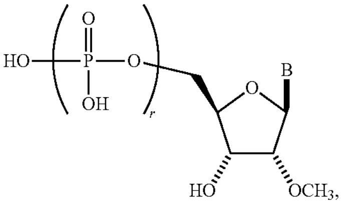

or a pharmaceutically acceptable salt or stereoisomer thereof, wherein each r1 and r2 is, independently, an integer from 0 to 5 (e.g., from 0 to 3, from 1 to 3, or from 1 to 5) and B is as described herein (e.g., any one of (b1)-(b43)). In particular embodiments, one of Formulas (IXl)-(IXr) is combined with a modified uracil (e.g., any one of formulas (b1)-(b9), (b21)-(b23), and (b28)-(b31), such as formula (b1), (b8), (b28), (b29), or (b30)). In particular embodiments, one of Formulas (IXl)-(IXr) is combined with a modified cytosine (e.g., any one of formulas (b10)-(b14), (b24), (b25), and (b32)-(b36), such as formula (b10) or (b32)). In particular embodiments, one of Formulas (IXl)-(IXr) is combined with a modified guanine (e.g., any one of formulas (b15)-(b17) and (b37)-(b40)). In particular embodiments, one of Formulas (IXl)-(IXr) is combined with a modified adenine (e.g., any one of formulas (b18)-(b20) and (b41)-(b43)).

In some embodiments, the building block molecule, which may be incorporated into a polynucleotide, primary construct, or mmRNA, can be selected from the group consisting of:

(BB-1)
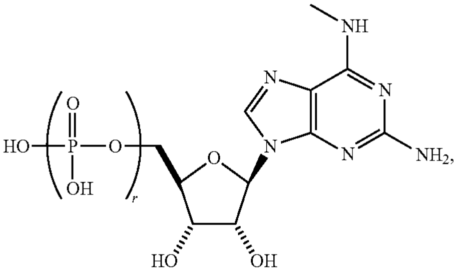
(BB-2)
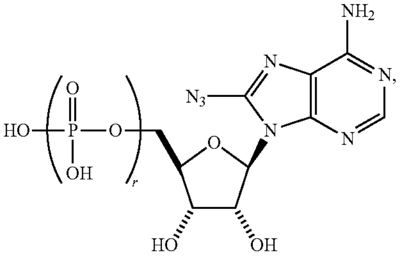
(BB-3)
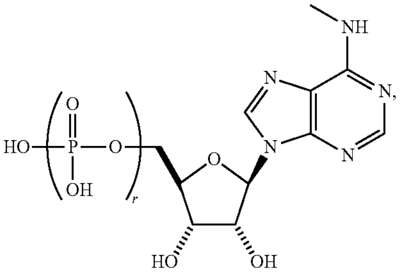
(BB-4)
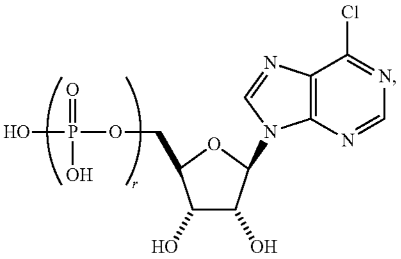
(BB-5)
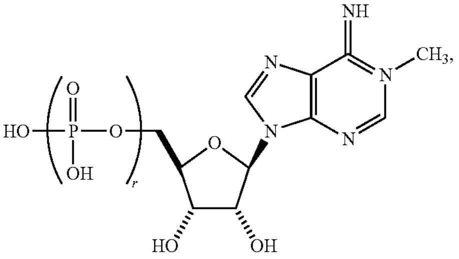
(BB-6)
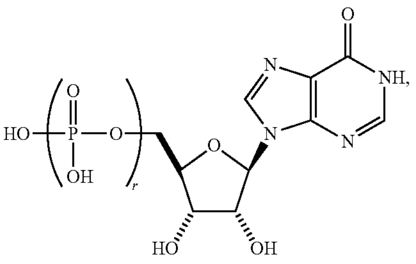
-continued
(BB-7)
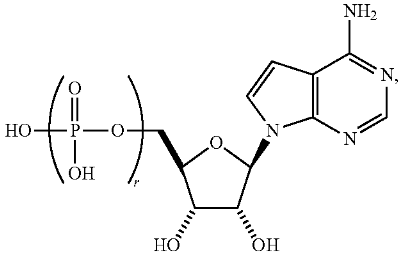
(BB-8)
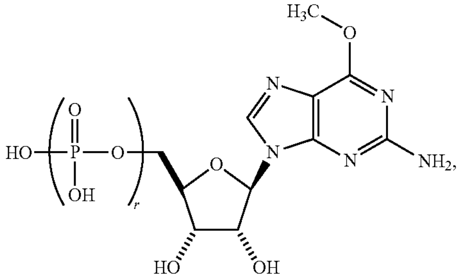
(BB-9)
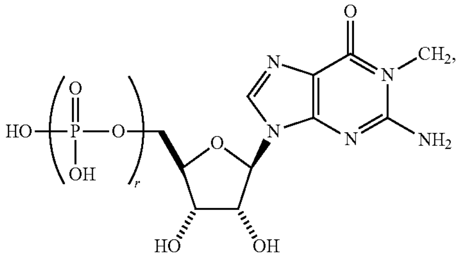
(BB-10)
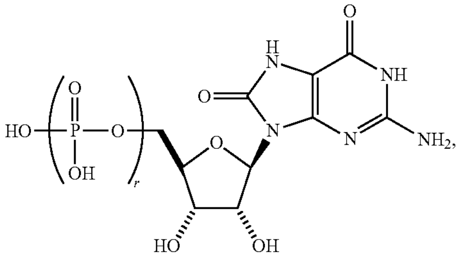
(BB-11)
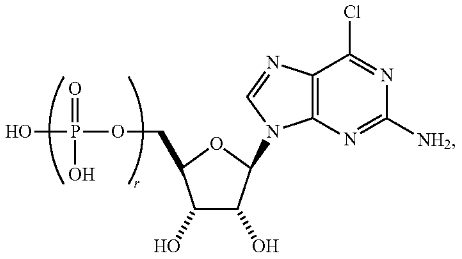
(BB-12)
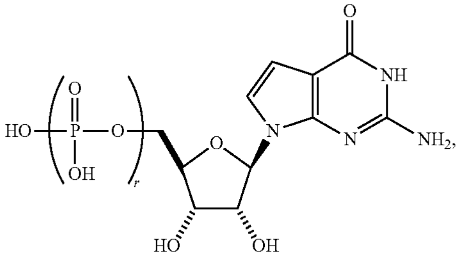

or a pharmaceutically acceptable salt or stereoisomer thereof, wherein each r is, independently, an integer from 0 to 5 (e.g., from 0 to 3, from 1 to 3, or from 1 to 5).

In some embodiments, the building block molecule, which may be incorporated into a polynucleotide, primary construct, or mmRNA, can be selected from the group consisting of:

(BB-13)

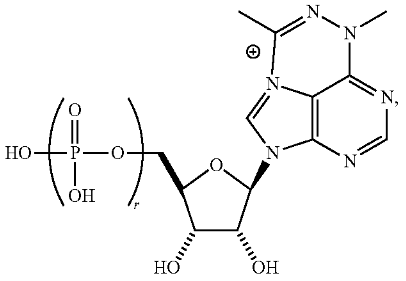

(BB-14)

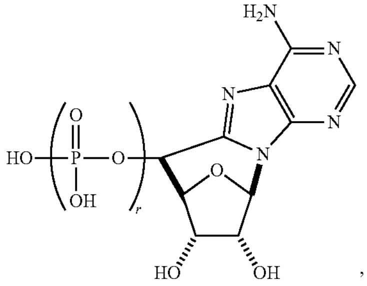

, (BB-15)

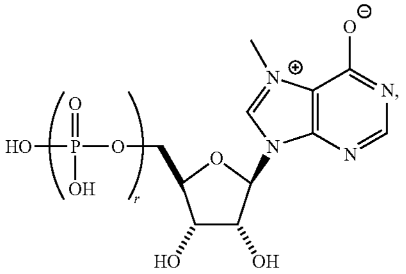

(BB-16)

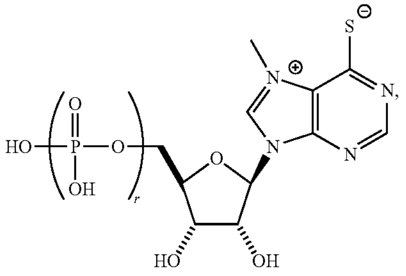

(BB-17)

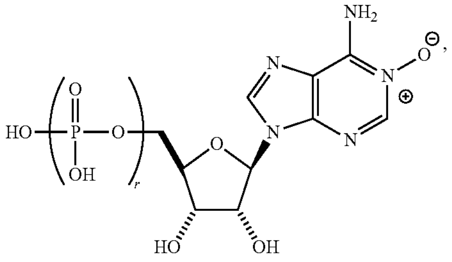

-continued (BB-18)

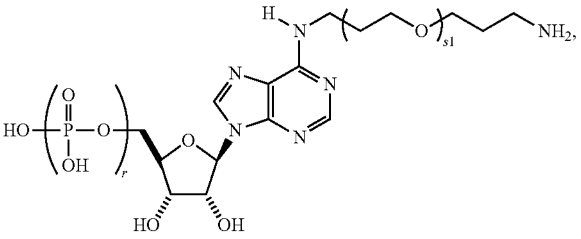

(BB-19)

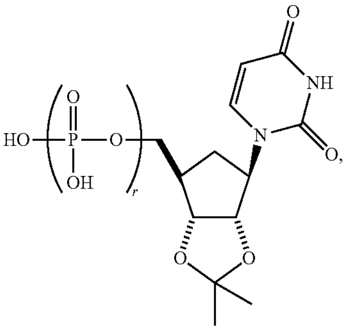

and (BB-20)

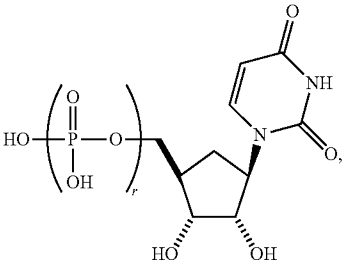

or a pharmaceutically acceptable salt or stereoisomer thereof, wherein each r is, independently, an integer from 0 to 5 (e.g., from 0 to 3, from 1 to 3, or from 1 to 5) and s1 is as described herein.

In some embodiments, the building block molecule, which may be incorporated into a nucleic acid (e.g., RNA, mRNA, polynucleotide, primary construct, or mmRNA), is a modified uridine (e.g., selected from the group consisting of:

(BB-21)

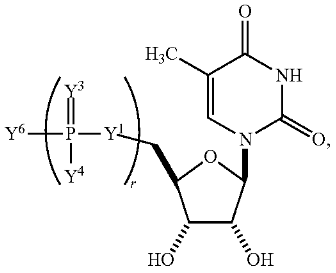

-continued
(BB-22)
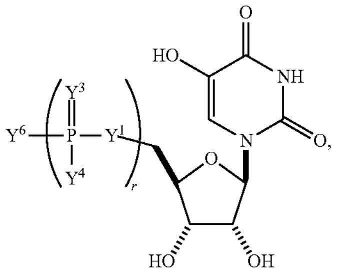
(BB-23)
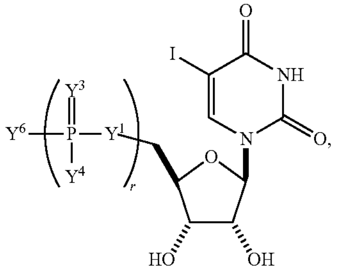
(BB-24)
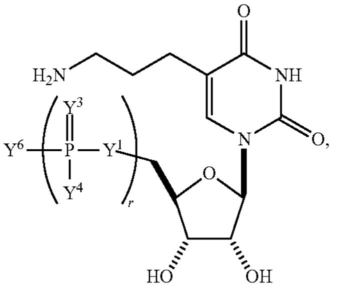
(BB-25)
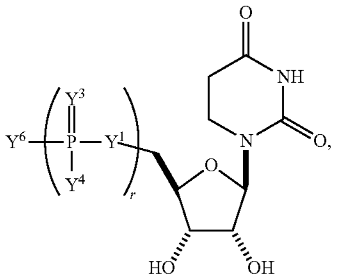
(BB-26)
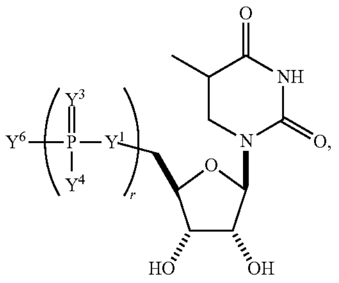
-continued
(BB-27)
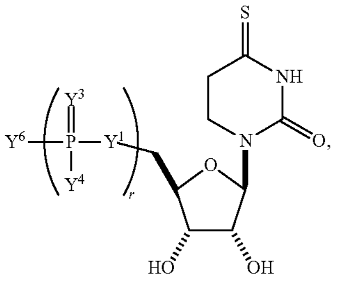
(BB-28)
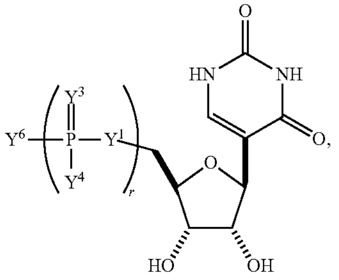
(BB-29)
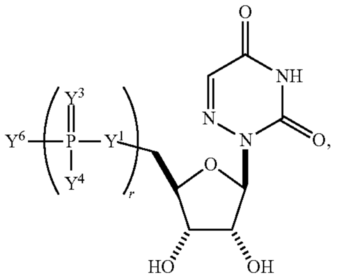
(BB-30)
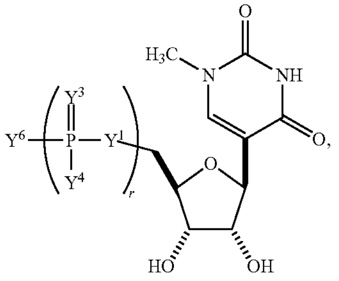
(BB-31)
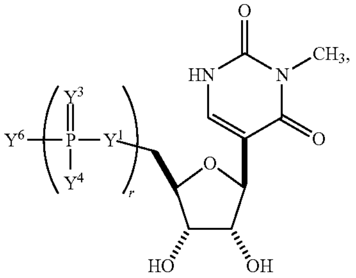

-continued
(BB-32)
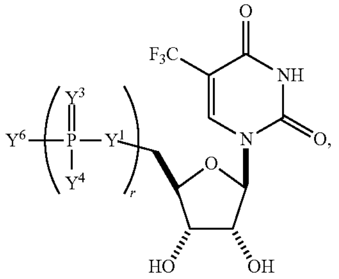
(BB-33)
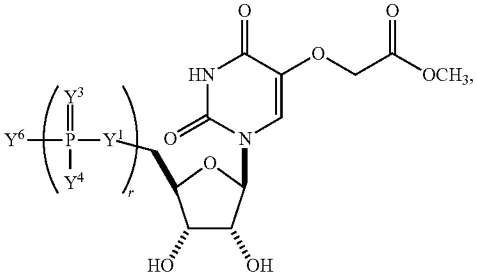
(BB-34)
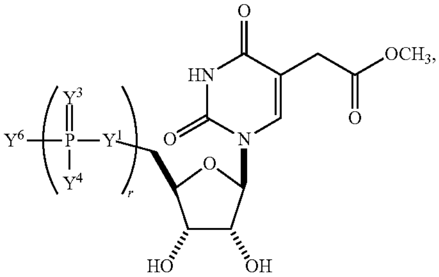
(BB-35)
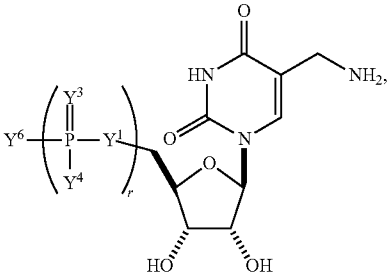
(BB-36)
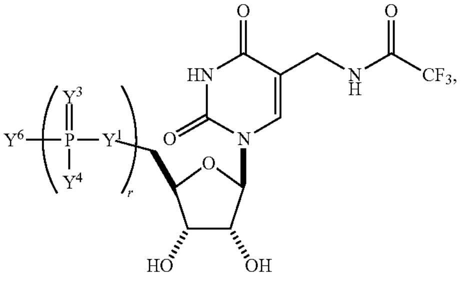
-continued
(BB-37)
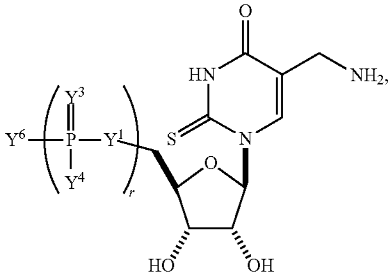
(BB-38)
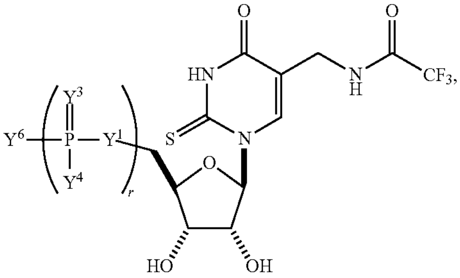
(BB-39)
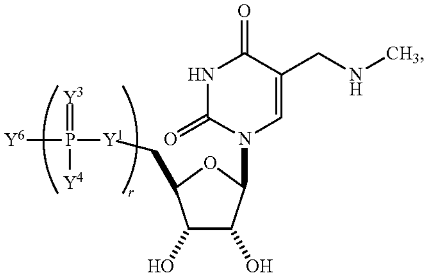
(BB-40)
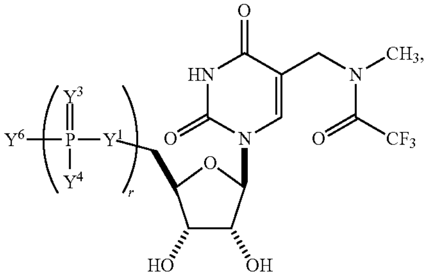
(BB-41)
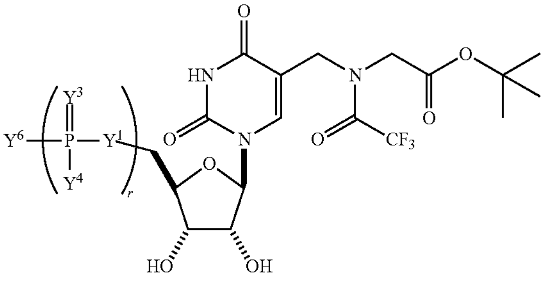
, -continued
(BB-42)
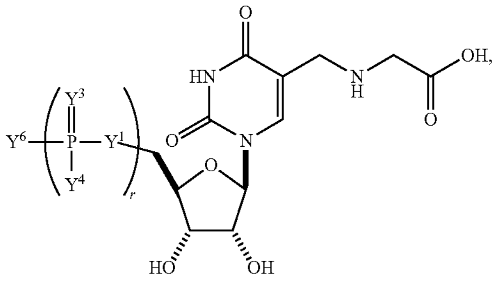
(BB-43)
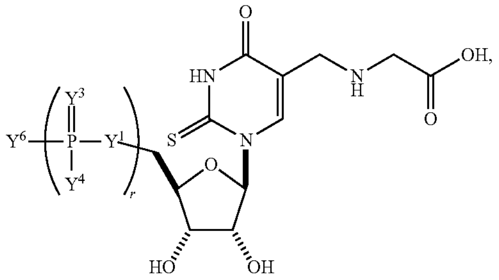
(BB-44)
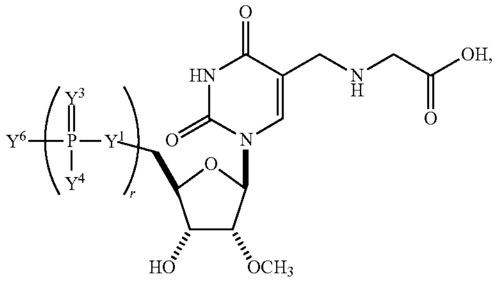
(BB-45)
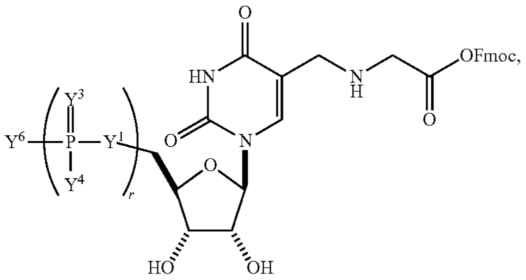
(BB-46)
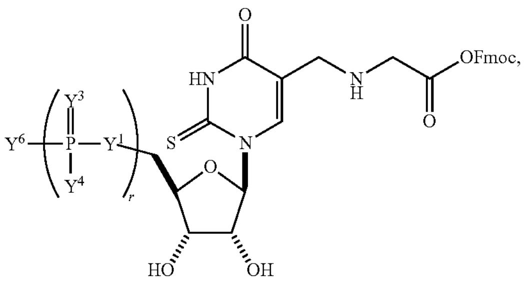
-continued
(BB-47)
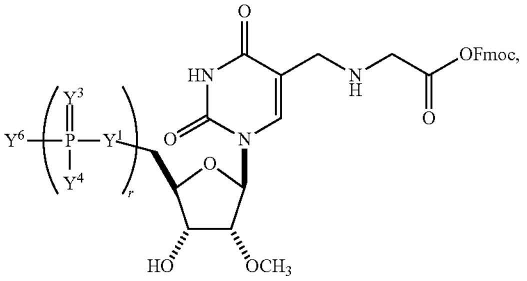
(BB-48)
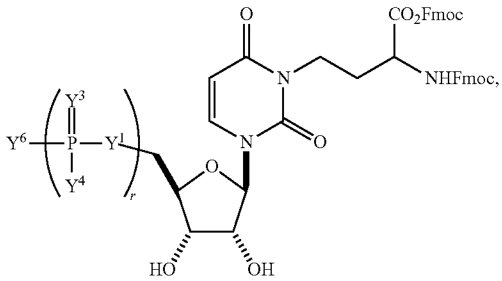
(BB-49)
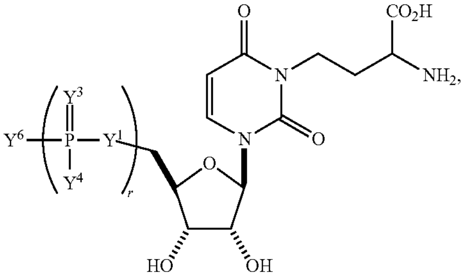
(BB-50)
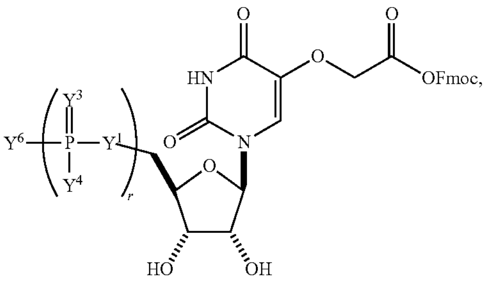
(BB-51)
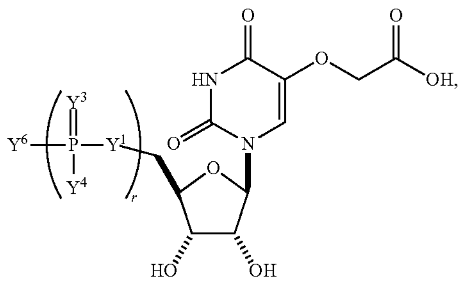

-continued
(BB-52)
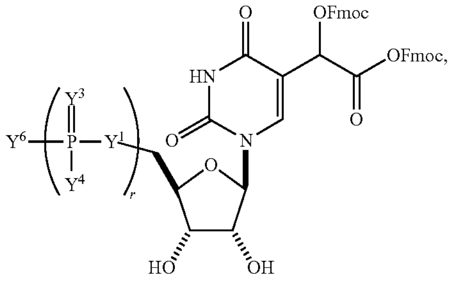
(BB-53)
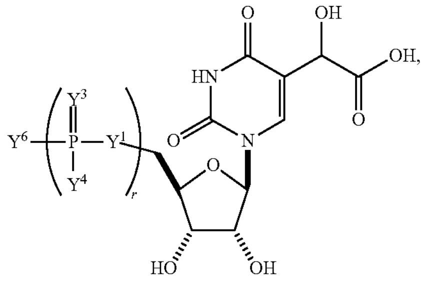
(BB-54)
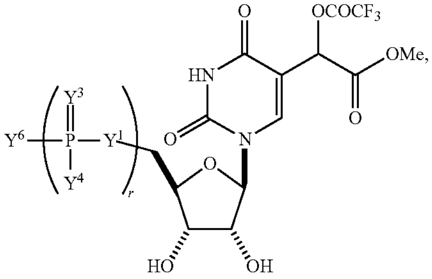
(BB-55)
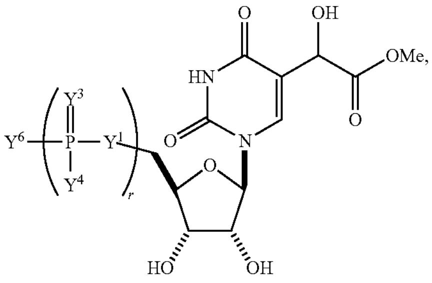
(BB-56)
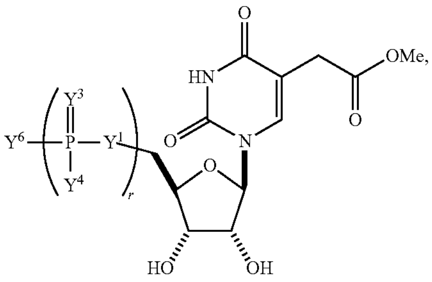
-continued
(BB-57)
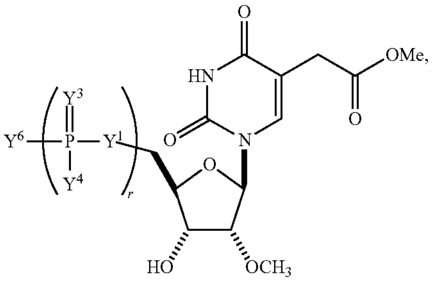
(BB-58)
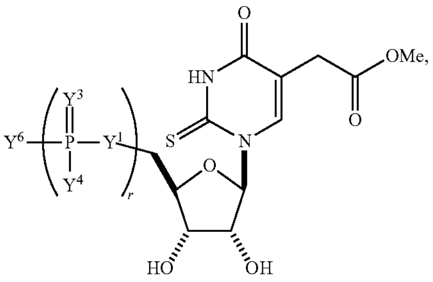
(BB-59)
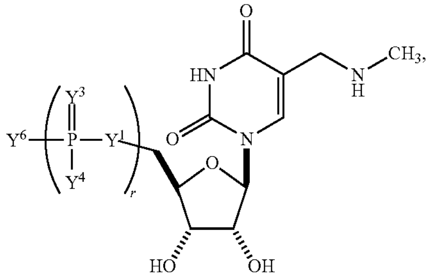
(BB-60)
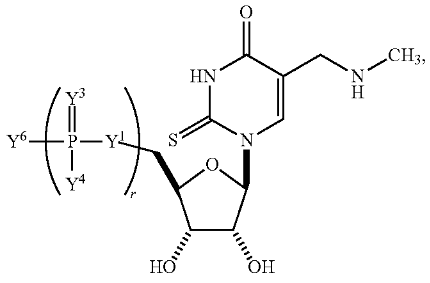
(BB-61)
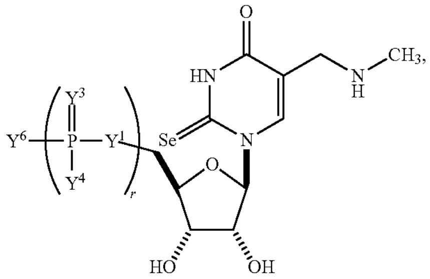

-continued
(BB-62)
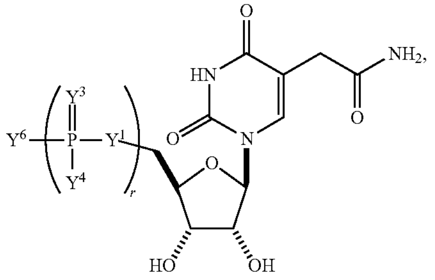
(BB-63)
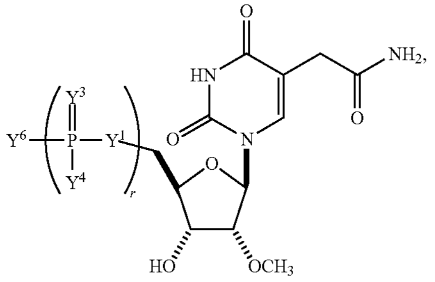
(BB-64)
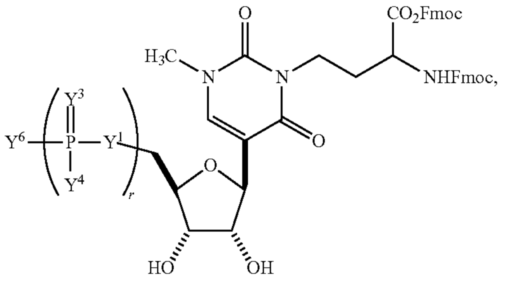
(BB-65)
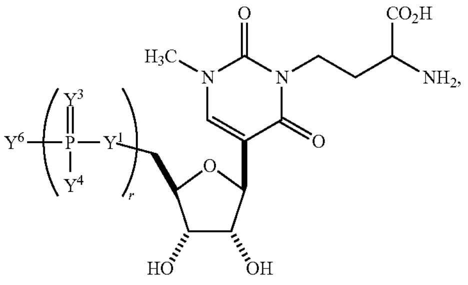
(BB-66)
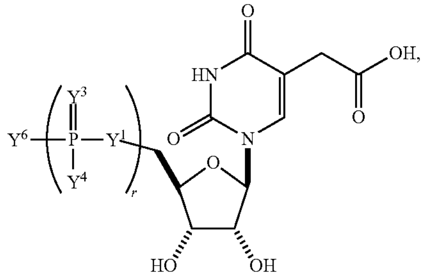
-continued
(BB-67)
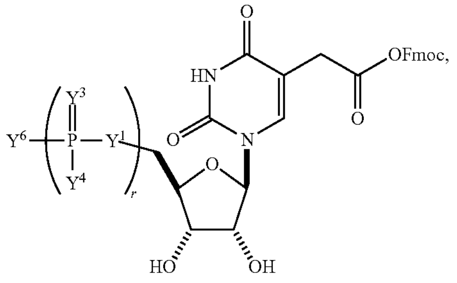
(BB-68)
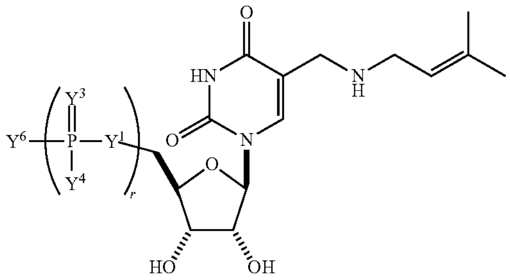
,
(BB-69)
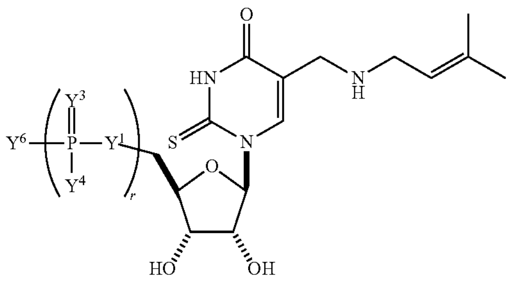
,
(BB-70)
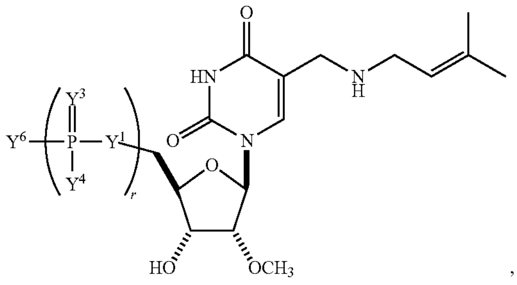
,
(BB-71)
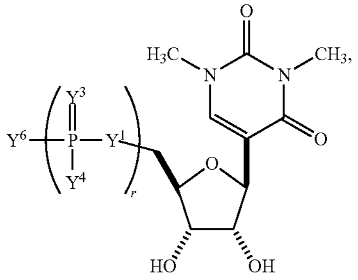

-continued
(BB-72)
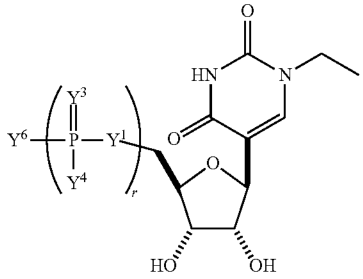
,
(BB-73)
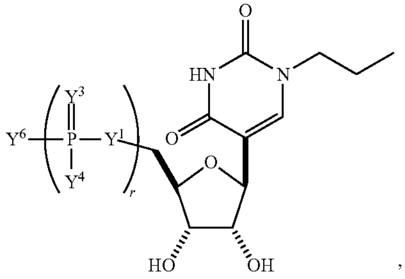
,
(BB-74)
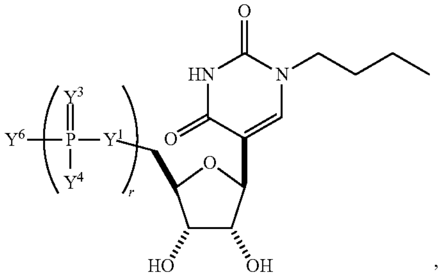
,
(BB-75)
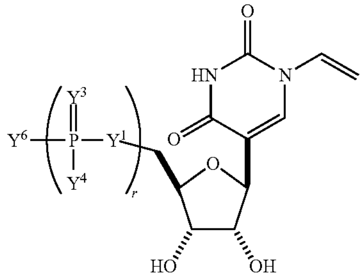
,
(BB-76)
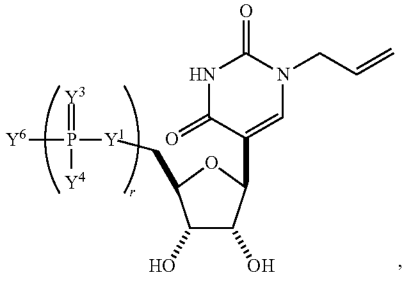
,
-continued
(BB-77)
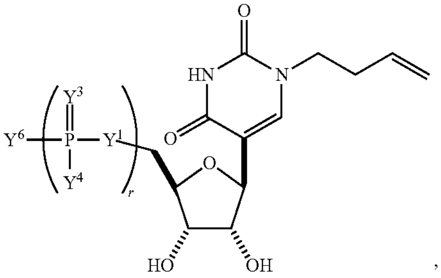
,
(BB-78)
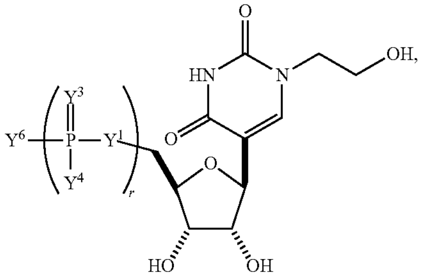
(BB-79)
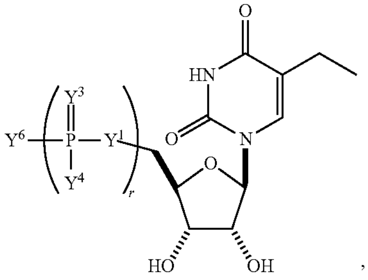
,
(BB-80)
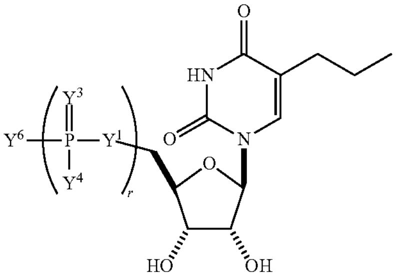
,
(BB-81)
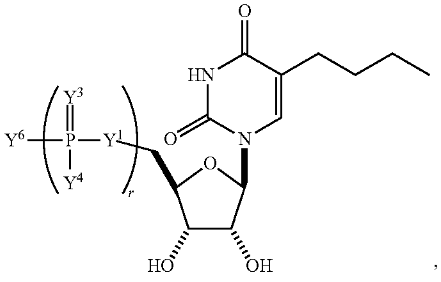
, -continued
(BB-82)
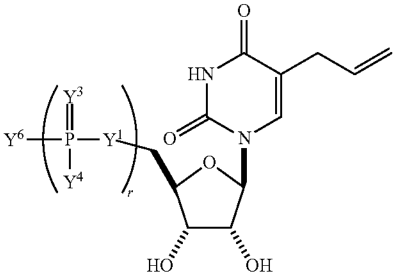
,
(BB-83)
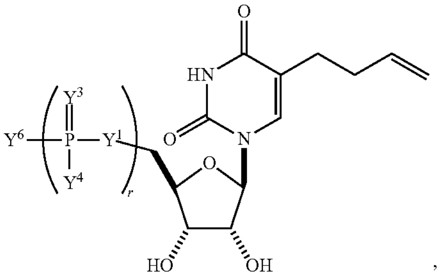
,
(BB-84)
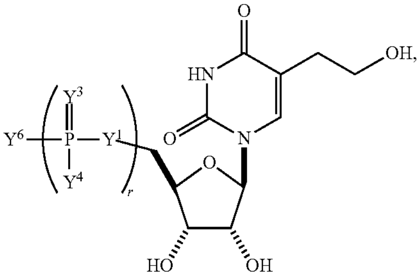
(BB-85)
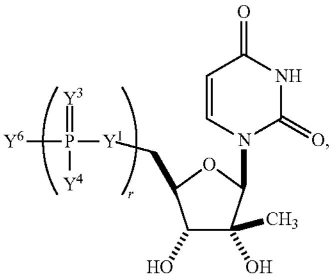
(BB-86)
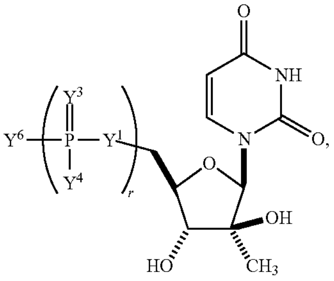
-continued
(BB-87)
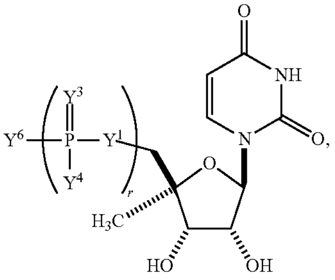
(BB-88)
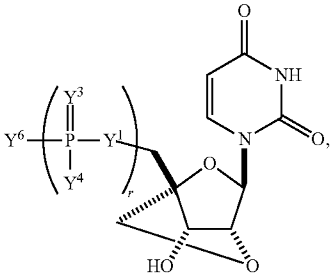
(BB-89)
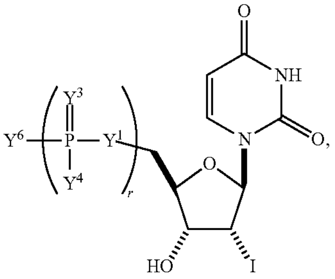
(BB-90)
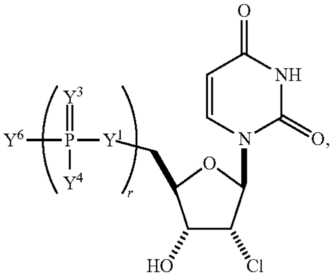
(BB-91)
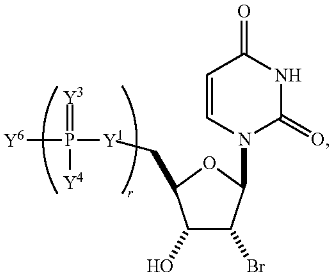

-continued
(BB-92)
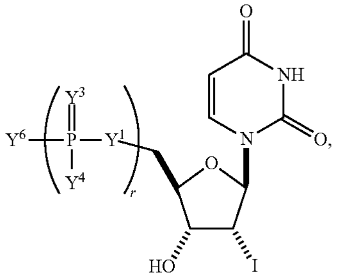
(BB-93)
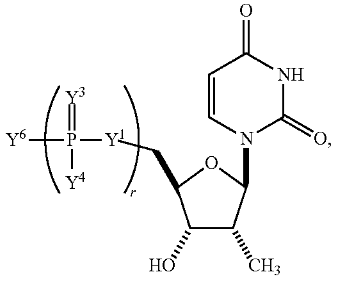
(BB-94)
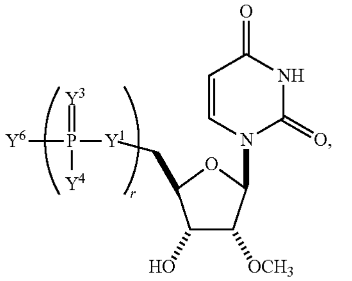
(BB-95)
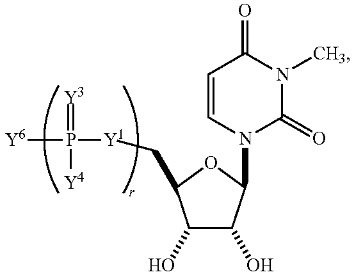
(BB-96)
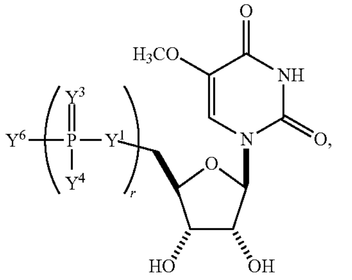
-continued
(BB-97)
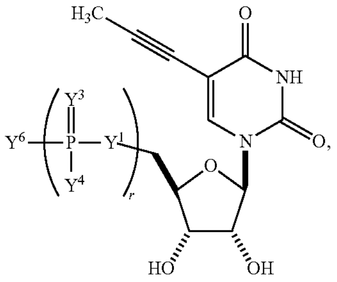
(BB-98)
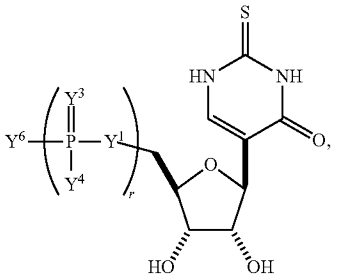
(BB-99)
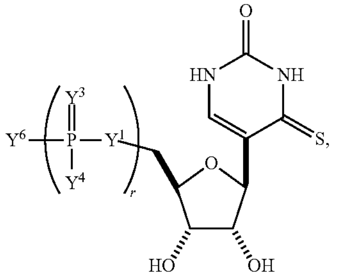
(BB-100)
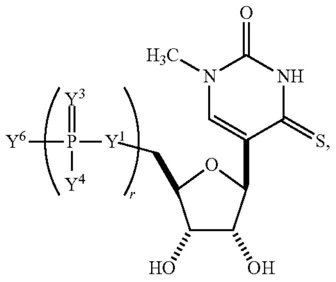
(BB-101)
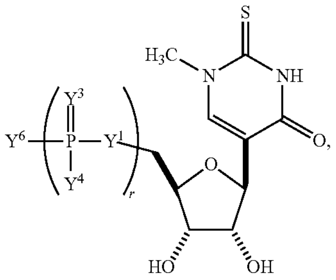

-continued
(BB-102)
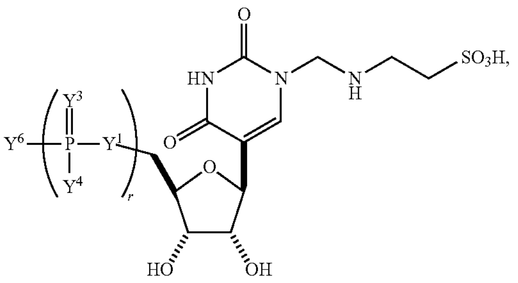
(BB-103)
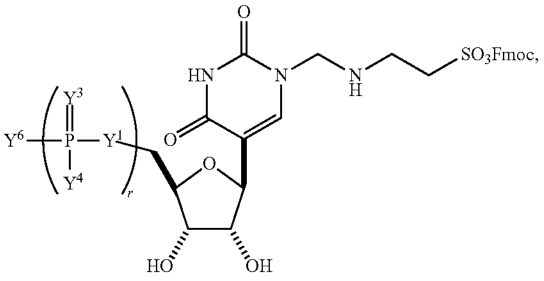
(BB-104)
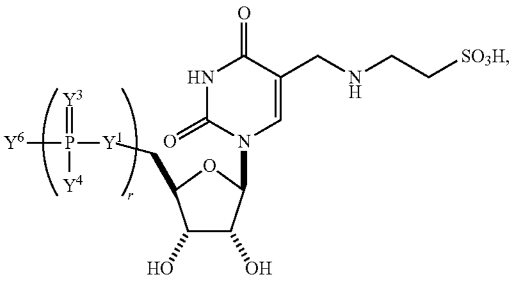
(BB-105)
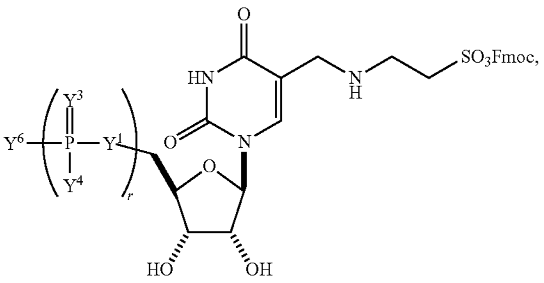
(BB-106)
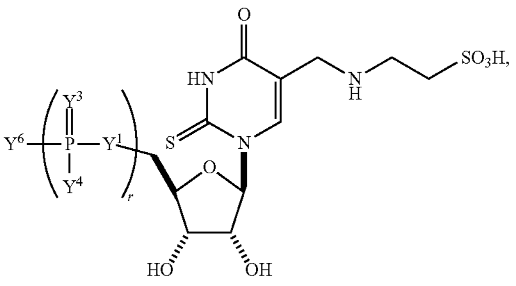
-continued
(BB-107)
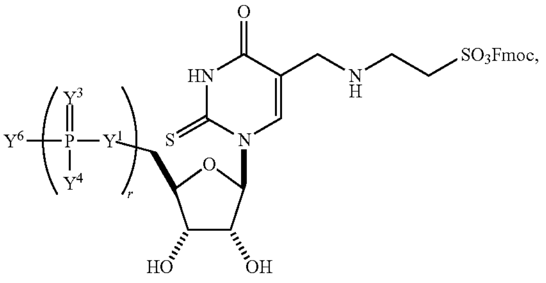
(BB-108)
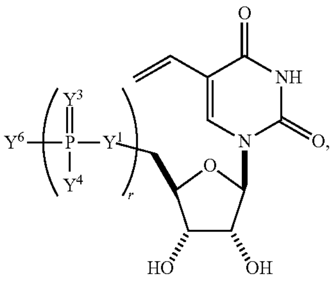
(BB-109)
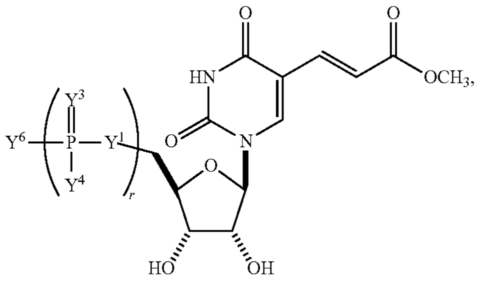
(BB-110)
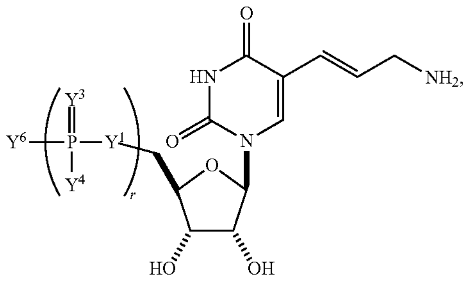
(BB-111)
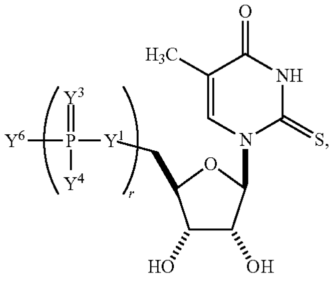

-continued
(BB-112)
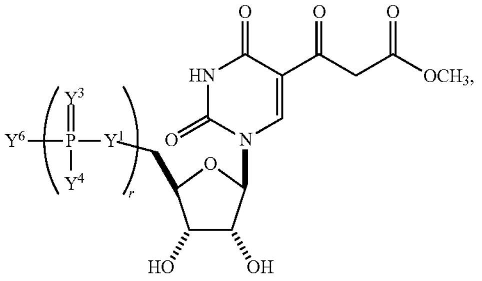
(BB-113)
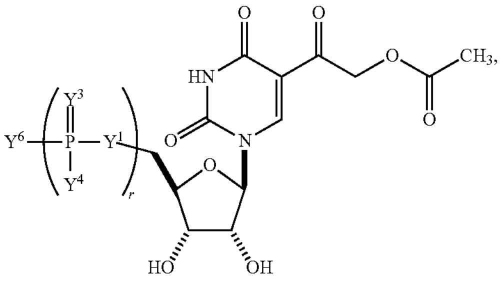
(BB-114)
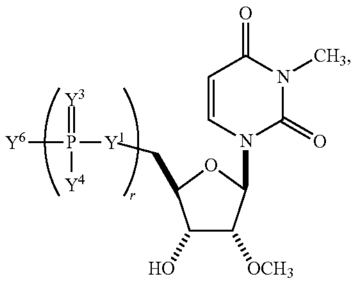
(BB-115)
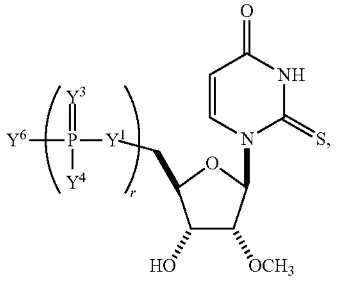
(BB-116)
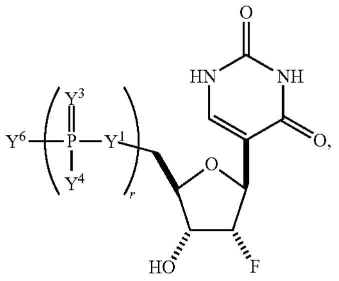
-continued
(BB-117)
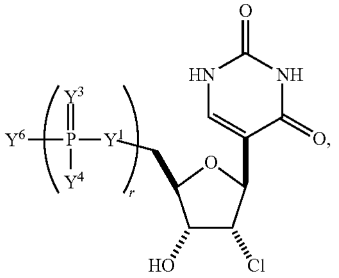
(BB-118)
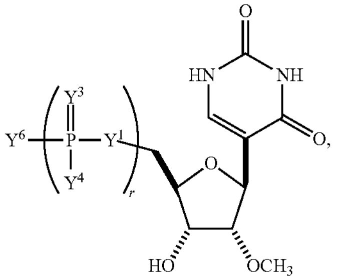
(BB-119)
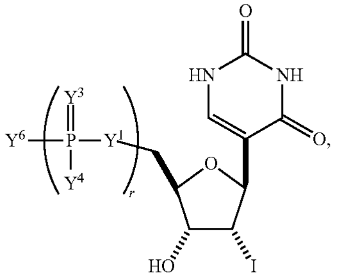
(BB-120)
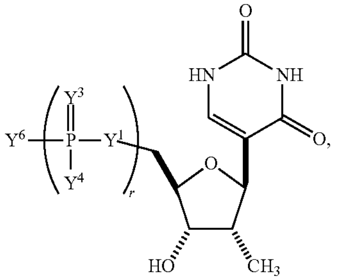
(BB-121)
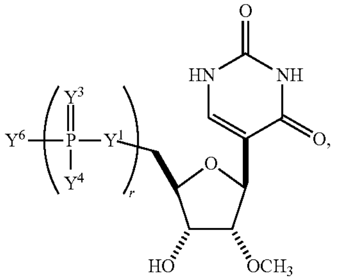

-continued (BB-122)

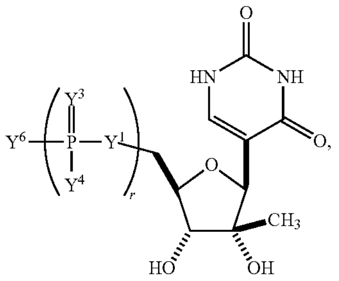

(BB-123)

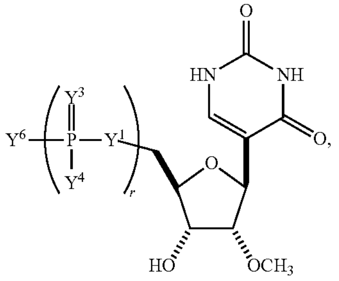

(BB-124)

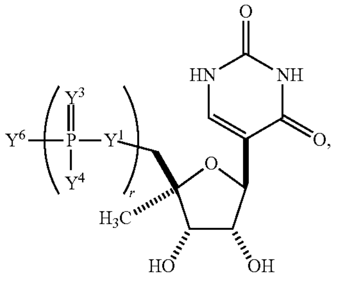

and (BB-125)

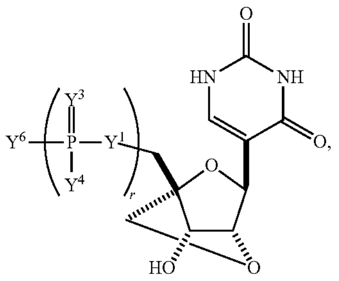

or a pharmaceutically acceptable salt or stereoisomer thereof, wherein Y1, Y3, Y4, Y6, and r are as described herein (e.g., each r is, independently, an integer from 0 to 5, such as from 0 to 3, from 1 to 3, or from 1 to 5)).

In some embodiments, the building block molecule, which may be incorporated into a polynucleotide, primary construct, or mmRNA, is a modified cytidine (e.g., selected from the group consisting of:

(BB-126)

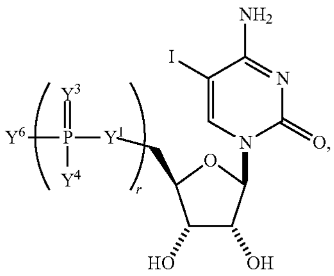

(BB-127)

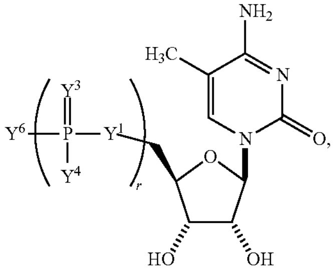

(BB-128)

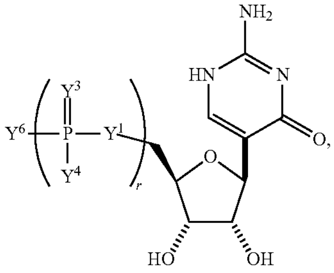

(BB-129)

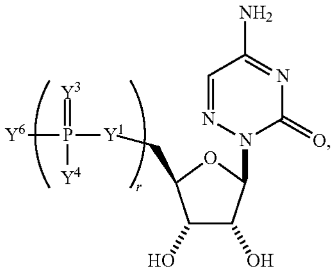

(BB-130)

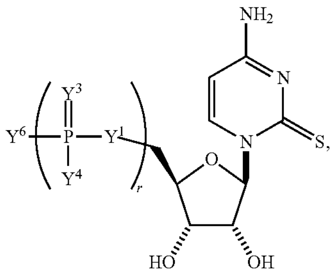

-continued
(BB-131)
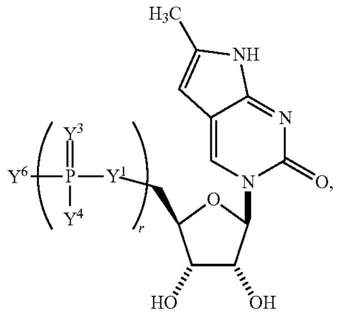
(BB-132)
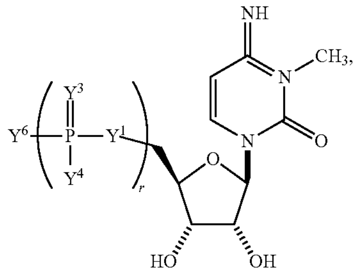
(BB-133)
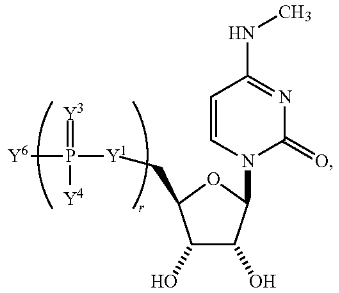
(BB-134)
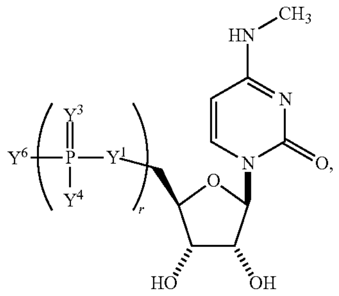
(BB-135)
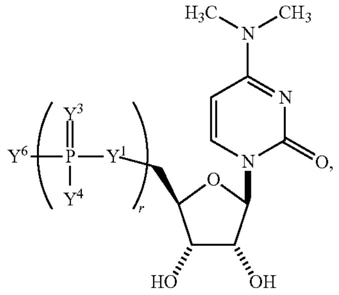
-continued
(BB-136)
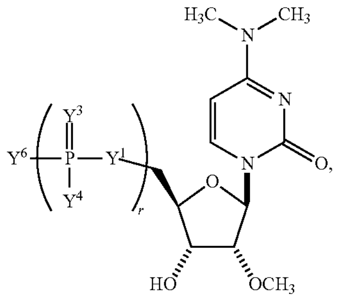
(BB-137)
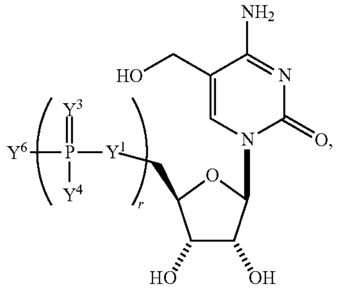
(BB-138)
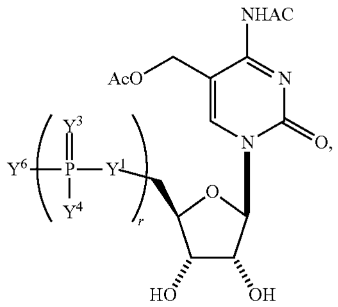
(BB-139)
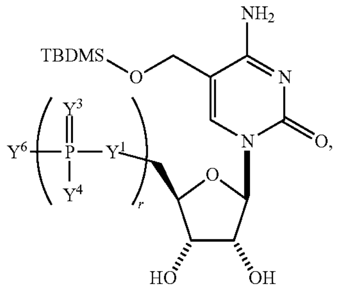
(BB-140)
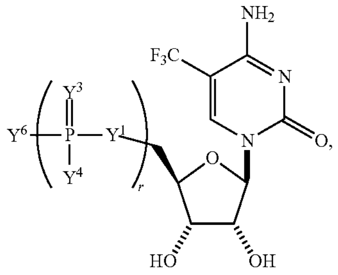

-continued
(BB-141)
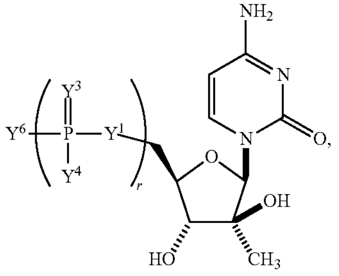
(BB-142)
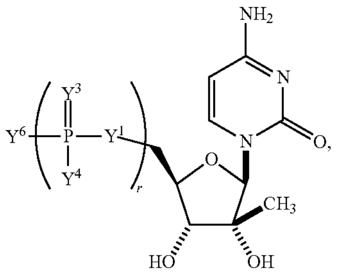
(BB-143)
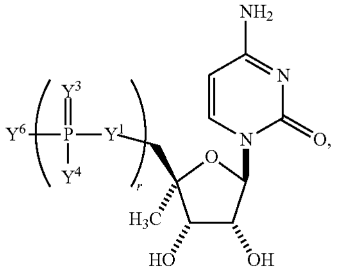
(BB-144)
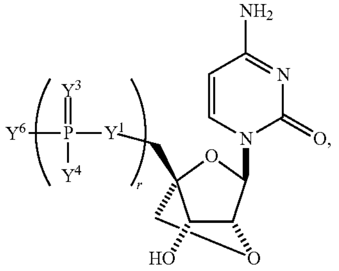
(BB-145)
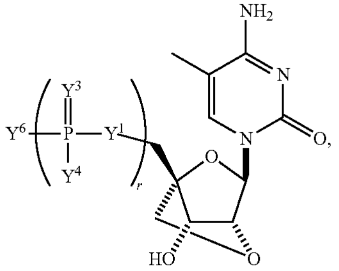
-continued
(BB-146)
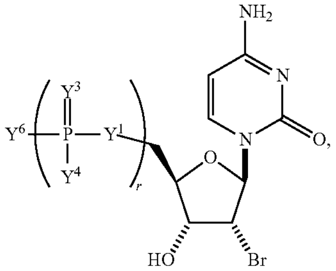
(BB-147)
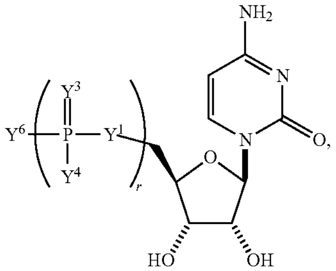
(BB-148)
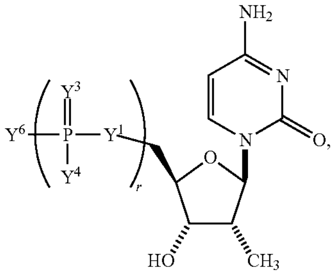
(BB-149)
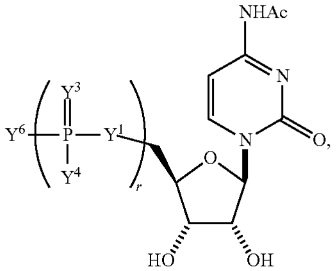
(BB-150)
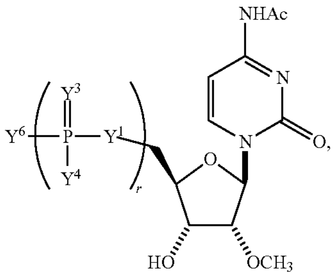

-continued
(BB-151)
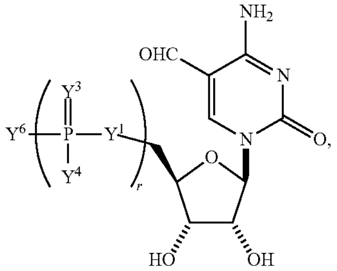
(BB-152)
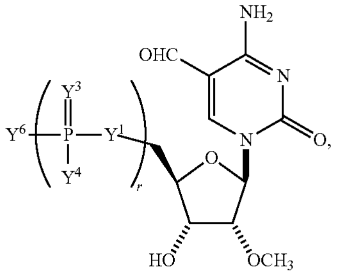
(BB-153)
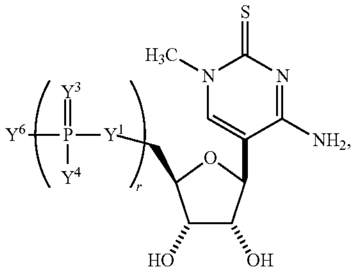
(BB-154)
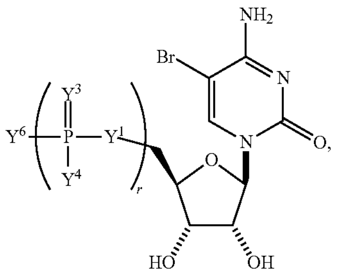
(BB-155)
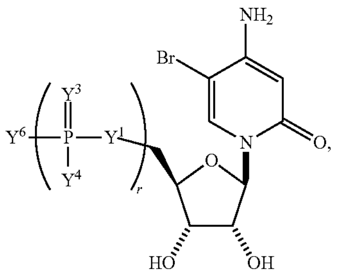
-continued
(BB-156)
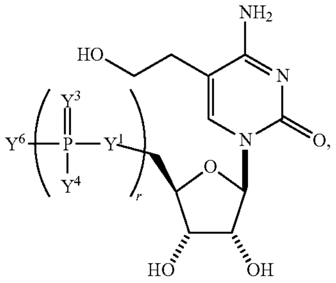
(BB-157)
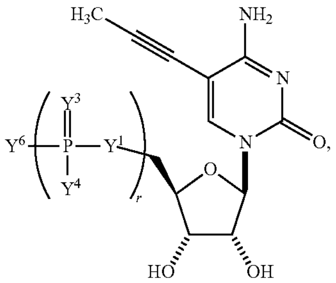
(BB-158)
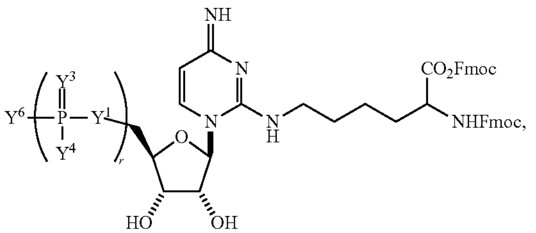
and
(BB-159)
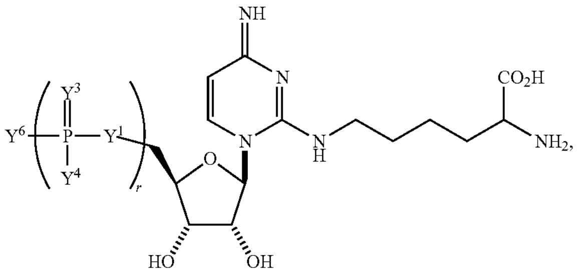
or a pharmaceutically acceptable salt or stereoisomer thereof, wherein Y1, Y3, Y4, Y6, and r are as described herein (e.g., each r is, independently, an integer from 0 to 5, such as from 0 to 3, from 1 to 3, or from 1 to 5)). For example, the building block molecule, which may be incorporated into a polynucleotide, primary construct, or mmRNA, can be:

(BB-160)

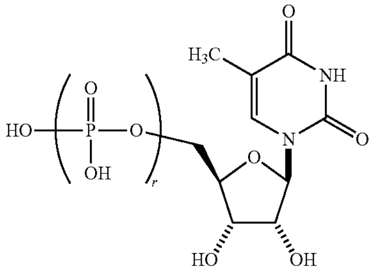

or (BB-161)

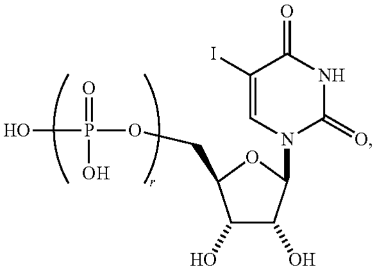

or a pharmaceutically acceptable salt or stereoisomer thereof, wherein each r is, independently, an integer from 0 to 5 (e.g., from 0 to 3, from 1 to 3, or from 1 to 5).

In some embodiments, the building block molecule, which may be incorporated into a polynucleotide, primary construct, or mmRNA, is a modified adenosine (e.g., selected from the group consisting of:

(BB-162)

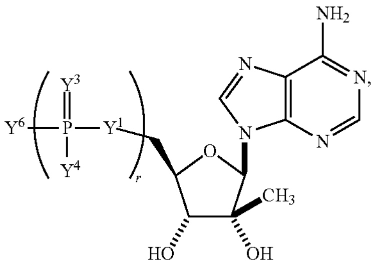

(BB-163)

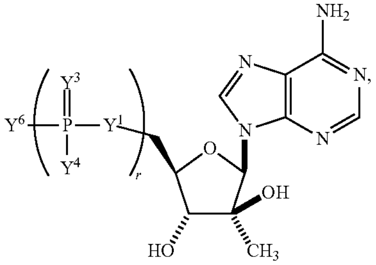

(BB-164)

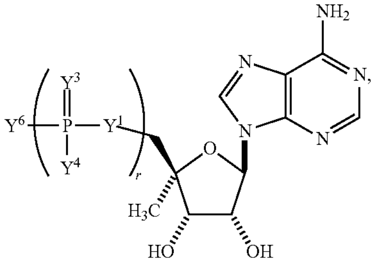

-continued (BB-165)

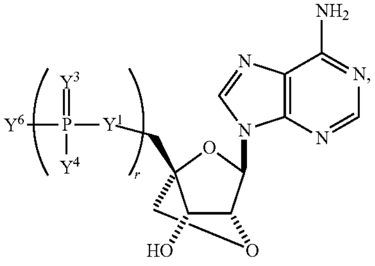

(BB-166)

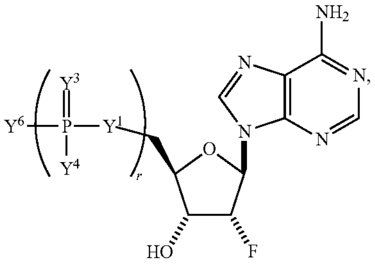

(BB-167)

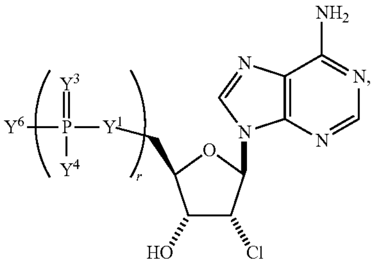

(BB-168)

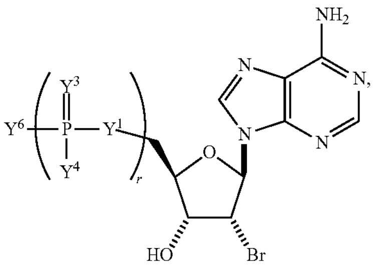

(BB-169)

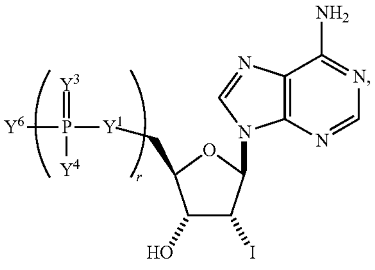

(BB-170)

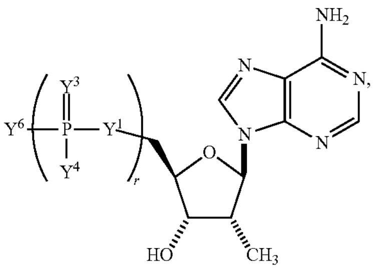

-continued
(BB-171)
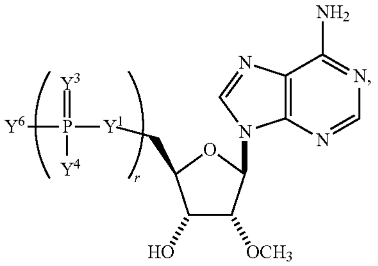
(BB-172)
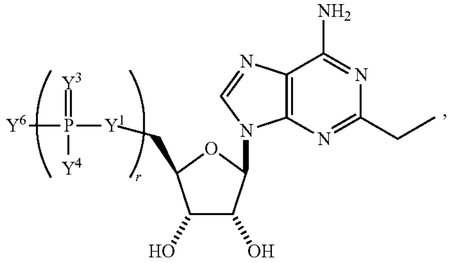
(BB-173)
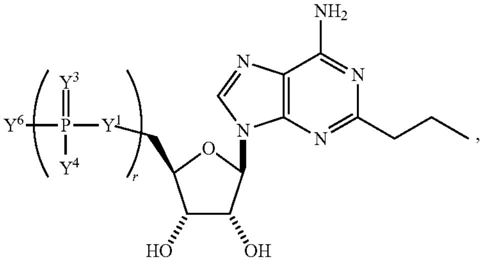
(BB-174)
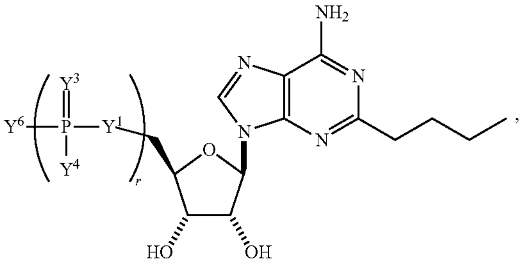
(BB-175)
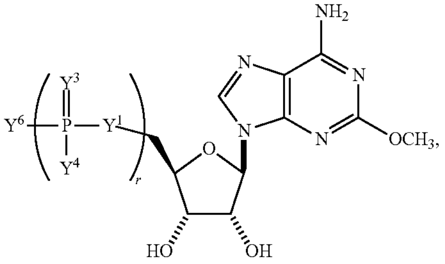
(BB-176)
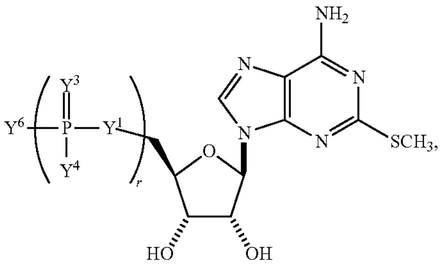
(BB-177)
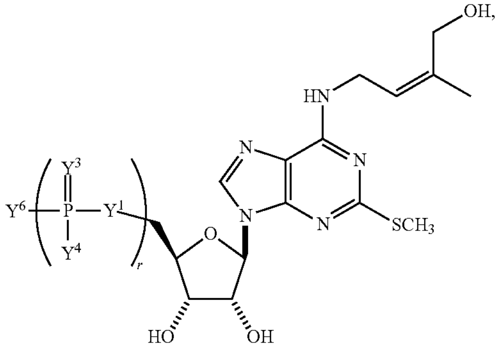
(BB-178)
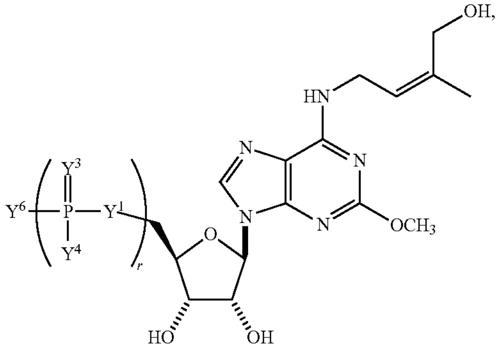
(BB-179)
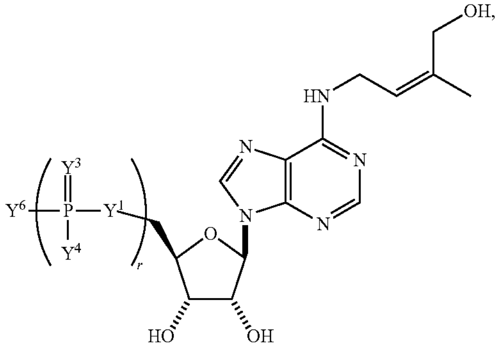
(BB-180)
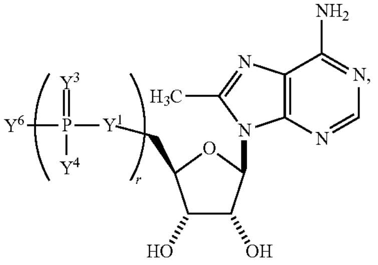

-continued
(BB-181)
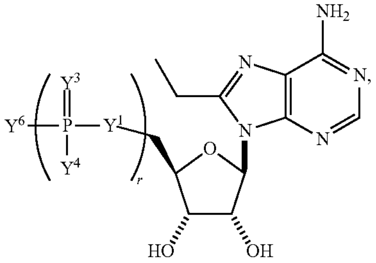
(BB-182)
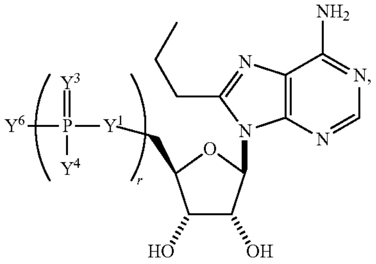
(BB-183)
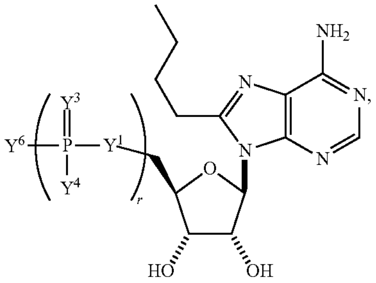
(BB-184)
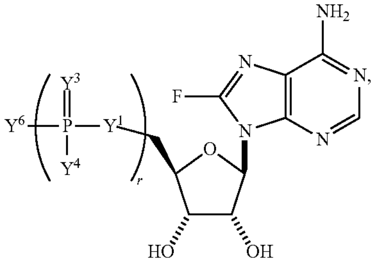
(BB-185)
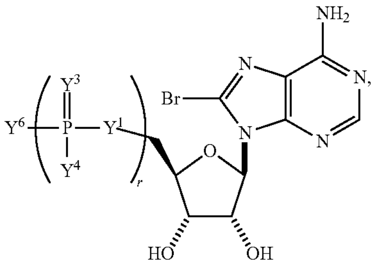
(BB-186)
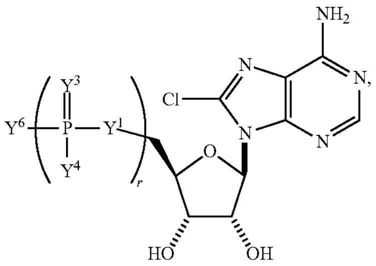
-continued
(BB-187)
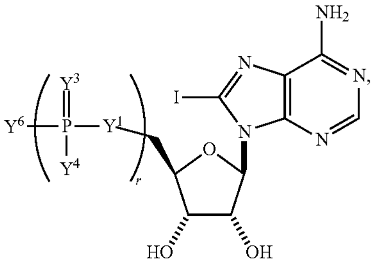
(BB-188)
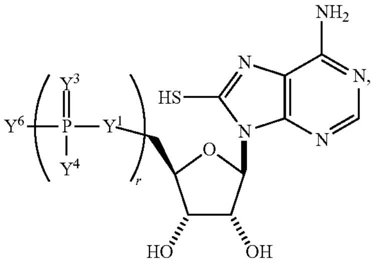
(BB-189)
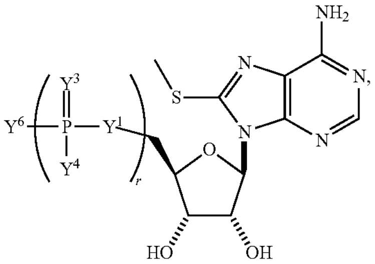
(BB-190)
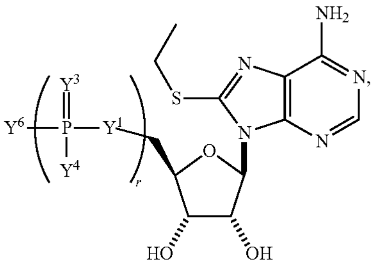
(BB-191)
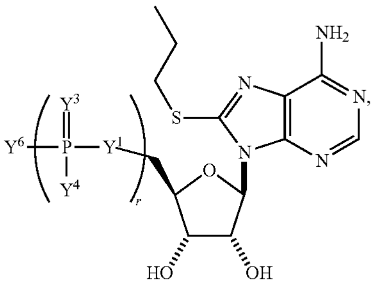

-continued (BB-192)

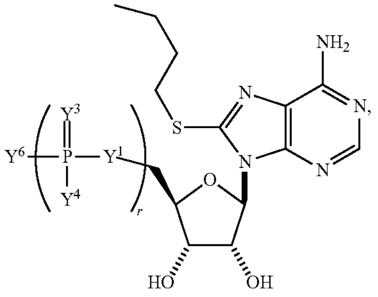

(BB-193)

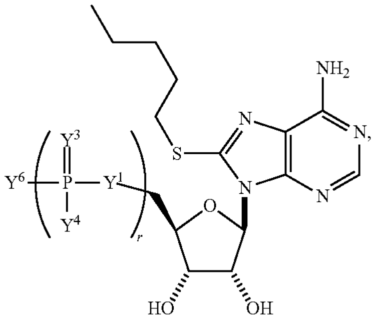

(BB-194)

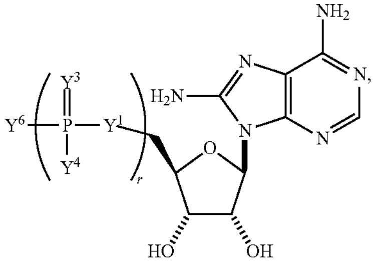

(BB-195)

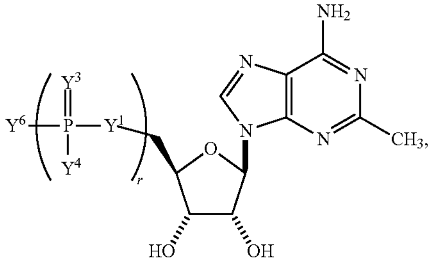

(BB-196)

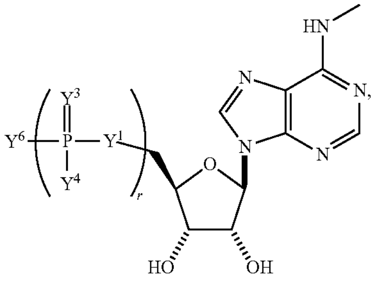

-continued (BB-197)

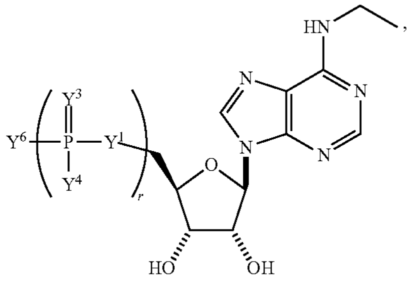

(BB-198)

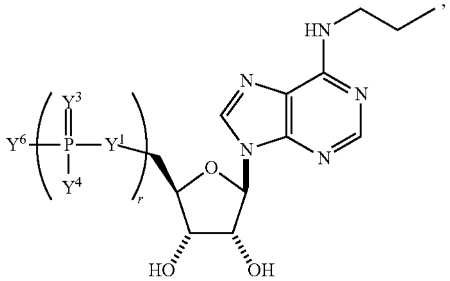

(BB-199)

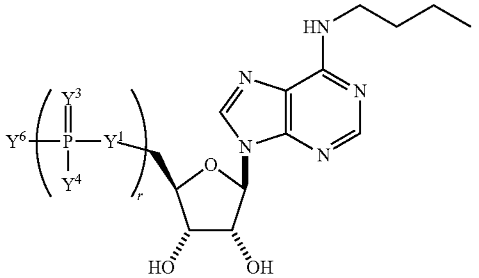

and (BB-200)

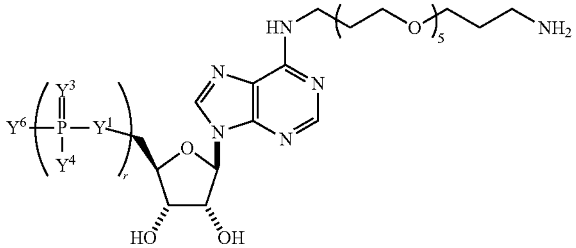

or a pharmaceutically acceptable salt or stereoisomer thereof, wherein Y1, Y3, Y4, Y6, and r are as described herein (e.g., each r is, independently, an integer from 0 to 5, such as from 0 to 3, from 1 to 3, or from 1 to 5)).

In some embodiments, the building block molecule, which may be incorporated into a polynucleotide, primary construct, or mmRNA, is a modified guanosine (e.g., selected from the group consisting of:

-continued
(BB-201)
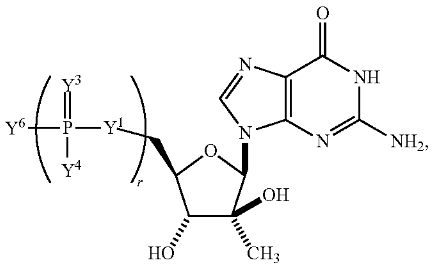
(BB-202)
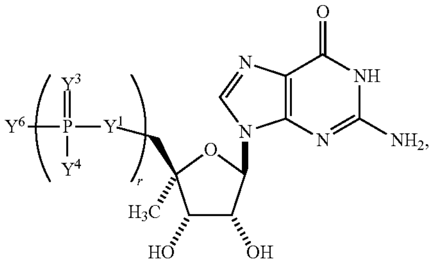
(BB-203)
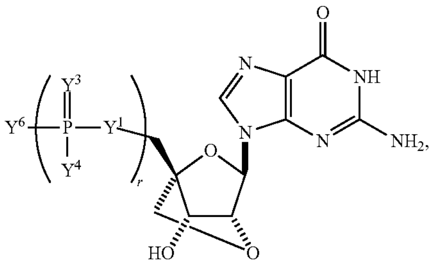
(BB-204)
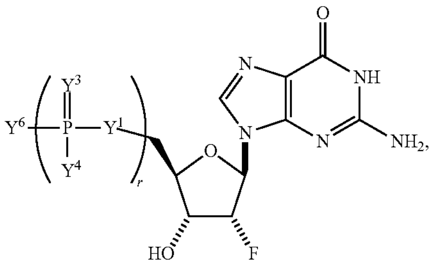
(BB-205)
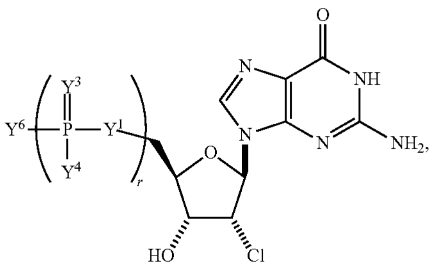
(BB-206)
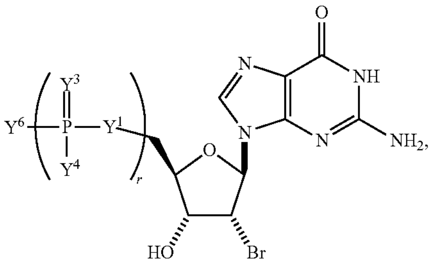
(BB-207)
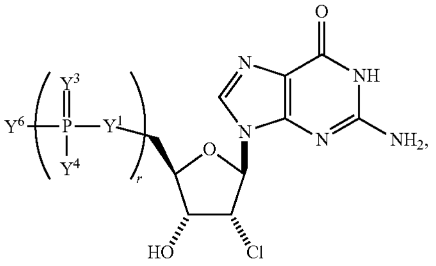
(BB-208)
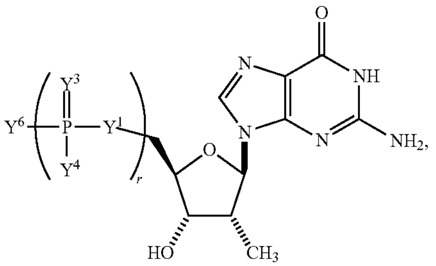
(BB-209)
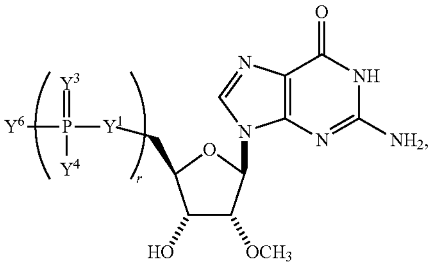
(BB-210)
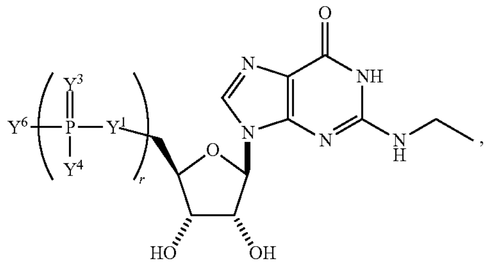

-continued
(BB-211)
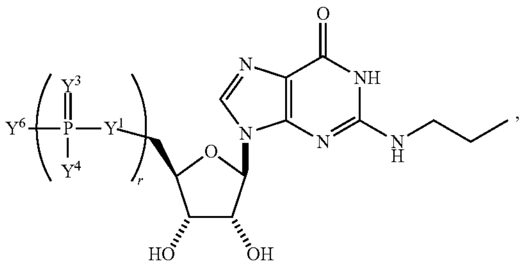
(BB-212)
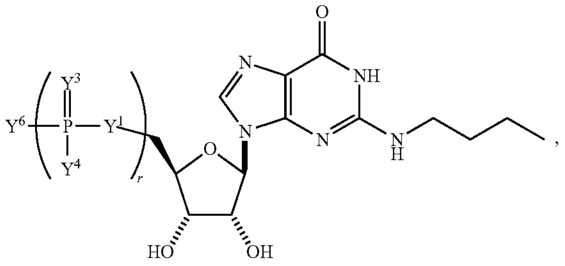
(BB-213)
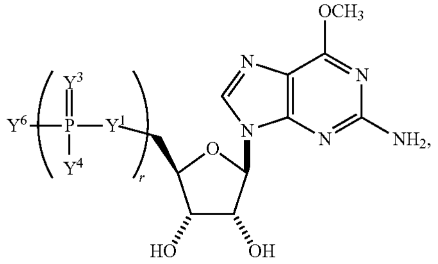
(BB-214)
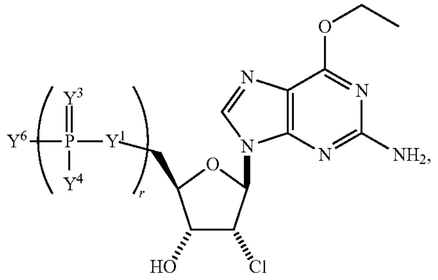
(BB-215)
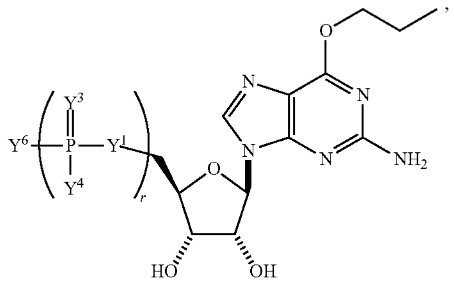
-continued
(BB-216)
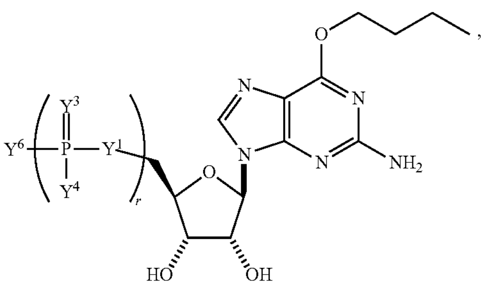
(BB-217)
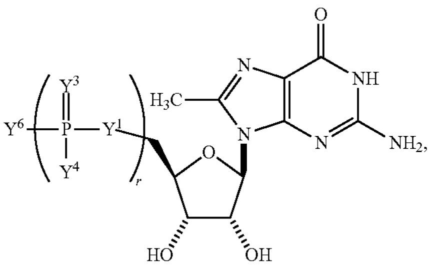
(BB-218)
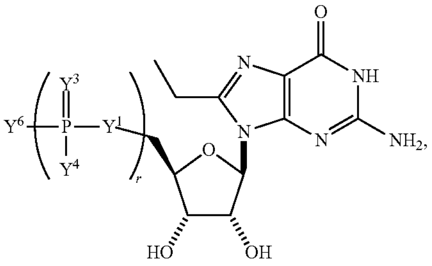
(BB-219)
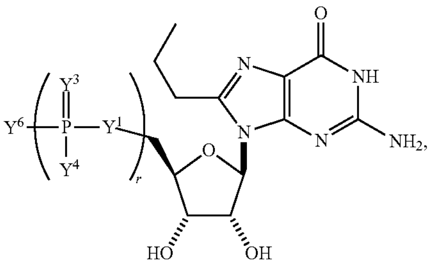
(BB-220)
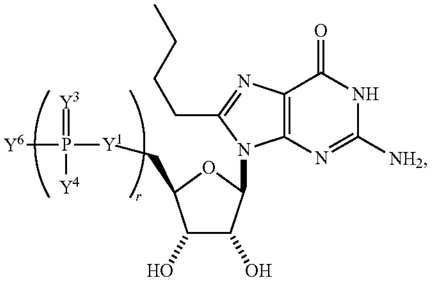

-continued
(BB-221)
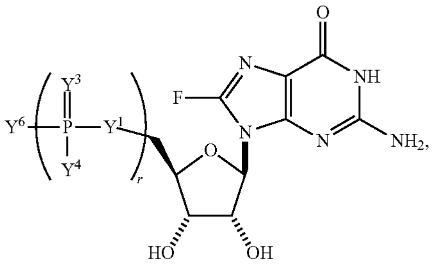
(BB-222)
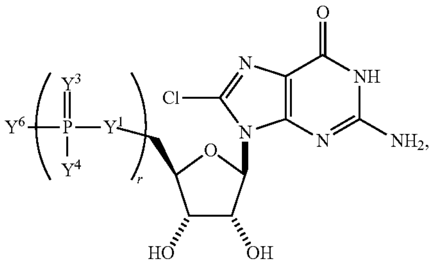
(BB-223)
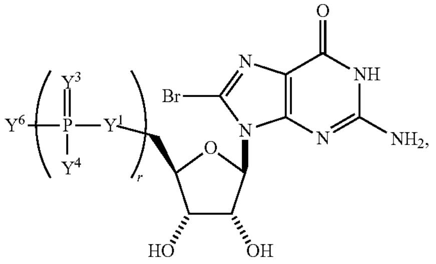
(BB-224)
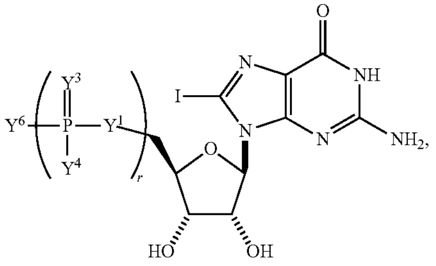
(BB-225)
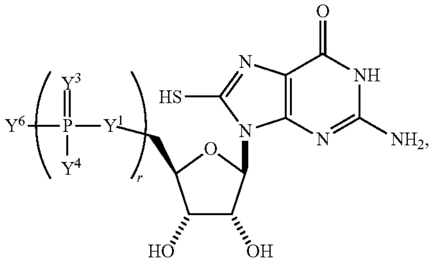
-continued
(BB-226)
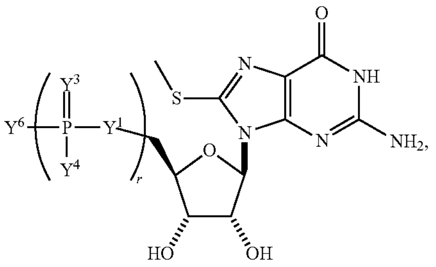
(BB-227)
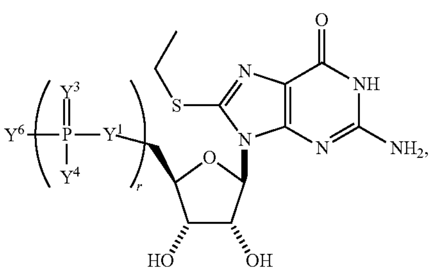
(BB-228)
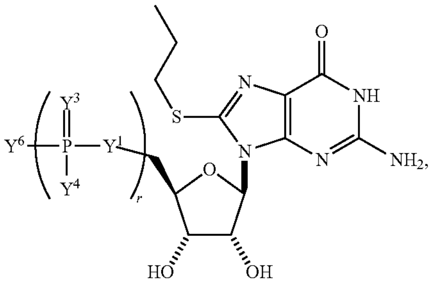
(BB-229)
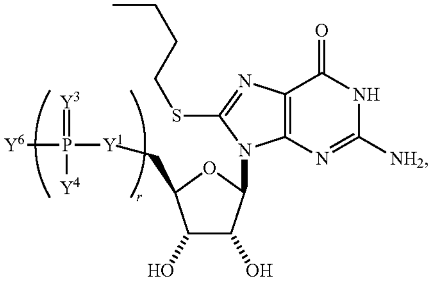
(BB-230)
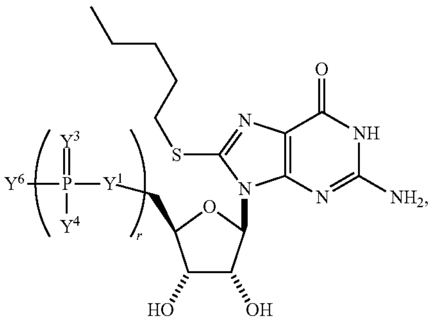

-continued (BB-231)

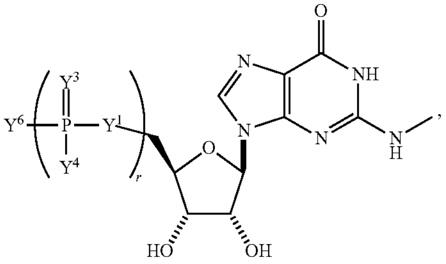

(BB-232)

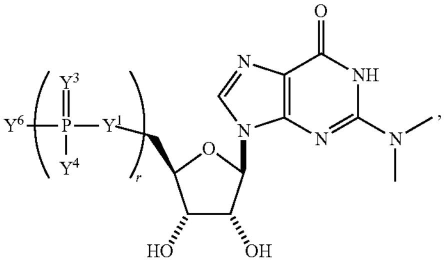

(BB-233)

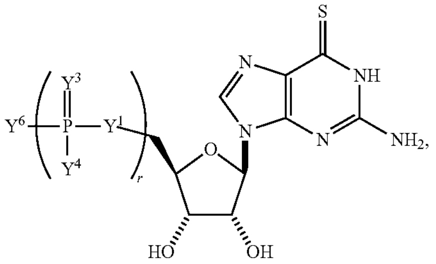

(BB-234)

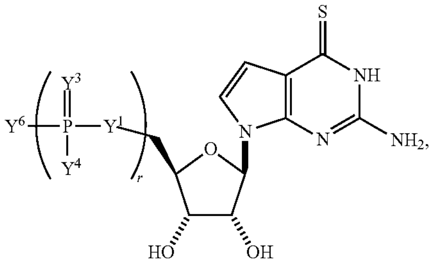

(BB-235)

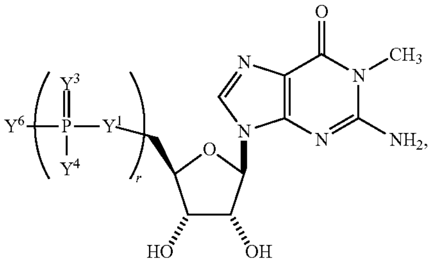

and

-continued (BB-236)

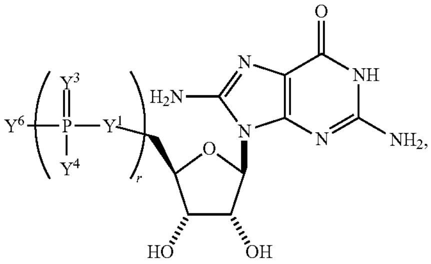

or a pharmaceutically acceptable salt or stereoisomer thereof, wherein Y1, Y3, Y4, Y6, and r are as described herein (e.g., each r is, independently, an integer from 0 to 5, such as from 0 to 3, from 1 to 3, or from 1 to 5)).

In some embodiments, the chemical modification can include replacement of C group at C-5 of the ring (e.g., for a pyrimidine nucleoside, such as cytosine or uracil) with N (e.g., replacement of the >CH group at C-5 with >NRN1 group, wherein RN1 is H or optionally substituted alkyl). For example, the building block molecule, which may be incorporated into a polynucleotide, primary construct, or mmRNA, can be:

(BB-237)

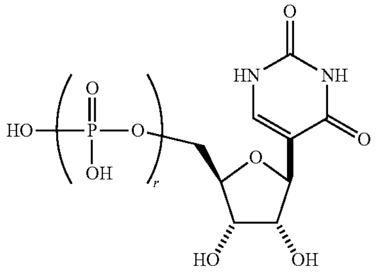

or (BB-238)

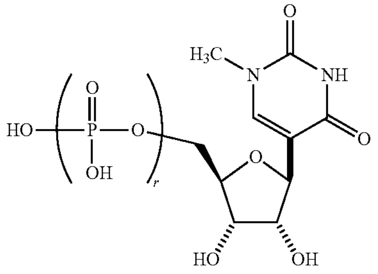

or (BB-239)

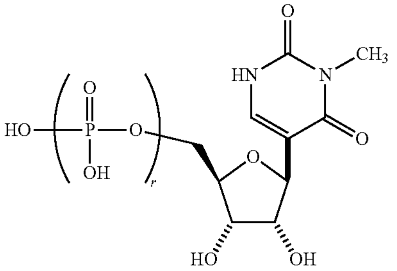

or

-continued (BB-240)

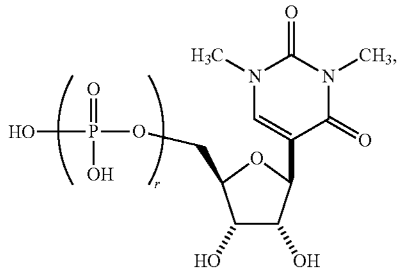

or a pharmaceutically acceptable salt or stereoisomer thereof, wherein each r is, independently, an integer from 0 to 5 (e.g., from 0 to 3, from 1 to 3, or from 1 to 5).

In another embodiment, the chemical modification can include replacement of the hydrogen at C-5 of cytosine with halo (e.g., Br, Cl, F, or I) or optionally substituted alkyl (e.g., methyl). For example, the building block molecule, which may be incorporated into a polynucleotide, primary construct, or mmRNA, can be:

(BB-241)

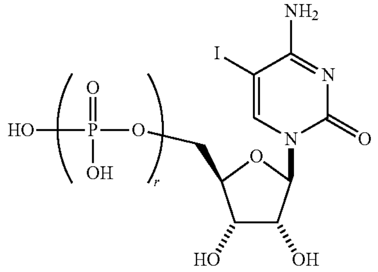

or (BB-242)

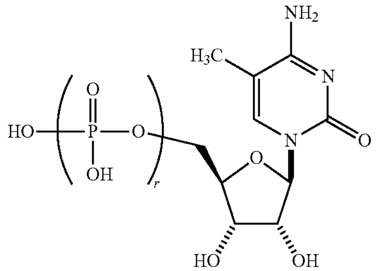

or (BB-243)

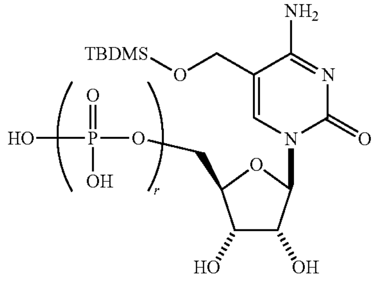

or

-continued (BB-244)

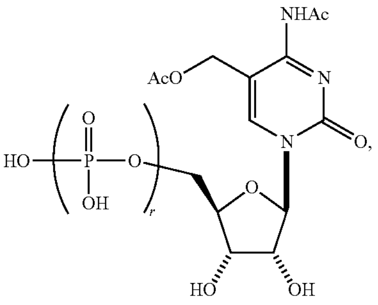

or a pharmaceutically acceptable salt or stereoisomer thereof, wherein each r is, independently, an integer from 0 to 5 (e.g., from 0 to 3, from 1 to 3, or from 1 to 5).

In yet a further embodiment, the chemical modification can include a fused ring that is formed by the NH2 at the C-4 position and the carbon atom at the C-5 position. For example, the building block molecule, which may be incorporated into a polynucleotide, primary construct, or mmRNA, can be:

(BB-245)

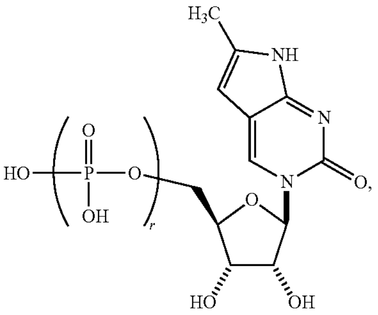

or a pharmaceutically acceptable salt or stereoisomer thereof, wherein each r is, independently, an integer from 0 to 5 (e.g., from 0 to 3, from 1 to 3, or from 1 to 5).

Modifications on the Sugar

The modified nucleosides and nucleotides (e.g., building block molecules), which may be incorporated into a polynucleotide, primary construct, or mmRNA (e.g., RNA or mRNA, as described herein), can be modified on the sugar of the ribonucleic acid. For example, the 2' hydroxyl group (OH) can be modified or replaced with a number of different substituents. Exemplary substitutions at the 2'-position include, but are not limited to, H, halo, optionally substituted C1-6 alkyl; optionally substituted C1-6 alkoxy; optionally substituted C6-10 aryloxy; optionally substituted C3-8 cycloalkyl; optionally substituted C3-8 cycloalkoxy; optionally substituted C6-10 aryloxy; optionally substituted C6-10 aryl-C1-6 alkoxy, optionally substituted C1-12 (heterocyclyl)oxy; a sugar (e.g., ribose, pentose, or any described herein); a polyethyleneglycol (PEG), —O(CH2CH2O)nCH2CH2OR, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); “locked” nucleic acids (LNA) in which the 2'-hydroxyl is connected by a C1-6 alkylene or C1-6 heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3 '→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide, primary construct, or mmRNA molecule can include nucleotides containing, e.g., arabinose, as the sugar.

Modifications on the Nucleobase

The present disclosure provides for modified nucleosides and nucleotides. As described herein "nucleoside" is defined as a compound containing a sugar molecule (e.g., a pentose or ribose) or a derivative thereof in combination with an organic base (e.g., a purine or pyrimidine) or a derivative thereof (also referred to herein as "nucleobase"). As described herein, "nucleotide" is defined as a nucleoside including a phosphate group. The modified nucleotides may by synthesized by any useful method, as described herein (e.g., chemically, enzymatically, or recombinantly to include one or more modified or non-natural nucleosides).

The modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil.

The modified nucleosides and nucleotides can include a modified nucleobase. Examples of nucleobases found in RNA include, but are not limited to, adenine, guanine, cytosine, and uracil. Examples of nucleobase found in DNA include, but are not limited to, adenine, guanine, cytosine, and thymine. These nucleobases can be modified or wholly replaced to provide polynucleotides, primary constructs, or mmRNA molecules having enhanced properties, e.g., resistance to nucleases through disruption of the binding of a major groove binding partner. Table 8 below identifies the chemical faces of each canonical nucleotide. Circles identify the atoms comprising the respective chemical regions.

TABLE 8

| Major Groove Face | Minor Groove Face | Watson-Crick Base-pairing Face |
|---|---|---|
| | Pyrimidines Cytidine: | |
| 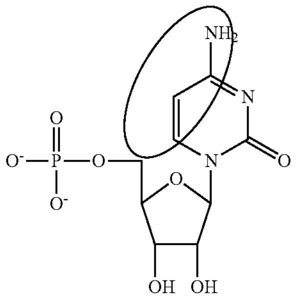 [SMILES: Nc1ccn(C2OC(COP(=O)([O-])[O-])C(O)C2O)c(=O)n1] | 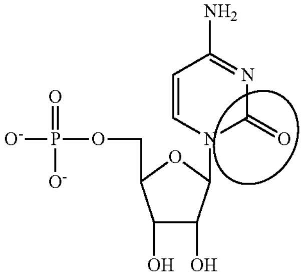 | 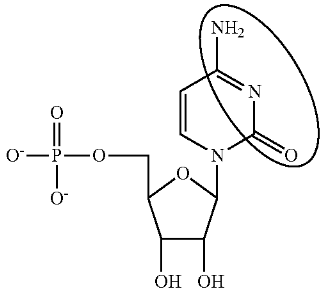 [SMILES: Nc1ccn(C2OC(COP(=O)([O-])[O-])C(O)C2O)c(=O)n1] |
| | Uridine: | |
| 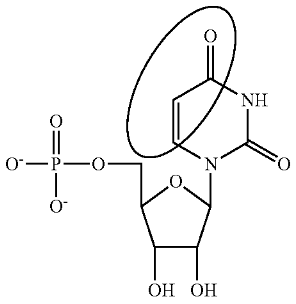 [SMILES: O=c1ccn(C2OC(COP(=O)([O-])[O-])C(O)C2O)c(=O)[nH]1] | 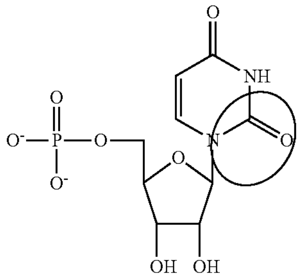 [SMILES: O=c1ccn(C2OC(COP(=O)([O-])[O-])C(O)C2O)c(=O)[nH]1] | 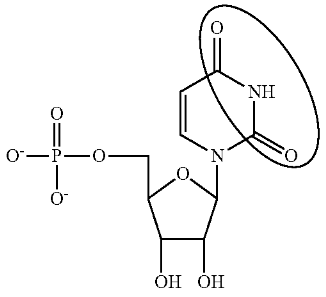 [SMILES: O=c1ccn(C2OC(COP(=O)([O-])[O-])C(O)C2O)c(=O)[nH]1] |

TABLE 8-continued

| Major Groove Face | Minor Groove Face | Watson-Crick Base-pairing Face |
|---|---|---|
| | Purines Adenosine: | |
| 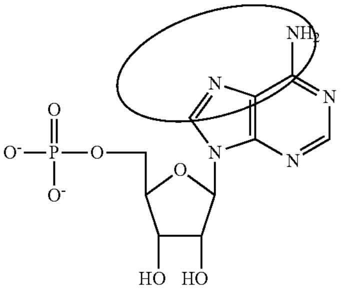 [SMILES: Nc1ncnc2c1ncn2C1OC(COP(=O)([O-])[O-])C(O)C1O] | 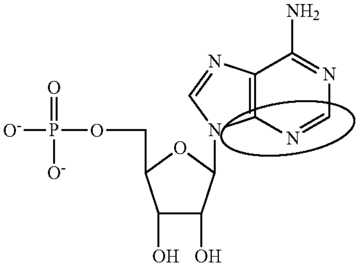 [SMILES: Nc1ncnc2c1ncn2C1OC(COP(=O)([O-])[O-])C(O)C1O] | 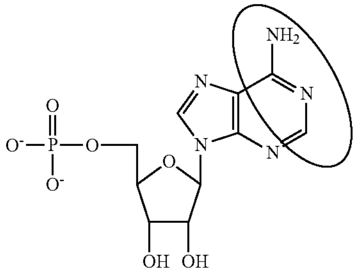 [SMILES: Nc1ncnc2c1ncn2C1OC(COP(=O)([O-])[O-])C(O)C1O] |
| | Guanosine: | |
| 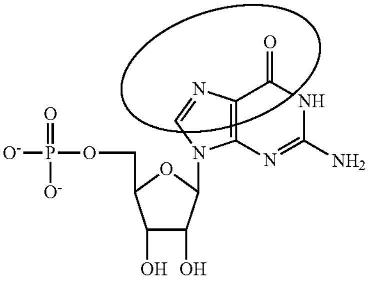 [SMILES: Nc1nc2c(ncn2C2OC(COP(=O)([O-])[O-])C(O)C2O)c(=O)[nH]1] | 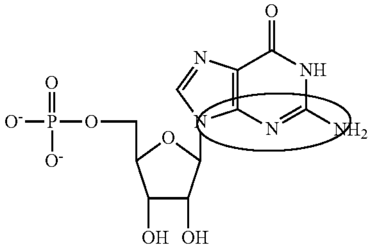 [SMILES: Nc1nc2c(ncn2C2OC(COP(=O)([O-])[O-])C(O)C2O)c(=O)[nH]1] | 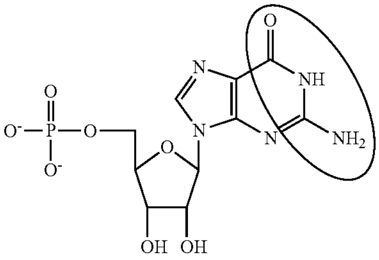 [SMILES: Nc1nc2c(ncn2C2OC(COP(=O)([O-])[O-])C(O)C2O)c(=O)[nH]1] |

In some embodiments, B is a modified uracil. Exemplary modified uracils include those having Formula (b1)-(b5):

(b1)

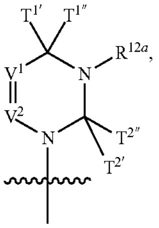

(b2)

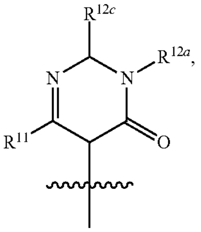

(b3)

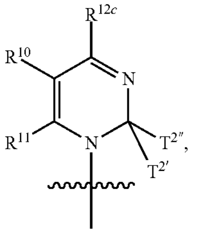

-continued (b4)

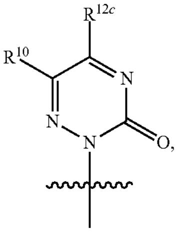

or (b5)

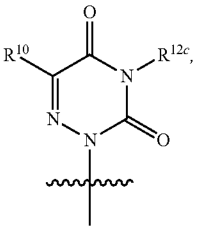

or a pharmaceutically acceptable salt or stereoisomer thereof,

Wherein ⋯ is a single or double bond; each of T1', T1", T2', and T2" is, independently, H, optionally substituted alkyl, optionally substituted alkoxy, or optionally substituted thioalkoxy, or the combination of T1' and T1" or the combination of T2' and T2" join together (e.g., as in T2) to form O (oxo), S (thio), or Se (seleno); each of V1 and V2 is, independently, O, S, N(RVb)nv, or C(RVb)nv, wherein nv is an integer from 0 to 2 and each RVb is, independently, H, halo, optionally substituted amino acid, optionally substituted alkyl, optionally substituted haloalkyl, optionally substituted alkenyl, optionally substituted alkynyl, optionally substituted alkoxy, optionally substituted alkenyloxy, optionally substituted alkynyloxy, optionally substituted hydroxyalkyl, optionally substituted hydroxyalkenyl, optionally substituted hydroxyalkynyl, optionally substituted aminoalkyl (e.g., substituted with an N-protecting group, such as any described herein, e.g., trifluoroacetyl), optionally substituted aminoalkenyl, optionally substituted aminoalkynyl, optionally substituted acylaminoalkyl (e.g., substituted with an N-protecting group, such as any described herein, e.g., trifluoroacetyl), optionally substituted alkoxycarbonylalkyl, optionally substituted alkoxycarbonylalkenyl, optionally substituted alkoxycarbonylalkynyl, or optionally substituted alkynyloxy (e.g., optionally substituted with any substituent described herein, such as those selected from (1)-(21) for alkyl);

R10 is H, halo, optionally substituted amino acid, hydroxy, optionally substituted alkyl, optionally substituted alkenyl, optionally substituted alkynyl, optionally substituted aminoalkyl, optionally substituted hydroxyalkyl, optionally substituted hydroxyalkenyl, optionally substituted hydroxyalkynyl, optionally substituted aminoalkenyl, optionally substituted aminoalkynyl, optionally substituted alkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkoxy, optionally substituted carboxyalkyl, or optionally substituted carbamoylalkyl;

R11 is H or optionally substituted alkyl;

R12a is H, optionally substituted alkyl, optionally substituted hydroxyalkyl, optionally substituted hydroxyalkenyl, optionally substituted hydroxyalkynyl, optionally substituted aminoalkyl, optionally substituted aminoalkenyl, or optionally substituted aminoalkynyl, optionally substituted carboxyalkyl (e.g., optionally substituted with hydroxy), optionally substituted carboxyalkoxy, optionally substituted carboxyaminoalkyl, or optionally substituted carbamoylalkyl; and R12c is H, halo, optionally substituted alkyl, optionally substituted alkoxy, optionally substituted thioalkoxy, optionally substituted amino, optionally substituted hydroxyalkyl, optionally substituted hydroxyalkenyl, optionally substituted hydroxyalkynyl, optionally substituted aminoalkyl, optionally substituted aminoalkenyl, or optionally substituted aminoalkynyl.

Other exemplary modified uracils include those having Formula (b6)-(b9):

(b6)

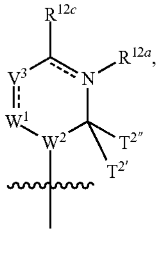

-continued (b7)

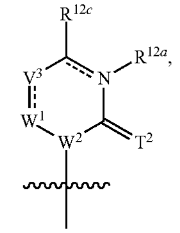

(b8)

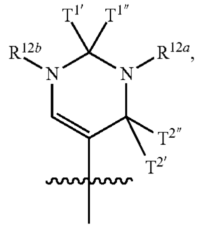

or (b9)

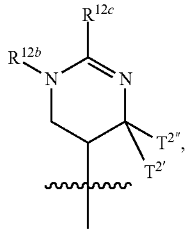

or a pharmaceutically acceptable salt or stereoisomer thereof, wherein is a single or double bond;

each of T1', T1", T2', and T2" is, independently, H, optionally substituted alkyl, optionally substituted alkoxy, or optionally substituted thioalkoxy, or the combination of T1' and T1" join together (e.g., as in T1) or the combination of T2' and T2" join together (e.g., as in T2) to form O (oxo), S (thio), or Se (seleno), or each T1 and T2 is, independently, O (oxo), S (thio), or Se (seleno);

each of W1 and W2 is, independently, N(RWa)nw or C(RWa)nw, wherein nw is an integer from 0 to 2 and each RWa is, independently, H, optionally substituted alkyl, or optionally substituted alkoxy;

each V3 is, independently, O, S, N(RVa)nv, or C(RVa)nv, wherein nv is an integer from 0 to 2 and each RVa is, independently, H, halo, optionally substituted amino acid, optionally substituted alkyl, optionally substituted hydroxyalkyl, optionally substituted hydroxyalkenyl, optionally substituted hydroxyalkynyl, optionally substituted alkenyl, optionally substituted alkynyl, optionally substituted heterocyclyl, optionally substituted alkheterocyclyl, optionally substituted alkoxy, optionally substituted alkenyloxy, or optionally substituted alkynyloxy, optionally substituted aminoalkyl (e.g., substituted with an N-protecting group, such as any described herein, e.g., trifluoroacetyl, or sulfoalkyl), optionally substituted aminoalkenyl, optionally substituted aminoalkynyl, optionally substituted acylaminoalkyl (e.g., substituted with an N-protecting group, such as any described herein, e.g., trifluoroacetyl), optionally substituted alkoxycarbonylalkyl, optionally substituted alkoxycarbonylalkenyl, optionally substituted alkoxycarbonylalkynyl, optionally substituted alkoxycarbonylacyl, optionally substituted alkoxycarbonylalkoxy, optionally substituted carboxyalkyl (e.g., optionally substituted with hydroxy and/ or an O-protecting group), optionally substituted carboxyalkoxy, optionally substituted carboxyaminoalkyl, or optionally substituted carbamoylalkyl (e.g., optionally substituted with any substituent described herein, such as those selected from (1)-(21) for alkyl), and wherein RVa and R12c taken together with the carbon atoms to which they are attached can form optionally substituted cycloalkyl, optionally substituted aryl, or optionally substituted heterocyclyl (e.g., a 5- or 6-membered ring);

R12a is H, optionally substituted alkyl, optionally substituted hydroxyalkyl, optionally substituted hydroxyalkenyl, optionally substituted hydroxyalkynyl, optionally substituted aminoalkyl, optionally substituted aminoalkenyl, optionally substituted aminoalkynyl, optionally substituted carboxyalkyl (e.g., optionally substituted with hydroxy and/or an O-protecting group), optionally substituted carboxyalkoxy, optionally substituted carboxyaminoalkyl, optionally substituted carbamoylalkyl, or absent;

R12b is H, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted aminoalkyl, optionally substituted aminoalkenyl, optionally substituted aminoalkynyl, optionally substituted alkaryl, optionally substituted heterocyclyl, optionally substituted alkheterocyclyl, optionally substituted amino acid, optionally substituted alkoxycarbonylacyl, optionally substituted alkoxycarbonylalkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkyl (e.g., optionally substituted with hydroxy and/or an O-protecting group), optionally substituted carboxyalkoxy, optionally substituted carboxyaminoalkyl, or optionally substituted carbamoylalkyl, wherein the combination of R12b and T1' or the combination of R12b and R12c can join together to form optionally substituted heterocyclyl; and R12c is H, halo, optionally substituted alkyl, optionally substituted alkoxy, optionally substituted thioalkoxy, optionally substituted amino, optionally substituted aminoalkyl, optionally substituted aminoalkenyl, or optionally substituted aminoalkynyl.

Further exemplary modified uracils include those having Formula (b28)-(b31):

(b28)

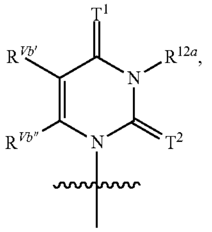

(b29)

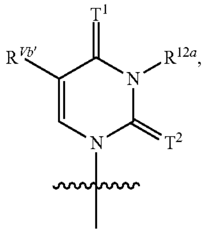

-continued (b30)

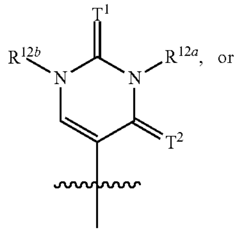

(b31)

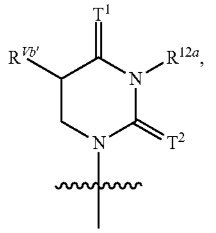

or a pharmaceutically acceptable salt or stereoisomer thereof, wherein each of T1 and T2 is, independently, O (oxo), S (thio), or Se (seleno); each RVb' and RVb" is, independently, H, halo, optionally substituted amino acid, optionally substituted alkyl, optionally substituted haloalkyl, optionally substituted hydroxyalkyl, optionally substituted hydroxyalkenyl, optionally substituted hydroxyalkynyl, optionally substituted alkenyl, optionally substituted alkynyl, optionally substituted alkoxy, optionally substituted alkenyloxy, optionally substituted alkynyloxy, optionally substituted aminoalkyl (e.g., substituted with an N-protecting group, such as any described herein, e.g., trifluoroacetyl, or sulfoalkyl), optionally substituted aminoalkenyl, optionally substituted aminoalkynyl, optionally substituted acylaminoalkyl (e.g., substituted with an N-protecting group, such as any described herein, e.g., trifluoroacetyl), optionally substituted alkoxycarbonylalkyl, optionally substituted alkoxycarbonylalkenyl, optionally substituted alkoxycarbonylalkynyl, optionally substituted alkoxycarbonylacyl, optionally substituted alkoxycarbonylalkoxy, optionally substituted carboxyalkyl (e.g., optionally substituted with hydroxy and/or an O-protecting group), optionally substituted carboxyalkoxy, optionally substituted carboxyaminoalkyl, or optionally substituted carbamoylalkyl (e.g., optionally substituted with any substituent described herein, such as those selected from (1)-(21) for alkyl) (e.g., RVb' is optionally substituted alkyl, optionally substituted alkenyl, or optionally substituted aminoalkyl, e.g., substituted with an N-protecting group, such as any described herein, e.g., trifluoroacetyl, or sulfoalkyl);

R12a is H, optionally substituted alkyl, optionally substituted carboxyaminoalkyl, optionally substituted aminoalkyl (e.g., e.g., substituted with an N-protecting group, such as any described herein, e.g., trifluoroacetyl, or sulfoalkyl), optionally substituted aminoalkenyl, or optionally substituted aminoalkynyl; and R12b is H, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted aminoalkyl, optionally substituted aminoalkenyl, optionally substituted aminoalkynyl (e.g., e.g., substituted with an N-protecting group, such as any described herein, e.g., trifluoroacetyl, or sulfoalkyl), optionally substituted alkoxycarbonylacyl, optionally substituted alkoxycarbonylalkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkoxy, optionally substituted carboxyalkyl, or optionally substituted carbamoylalkyl.

In particular embodiments, T1 is O (oxo), and T2 is S (thio) or Se (seleno). In other embodiments, T1 is S (thio), and T2 is O (oxo) or Se (seleno). In some embodiments, RVb' is H, optionally substituted alkyl, or optionally substituted alkoxy.

In other embodiments, each R12a and R12b is, independently, H, optionally substituted alkyl, optionally substituted alkenyl, optionally substituted alkynyl, or optionally substituted hydroxyalkyl. In particular embodiments, R12a is H. In other embodiments, both R12a and R12b are H.

In some embodiments, each RVb' of R12b is, independently, optionally substituted aminoalkyl (e.g., substituted with an N-protecting group, such as any described herein, e.g., trifluoroacetyl, or sulfoalkyl), optionally substituted aminoalkenyl, optionally substituted aminoalkynyl, or optionally substituted acylaminoalkyl (e.g., substituted with an N-protecting group, such as any described herein, e.g., trifluoroacetyl). In some embodiments, the amino and/or alkyl of the optionally substituted aminoalkyl is substituted with one or more of optionally substituted alkyl, optionally substituted alkenyl, optionally substituted sulfoalkyl, optionally substituted carboxy (e.g., substituted with an O-protecting group), optionally substituted hydroxy (e.g., substituted with an O-protecting group), optionally substituted carboxyalkyl (e.g., substituted with an O-protecting group), optionally substituted alkoxycarbonylalkyl (e.g., substituted with an O-protecting group), or N-protecting group. In some embodiments, optionally substituted aminoalkyl is substituted with an optionally substituted sulfoalkyl or optionally substituted alkenyl. In particular embodiments, R12a and RVb" are both H. In particular embodiments, T1 is O (oxo), and T2 is S (thio) or Se (seleno).

In some embodiments, RVb' is optionally substituted alkoxycarbonylalkyl or optionally substituted carbamoylalkyl.

In particular embodiments, the optional substituent for R12a, R12b, R12c, or RVa is a polyethylene glycol group (e.g., —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl); or an amino-polyethylene glycol group (e.g., —NRN1(CH2)s2(CH2CH2O)s1(CH2)s3NRN1, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each RN1 is, independently, hydrogen or optionally substituted C1-6 alkyl).

In some embodiments, B is a modified cytosine. Exemplary modified cytosines include compounds of Formula (b10)-(b14):

(b10)

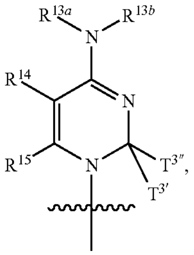

(b11)

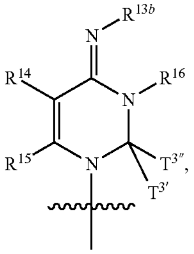

(b12)

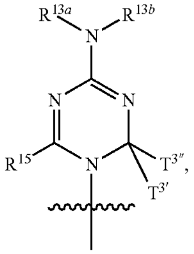

(b13)

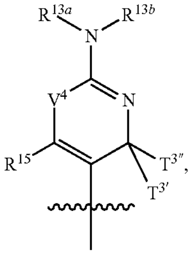

or (b14)

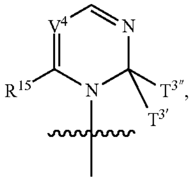

or a pharmaceutically acceptable salt or stereoisomer thereof, wherein each of T3' and T3" is, independently, H, optionally substituted alkyl, optionally substituted alkoxy, or optionally substituted thioalkoxy, or the combination of T3' and T3" join together (e.g., as in T3) to form O (oxo), S (thio), or Se (seleno); each V4 is, independently, O, S, N(RVc)nv, or C(RVc)nv, wherein nv is an integer from 0 to 2 and each RVc is, independently, H, halo, optionally substituted amino acid, optionally substituted alkyl, optionally substituted alkenyl, optionally substituted alkynyl, optionally substituted alkoxy, optionally substituted alkenyloxy, optionally substituted heterocyclyl, optionally substituted alkheterocyclyl, or optionally substituted alkynyloxy (e.g., optionally substituted with any substituent described herein, such as those selected from (1)-(21) for alkyl), wherein the combination of R13b and RVc can be taken together to form optionally substituted heterocyclyl;

each V5 is, independently, N(RVd)nv, or C(RVd)nv, wherein nv is an integer from 0 to 2 and each RVd is, independently, H, halo, optionally substituted amino acid, optionally substituted alkyl, optionally substituted alkenyl, optionally substituted alkynyl, optionally substituted alkoxy, optionally substituted alkenyloxy, optionally substituted heterocyclyl, optionally substituted alkheterocyclyl, or optionally substituted alkynyloxy (e.g., optionally substituted with any substituent described herein, such as those selected from (1)-(21) for alkyl) (e.g., V5 is —CH or N);

each of R13a and R13b is, independently, H, optionally substituted acyl, optionally substituted acyloxyalkyl, optionally substituted alkyl, or optionally substituted alkoxy, wherein the combination of R13b and R14 can be taken together to form optionally substituted heterocyclyl;

each R14 is, independently, H, halo, hydroxy, thiol, optionally substituted acyl, optionally substituted amino acid, optionally substituted alkyl, optionally substituted haloalkyl, optionally substituted alkenyl, optionally substituted alkynyl, optionally substituted hydroxyalkyl (e.g., substituted with an O-protecting group), optionally substituted hydroxyalkenyl, optionally substituted hydroxyalkynyl, optionally substituted alkoxy, optionally substituted alkenyloxy, optionally substituted alkynyloxy, optionally substituted aminoalkoxy, optionally substituted alkoxyalkoxy, optionally substituted acyloxyalkyl, optionally substituted amino (e.g., —NHR, wherein R is H, alkyl, aryl, or phosphoryl), azido, optionally substituted aryl, optionally substituted heterocyclyl, optionally substituted alkheterocyclyl, optionally substituted aminoalkyl, optionally substituted aminoalkenyl, or optionally substituted aminoalkyl; and each of R15 and R16 is, independently, H, optionally substituted alkyl, optionally substituted alkenyl, or optionally substituted alkynyl.

Further exemplary modified cytosines include those having Formula (b32)-(b35):

(b32)

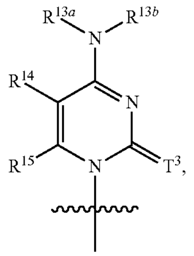

(b33)

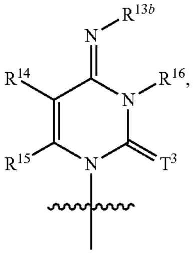

-continued (b34)

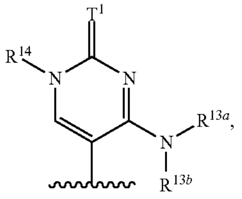

or (b35)

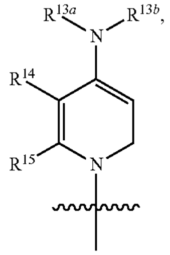

or a pharmaceutically acceptable salt or stereoisomer thereof, wherein each of T1 and T3 is, independently, O (oxo), S (thio), or Se (seleno); each of R13a and R13b is, independently, H, optionally substituted acyl, optionally substituted acyloxyalkyl, optionally substituted alkyl, or optionally substituted alkoxy, wherein the combination of R13b and R14 can be taken together to form optionally substituted heterocyclyl;

each R14 is, independently, H, halo, hydroxy, thiol, optionally substituted acyl, optionally substituted amino acid, optionally substituted alkyl, optionally substituted haloalkyl, optionally substituted alkenyl, optionally substituted alkynyl, optionally substituted hydroxyalkyl (e.g., substituted with an O-protecting group), optionally substituted hydroxyalkenyl, optionally substituted hydroxyalkynyl, optionally substituted alkoxy, optionally substituted alkenyloxy, optionally substituted alkynyloxy, optionally substituted aminoalkoxy, optionally substituted alkoxyalkoxy, optionally substituted acyloxyalkyl, optionally substituted amino (e.g., —NHR, wherein R is H, alkyl, aryl, or phosphoryl), azido, optionally substituted aryl, optionally substituted heterocyclyl, optionally substituted alkheterocyclyl, optionally substituted aminoalkyl (e.g., hydroxyalkyl, alkyl, alkenyl, or alkynyl), optionally substituted aminoalkenyl, or optionally substituted aminoalkynyl; and each of R15 and R16 is, independently, H, optionally substituted alkyl, optionally substituted alkenyl, or optionally substituted alkynyl (e.g., R15 is H, and R16 is H or optionally substituted alkyl).

In some embodiments, R15 is H, and R16 is H or optionally substituted alkyl. In particular embodiments, R14 is H, acyl, or hydroxyalkyl. In some embodiments, R14 is halo. In some embodiments, both R14 and R15 are H. In some embodiments, both R15 and R16 are H. In some embodiments, each of R14 and R15 and R16 is H. In further embodiments, each of R13a and R13b is independently, H or optionally substituted alkyl.

Further non-limiting examples of modified cytosines include compounds of Formula (b36):

(b36)

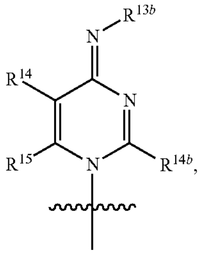

or a pharmaceutically acceptable salt or stereoisomer thereof, wherein each R13b is, independently, H, optionally substituted acyl, optionally substituted acyloxyalkyl,optionally substituted alkyl, or optionally substituted alkoxy, wherein the combination of R13b and R14b can be taken together to form optionally substituted heterocyclyl; each R14a and R14b is, independently, H, halo, hydroxy, thiol, optionally substituted acyl, optionally substituted amino acid, optionally substituted alkyl, optionally substituted haloalkyl, optionally substituted alkenyl, optionally substituted alkynyl, optionally substituted hydroxyalkyl (e.g., substituted with an O-protecting group), optionally substituted hydroxyalkenyl, optionally substituted alkoxy, optionally substituted alkenyloxy, optionally substituted alkynyloxy, optionally substituted aminoalkoxy, optionally substituted alkoxyalkoxy, optionally substituted acyloxyalkyl, optionally substituted amino (e.g., —NHR, wherein R is H, alkyl, aryl, phosphoryl, optionally substituted aminoalkyl, or optionally substituted carboxyaminoalkyl), azido, optionally substituted aryl, optionally substituted heterocyclyl, optionally substituted alkheterocyclyl, optionally substituted aminoalkyl, optionally substituted aminoalkenyl, or optionally substituted aminoalkynyl; and each of R15 is, independently, H, optionally substituted alkyl, optionally substituted alkenyl, or optionally substituted alkynyl.

In particular embodiments, R14b is an optionally substituted amino acid (e.g., optionally substituted lysine). In some embodiments, R14a is H.

In some embodiments, B is a modified guanine Exemplary modified guanines include compounds of Formula (b15)-(b17):

(b15)

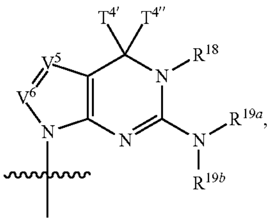

(b16)

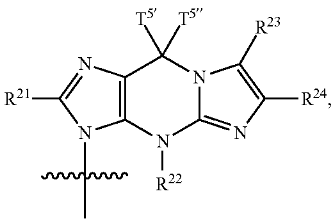

or

-continued (b17)

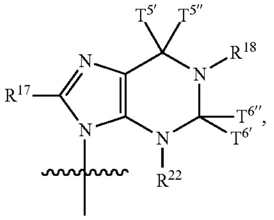

or a pharmaceutically acceptable salt or stereoisomer thereof, wherein each of T4', T4", T5', T5", T6', and T6" is, independently, H, optionally substituted alkyl, or optionally substituted alkoxy, and wherein the combination of T4' and T4" (e.g., as in T4) or the combination of T5' and T5" (e.g., as in T5) or the combination of T6' and T6" (e.g., as in T6) join together form O (oxo), S (thio), or Se (seleno);

each of V5 and V6 is, independently, O, S, N(RVd)nv, or C(RVd)nv, wherein nv is an integer from 0 to 2 and each RVd is, independently, H, halo, thiol, optionally substituted amino acid, cyano, amidine, optionally substituted aminoalkyl, optionally substituted aminoalkenyl, optionally substituted aminoalkynyl, optionally substituted alkyl, optionally substituted alkenyl, optionally substituted alkynyl, optionally substituted alkoxy, optionally substituted alkenyloxy, or optionally substituted alkynyloxy (e.g., optionally substituted with any substituent described herein, such as those selected from (1)-(21) for alkyl), optionally substituted thioalkoxy, or optionally substituted amino; and each of R17, R18, R19a, R19b, R21, R22, R23, and R24 is, independently, H, halo, thiol, optionally substituted alkyl, optionally substituted alkenyl, optionally substituted alkynyl, optionally substituted thioalkoxy, optionally substituted amino, or optionally substituted amino acid.

Exemplary modified guanosines include compounds of Formula (b37)-(b40):

(b37)

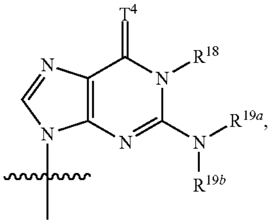

(b38)

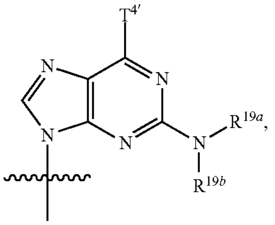

-continued (b39)

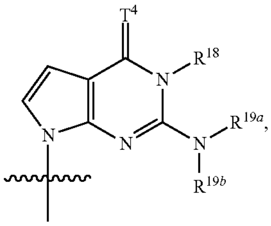

or (b40)

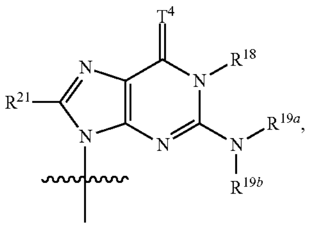

or a pharmaceutically acceptable salt or stereoisomer thereof, wherein each of T4' is, independently, H, optionally substituted alkyl, or optionally substituted alkoxy, and each T4 is, independently, O (oxo), S (thio), or Se (seleno); each of R18, R19a, R19b, and R21 is, independently, H, halo, thiol, optionally substituted alkyl, optionally substituted alkenyl, optionally substituted alkynyl, optionally substituted thioalkoxy, optionally substituted amino, or optionally substituted amino acid.

In some embodiments, R18 is H or optionally substituted alkyl. In further embodiments, T4 is oxo. In some embodiments, each of R19a and R19b is, independently, H or optionally substituted alkyl.

In some embodiments, B is a modified adenine. Exemplary modified adenines include compounds of Formula (b18)-(b20):

(b18)

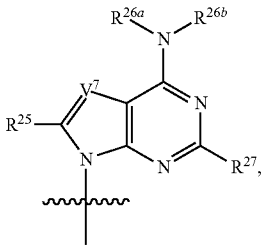

(b19)

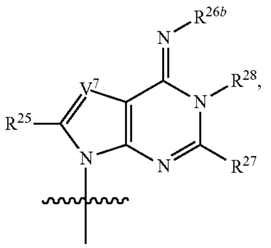

or

-continued (b20)

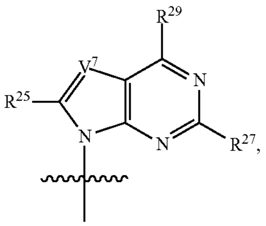

or a pharmaceutically acceptable salt or stereoisomer thereof, wherein each V7 is, independently, O, S, N(RVe)nv, or C(RVe)nv, wherein nv is an integer from 0 to 2 and each RVe is, independently, H, halo, optionally substituted amino acid, optionally substituted alkyl, optionally substituted alkenyl, optionally substituted alkynyl, optionally substituted alkoxy, optionally substituted alkenyloxy, or optionally substituted alkynyloxy (e.g., optionally substituted with any substituent described herein, such as those selected from (1)-(21) for alkyl);

each R25 is, independently, H, halo, thiol, optionally substituted alkyl, optionally substituted alkenyl, optionally substituted alkynyl, optionally substituted thioalkoxy, or optionally substituted amino;

each of R26a and R26b is, independently, H, optionally substituted acyl, optionally substituted amino acid, optionally substituted carbamoylalkyl, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted alkoxy, or polyethylene glycol group (e.g., —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl); or an amino-polyethylene glycol group (e.g., —NRN1(CH2)s2(CH2CH2O)s1(CH2)s3NRN1, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each RN1 is, independently, hydrogen or optionally substituted C1-6 alkyl);

each R27 is, independently, H, optionally substituted alkyl, optionally substituted alkenyl, optionally substituted alkynyl, optionally substituted alkoxy, optionally substituted thioalkoxy or optionally substituted amino;

each R28 is, independently, H, optionally substituted alkyl, optionally substituted alkenyl, or optionally substituted alkynyl; and each R29 is, independently, H, optionally substituted acyl, optionally substituted amino acid, optionally substituted carbamoylalkyl, optionally substituted alkyl, optionally substituted alkenyl, optionally substituted alkynyl, optionally substituted hydroxyalkyl, optionally substituted hydroxyalkenyl, optionally substituted alkoxy, or optionally substituted amino.

Exemplary modified adenines include compounds of Formula (b41)-(b43):

(b41)

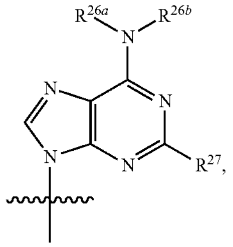

(b42)

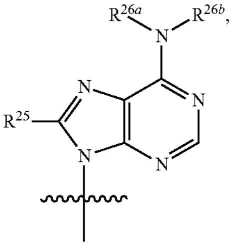

or (b43)

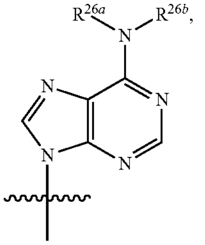

or a pharmaceutically acceptable salt or stereoisomer thereof, wherein each R25 is, independently, H, halo, thiol, optionally substituted alkyl, optionally substituted alkenyl, optionally substituted alkynyl, optionally substituted thioalkoxy, or optionally substituted amino; each of R26a and R26b is, independently, H, optionally substituted acyl, optionally substituted amino acid, optionally substituted carbamoylalkyl, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted alkoxy, or polyethylene glycol group (e.g., —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl); or an amino-polyethylene glycol group (e.g., —NRN1(CH2)s2(CH2CH2O)s1(CH2)s3NRN1, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each RN1 is, independently, hydrogen or optionally substituted C1-6 alkyl); and each R27 is, independently, H, optionally substituted alkyl, optionally substituted alkenyl, optionally substituted alkynyl, optionally substituted alkoxy, optionally substituted thioalkoxy, or optionally substituted amino.

In some embodiments, R26a is H, and R26b is optionally substituted alkyl. In some embodiments, each of R26a and R26b is, independently, optionally substituted alkyl. In particular embodiments, R27 is optionally substituted alkyl, optionally substituted alkoxy, or optionally substituted thioalkoxy. In other embodiments, R25 is optionally substituted alkyl, optionally substituted alkoxy, or optionally substituted thioalkoxy.

In particular embodiments, the optional substituent for R26a, R26b, or R29 is a polyethylene glycol group (e.g., —(CH2)s2(OCH2CH2)s1(CH2)s3OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C1-20 alkyl); or an amino-polyethylene glycol group (e.g., —NRN1(CH2)s2(CH2CH2O)s1(CH2)s3NRN1, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each RN1 is, independently, hydrogen or optionally substituted C1-6 alkyl).

In some embodiments, B may have Formula (b21):

(b21)

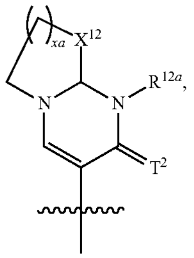

wherein X12 is, independently, O, S, optionally substituted alkylene (e.g., methylene), or optionally substituted heteroalkylene, xa is an integer from 0 to 3, and R12a and T2 are as described herein.

In some embodiments, B may have Formula (b22):

(b22)

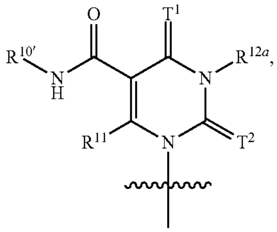

wherein R10' is, independently, optionally substituted alkyl, optionally substituted alkenyl, optionally substituted alkynyl, optionally substituted aryl, optionally substituted heterocyclyl, optionally substituted aminoalkyl, optionally substituted aminoalkenyl, optionally substituted aminoalkynyl, optionally substituted alkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkoxy, optionally substituted carboxyalkyl, or optionally substituted carbamoylalkyl, and R11, R12a, T1, and T2 are as described herein.

In some embodiments, B may have Formula (b23):

(b23)

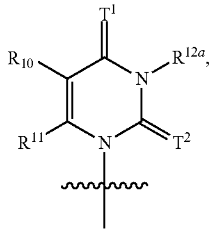

wherein R10 is optionally substituted heterocyclyl (e.g., optionally substituted furyl, optionally substituted thienyl, or optionally substituted pyrrolyl), optionally substituted aryl (e.g., optionally substituted phenyl or optionally substituted naphthyl), or any substituent described herein (e.g., for R10); and wherein R11 (e.g., H or any substituent described herein), R12a (e.g., H or any substituent described herein), T1 (e.g., oxo or any substituent described herein), and T2 (e.g., oxo or any substituent described herein) are as described herein.

In some embodiments, B may have Formula (b24):

(b24)

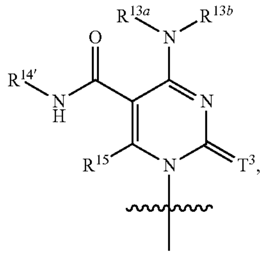

wherein R14' is, independently, optionally substituted alkyl, optionally substituted alkenyl, optionally substituted alkynyl, optionally substituted aryl, optionally substituted heterocyclyl, optionally substituted alkaryl, optionally substituted alkheterocyclyl, optionally substituted aminoalkyl, optionally substituted aminoalkenyl, optionally substituted aminoalkynyl, optionally substituted alkoxy, optionally substituted alkoxycarbonylalkenyl, optionally substituted alkoxycarbonylalkynyl, optionally substituted alkoxycarbonylalkyl, optionally substituted alkoxycarbonylalkoxy, optionally substituted carboxyalkoxy, optionally substituted carboxyalkyl, or optionally substituted carbamoylalkyl, and R13a, R13b, R15, and T3 are as described herein.

In some embodiments, B may have Formula (b25):

(b25)

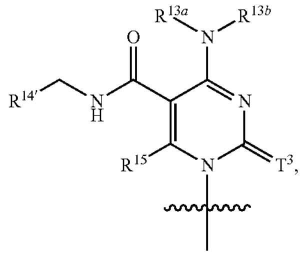

wherein R14' is optionally substituted heterocyclyl (e.g., optionally substituted furyl, optionally substituted thienyl, or optionally substituted pyrrolyl), optionally substituted aryl (e.g., optionally substituted phenyl or optionally substituted naphthyl), or any substituent described herein (e.g., for R14 or R14'); and wherein R13a (e.g., H or any substituent described herein), R13b (e.g., H or any substituent described herein), R15 (e.g., H or any substituent described herein), and T3 (e.g., oxo or any substituent described herein) are as described herein.

In some embodiments, B is a nucleobase selected from the group consisting of cytosine, guanine, adenine, and uracil. In some embodiments, B may be:

(b26)

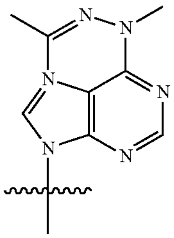

or (b27)

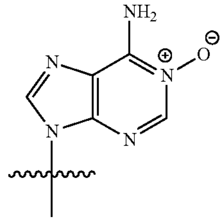

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridine or 5-bromo-uridine), 3-methyl-uridine (m3U), 5-methoxy-uridine (mo5U), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine(τm5s2U), 1-taurinomethyl-4-thio-pseudouridine, 5-methyl-uridine (m5U, i.e., having the nucleobase deoxythymine), 1-methylpseudouridine (m1ψ), 5-methyl-2-thio-uridine (m5s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine (also known as 1-methylpseudouridine (m1ψ)), 3-(3-amino-3-carboxypropyl)uridine (acp3U), 1-methyl-3-(3-amino-3-carboxypropyl)pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2' F ara uridine, 2' F uridine, 2' OH ara uridine, 5(2 carbomethoxyvinyl) uridine, and 5[3(1E propenylamino)uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m3C), N4-acetyl-cytidine (ac4C), 5-formyl-cytidine (f5C), N4-methyl-cytidine (m4C), 5-methyl-cytidine (m5C), 5-halo-cytidine (e.g., 5-iodo-cytidine), 5-hydroxymethyl-cytidine (hm5C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k2C), α-thio-cytidine, 2'-O-methyl-cytidine (Cm), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytidine, 2' F ara cytidine, 2' F cytidine, and 2' OH ara cytidine.

In some embodiments, the modified nucleobase is a modified adenine. Exemplary nucleobases and nucleosides having a modified adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m1A), 2-methyl-adenine (m2A), N6-methyl-adenosine (m6A), 2-methylthio-N6-methyl-adenosine (ms2m6A), N6-isopentenyl-adenosine (i6A), 2-methylthio-N6-isopentenyl-adenosine (ms2i6A), N6-(cis-hydroxyisopentenyl)adenosine (io6A), 2-methylthio-N6-(cis-hydroxyisopentenyl) adenosine (ms2io6A), N6-glycinylcarbamoyl-adenosine (g6A), N6-threonylcarbamoyl-adenosine (t6A), N6-methyl-N6-threonylcarbamoyl-adenosine (m6t6A), 2-methylthio-N6-threonylcarbamoyl-adenosine (ms2g6A), N6,N6-dimethyl-adenosine (m62A), N6-hydroxynorvalylcarbamoyl-adenosine (hn6A), 2-methylthio-N6-hydroxynorvalylcarbamoyl-adenosine (ms2hn6A), N6-acetyl-adenosine (ac6A), 7-methyl-adenine, 2-methyl-thio-adenine, 2-methoxy-adenine, α-thio-adenosine, 2'-O-methyl-adenosine (Am), N6,2'-O-dimethyl-adenosine (m6Am), N6,N6,2'-O-trimethyl-adenosine (m62Am), 1,2'-O-dimethyl-adenosine (m1Am), 2'-O-ribosyladenosine (phosphate) (Ar(p)), 2-amino-N6-methyl-purine, 1-thio-adenosine, 8-azido-adenosine, 2' F ara adenosine, 2' F adenosine, 2' OH ara adenosine, and N6 (19 amino pentaoxanonadecyl)-adenosine.

In some embodiments, the modified nucleobase is a modified guanine Exemplary nucleobases and nucleosides having a modified guanine include inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine (preQ0), 7-aminomethyl-7-deaza-guanosine (preQ1), archaeosine (G+), 7-deaza-8-aza-guanosine, 6-thio-guanosine, 6-thio-7-deaza-guanosine, 6-thio-7-deaza-8-aza-guanosine, 7-methyl-guanosine (m7G), 6-thio-7-methyl-guanosine, 7-methyl-inosine, 6-methoxy-guanosine, 1-methyl-guanosine (m1G), N2-methyl-guanosine (m2G), N2,N2-dimethyl-guanosine (m22G), N2,7-dimethyl-guanosine (m2,7G), N2,N2,7-dimethyl-guanosine (m2,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), and 2'-O-ribosylguanosine (phosphate) (Gr(p)).

The nucleobase of the nucleotide can be independently selected from a purine, a pyrimidine, a purine or pyrimidine analog. For example, the nucleobase can each be independently selected from adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d] pyrimidines, pyrazin-2-ones, 1,2,4-triazine, pyridazine; and 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Modifications on the Internucleoside Linkage

The modified nucleotides, which may be incorporated into a polynucleotide, primary construct, or mmRNA molecule, can be modified on the internucleoside linkage (e.g., phosphate backbone). Herein, in the context of the polynucleotide backbone, the phrases “phosphate” and “phosphodiester” are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment. Phosphorothioate linked polynucleotides, primary constructs, or mmRNA molecules are expected to also reduce the innate immune response through weaker binding/activation of cellular innate immune molecules.

In specific embodiments, a modified nucleoside includes an alpha-thio-nucleoside (e.g., 5'-O-(1-thiophosphate)-adenosine, 5'-O-(1-thiophosphate)-cytidine (α-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present invention, including internucleoside linkages which do not contain a phosphorous atom, are described herein below.

Combinations of Modified Sugars, Nucleobases, and Internucleoside Linkages

The polynucleotides, primary constructs, and mmRNA of the invention can include a combination of modifications to the sugar, the nucleobase, and/or the internucleoside linkage. These combinations can include any one or more modifications described herein. For examples, any of the nucleotides described herein in Formulas (Ia), (Ia-1)-(Ia-3), (Ib)-(If), (IIa)-(IIp), (IIb-1), (IIb-2), (IIc-1)-(IIc-2), (IIn-1), (IIn-2), (IVa)-(IV1), and (IXa)-(IXr) can be combined with any of the nucleobases described herein (e.g., in Formulas (b1)-(b43) or any other described herein).

Cytotoxic Nucleosides

In one embodiment, the polynucleotides, primary constructs or mmRNA of the present invention may incorporate one or more cytotoxic nucleosides. For example, cytotoxic nucleosides may be incorporated into polynucleotides, primary constructs or mmRNA such as bifunctional modified RNAs or mRNAs. Cytotoxic nucleoside anti-cancer agents include, but are not limited to, adenosine arabinoside, cytarabine, cytosine arabinoside, 5-fluorouracil, fludarabine, floxuridine, FTORAFUR® (a combination of tegafur and uracil), tegafur ((RS)-5-fluoro-1-(tetrahydrofuran-2-yl)pyrimidine-2,4(1H,3H)-dione), and 6-mercaptopurine.

A number of cytotoxic nucleoside analogues are in clinical use, or have been the subject of clinical trials, as anticancer agents. Examples of such analogues include, but are not limited to, cytarabine, gemcitabine, troxacitabine, decitabine, tezacitabine, 2'-deoxy-2'-methylidenecytidine (DMDC), cladribine, clofarabine, 5-azacytidine, 4'-thio-aracytidine, cyclopentenylcytosine and 1-(2-C-cyano-2-deoxy-beta-D-arabino-pentofuranosyl)-cytosine. Another example of such a compound is fludarabine phosphate. These compounds may be administered systemically and may have side effects which are typical of cytotoxic agents such as, but not limited to, little or no specificity for tumor cells over proliferating normal cells.

A number of prodrugs of cytotoxic nucleoside analogues are also reported in the art. Examples include, but are not limited to, N4-behenoyl-1-beta-D-arabinofuranosylcytosine, N4-octadecyl-1-beta-D-arabinofuranosylcytosine, N4-palmitoyl-1-(2-C-cyano-2-deoxy-beta-D-arabino-pentofuranosyl) cytosine, and P-4055 (cytarabine 5'-elaidic acid ester). In general, these prodrugs may be converted into the active drugs mainly in the liver and systemic circulation and display little or no selective release of active drug in the tumor tissue. For example, capecitabine, a prodrug of 5'-deoxy-5-fluorocytidine (and eventually of 5-fluorouracil), is metabolized both in the liver and in the tumor tissue. A series of capecitabine analogues containing "an easily hydrolysable radical under physiological conditions" has been claimed by Fujiu et al. (U.S. Pat. No. 4,966,891) and is herein incorporated by reference. The series described by Fujiu includes N4 alkyl and aralkyl carbamates of 5'-deoxy-5-fluorocytidine and the implication that these compounds will be activated by hydrolysis under normal physiological conditions to provide 5'-deoxy-5-fluorocytidine.

A series of cytarabine N4-carbamates has been by reported by Fadl et al (Pharmazie. 1995, 50, 382-7, herein incorporated by reference) in which compounds were designed to convert into cytarabine in the liver and plasma. WO 2004/041203, herein incorporated by reference, discloses prodrugs of gemcitabine, where some of the prodrugs are N4-carbamates. These compounds were designed to overcome the gastrointestinal toxicity of gemcitabine and were intended to provide gemcitabine by hydrolytic release in the liver and plasma after absorption of the intact prodrug from the gastrointestinal tract. Nomura et al (Bioorg Med. Chem. 2003, 11, 2453-61, herein incorporated by reference) have described acetal derivatives of 1-(3-C-ethynyl-β-D-ribo-pentofaranosyl) cytosine which, on bioreduction, produced an intermediate that required further hydrolysis under acidic conditions to produce a cytotoxic nucleoside compound.

Cytotoxic nucleotides which may be chemotherapeutic also include, but are not limited to, pyrazolo[3,4-D]-pyrimidines, allopurinol, azathioprine, capecitabine, cytosine arabinoside, fluorouracil, mercaptopurine, 6-thioguanine, acyclovir, ara-adenosine, ribavirin, 7-deaza-adenosine, 7-deazaguanosine, 6-aza-uracil, 6-aza-cytidine, thymidine ribonucleotide, 5-bromodeoxyuridine, 2-chloro-purine, and inosine, or combinations thereof.

The The modified nucleosides and nucleotides used in the synthesis of polynucleotides, primary constructs, and mmRNA molecules disclosed herein can be prepared from readily available starting materials using the following general methods and procedures. Where typical or preferred process conditions (e.g., reaction temperatures, times, mole ratios of reactants, solvents, pressures, etc.) are provided, a skilled artisan would be able to optimize and develop additional process conditions. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., 1H or 13C) infrared spectroscopy, spectrophotometry (e.g., UV-visible), or mass spectrometry, or by chromatography such as high performance liquid chromatography (HPLC) or thin layer chromatography.

Preparation of polypeptides, primary constructs, and mmRNA molecules of the present invention can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of modified nucleosides and nucleotides can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Modified nucleosides and nucleotides (e.g., building block molecules) can be prepared according to the synthetic methods described in Ogata et al., J. Org. Chem. 74:2585-2588 (2009); Purmal et al., Nucl. Acids Res. 22(1): 72-78, (1994); Fukuhara et al., Biochemistry, 1(4): 563-568 (1962); and Xu et al., Tetrahedron, 48(9): 1729-1740 (1992), each of which are incorporated by reference in their entirety.

The polypeptides, primary constructs, and mmRNA of the invention may or may not be uniformly modified along the entire length of the molecule. For example, one or more or all types of nucleotide (e.g., purine or pyrimidine, or any one or more or all of A, G, U, C) may or may not be uniformly modified in a polynucleotide of the invention, or in a given predetermined sequence region thereof (e.g. one or more of the sequence regions represented in FIG. 1). In some embodiments, all nucleotides X in a polynucleotide of the invention (or in a given sequence region thereof) are modified, wherein X may any one of nucleotides A, G, U, C, or any one of the combinations A+G, A+U, A+C, G+U, G+C, U+C, A+G+U, A+G+C, G+U+C or A+G+C.

Different sugar modifications, nucleotide modifications, and/or internucleoside linkages (e.g., backbone structures) may exist at various positions in the polynucleotide, primary construct, or mmRNA. One of ordinary skill in the art will appreciate that the nucleotide analogs or other modification(s) may be located at any position(s) of a polynucleotide, primary construct, or mmRNA such that the function of the polynucleotide, primary construct, or mmRNA is not substantially decreased. A modification may also be a 5' or 3' terminal modification. The polynucleotide, primary construct, or mmRNA may contain from about 1% to about 100% modified nucleotides (either in relation to overall nucleotide content, or in relation to one or more types of nucleotide, i.e. any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, the polynucleotide, primary construct, or mmRNA includes a modified pyrimidine (e.g., a modified uracil/uridine/U or modified cytosine/cytidine/C). In some embodiments, the uracil or uridine (generally: U) in the polynucleotide, primary construct, or mmRNA molecule may be replaced with from about 1% to about 100% of a modified uracil or modified uridine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of a modified uracil or modified uridine). The modified uracil or uridine can be replaced by a compound having a single unique structure or by a plurality of compounds having different structures (e.g., 2, 3, 4 or more unique structures, as described herein). In some embodiments, the cytosine or cytidine (generally: C) in the polynucleotide, primary construct, or mmRNA molecule may be replaced with from about 1% to about 100% of a modified cytosine or modified cytidine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of a modified cytosine or modified cytidine). The modified cytosine or cytidine can be replaced by a compound having a single unique structure or by a plurality of compounds having different structures (e.g., 2, 3, 4 or more unique structures, as described herein).

In some embodiments, the present disclosure provides methods of synthesizing a polynucleotide, primary construct, or mmRNA (e.g., the first region, first flanking region, or second flanking region) including n number of linked nucleosides having Formula (Ia-1):

(Ia-1)

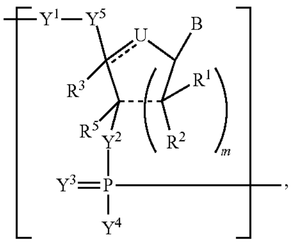

comprising:

a) reacting a nucleotide of Formula (IV-1):

(IV-1)

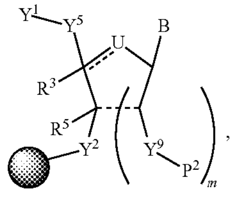

with a phosphoramidite compound of Formula (V-1):

(V-1)

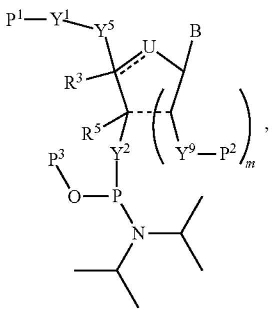

wherein Y9 is H, hydroxy, phosphoryl, pyrophosphate, sulfate, amino, thiol, optionally substituted amino acid, or a peptide (e.g., including from 2 to 12 amino acids); and each P1, P2, and P3 is, independently, a suitable protecting group; and 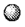 denotes a solid support;

to provide a polynucleotide, primary construct, or mmRNA of Formula (VI-1):

(VI-1)

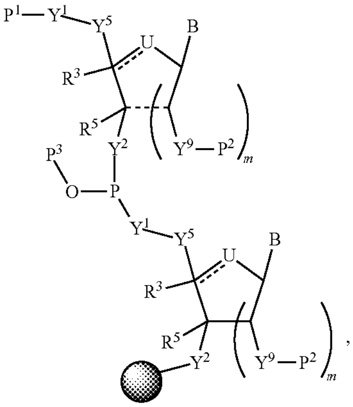

and b) oxidizing or sulfurizing the polynucleotide, primary construct, or mmRNA of Formula (V) to yield a polynucleotide, primary construct, or mmRNA of Formula (VII-1):

(VII-1)

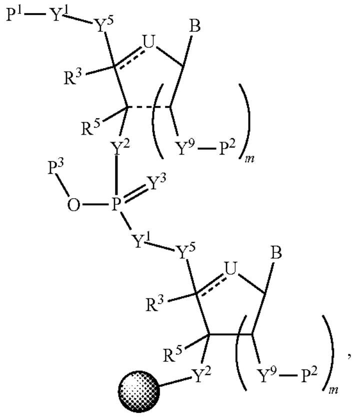

and c) removing the protecting groups to yield the polynucleotide, primary construct, or mmRNA of Formula (Ia).

In some embodiments, steps a) and b) are repeated from 1 to about 10,000 times. In some embodiments, the methods further comprise a nucleotide (e.g., mmRNA molecule) selected from the group consisting of A, C, G and U adenosine, cytosine, guanosine, and uracil. In some embodiments, the nucleobase may be a pyrimidine or derivative thereof. In some embodiments, the polynucleotide, primary construct, or mmRNA is translatable.

Other components of polynucleotides, primary constructs, and mmRNA are optional, and are beneficial in some embodiments. For example, a 5' untranslated region (UTR) and/or a 3'UTR are provided, wherein either or both may independently contain one or more different nucleotide modifications. In such embodiments, nucleotide modifications may also be present in the translatable region. Also provided are polynucleotides, primary constructs, and mmRNA containing a Kozak sequence.

Combinations of Nucleotides in mmRNA

Further examples of modified nucleotides and modified nucleotide combinations are provided below in Table 9. These combinations of modified nucleotides can be used to form the polypeptides, primary constructs, or mmRNA of the invention. Unless otherwise noted, the modified nucleotides may be completely substituted for the natural nucleotides of the modified nucleic acids or mmRNA of the invention. As a non-limiting example, the natural nucleotide uridine may be substituted with a modified nucleoside described herein. In another non-limiting example, the natural nucleotide uridine may be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9%) with at least one of the modified nucleoside disclosed herein.

TABLE 9

| Modified Nucleotide | Modified Nucleotide Combination |
|---|---|
| α-thio-cytidine | α-thio-cytidine/5-iodo-uridine |
| | α-thio-cytidine/N1-methyl-pseudouridine |
| | α-thio-cytidine/α-thio-uridine |
| | α-thio-cytidine/5-methyl-uridine |
| | α-thio-cytidine/pseudo-uridine |
| | about 50% of the cytosines are α-thio-cytidine |
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |
| | about 25% of cytosines are pseudoisocytidine |
| | pseudoisocytidine/about 50% of uridines are N1-methyl-pseudouridine and about 50% of uridines are pseudouridine |
| | pseudoisocytidine/about 25% of uridines are N1-methyl-pseudouridine and about 25% of uridines are pseudouridine |
| pyrrolo-cytidine | pyrrolo-cytidine/5-iodo-uridine |
| | pyrrolo-cytidine/N1-methyl-pseudouridine |
| | pyrrolo-cytidine/α-thio-uridine |
| | pyrrolo-cytidine/5-methyl-uridine |
| | pyrrolo-cytidine/pseudouridine |
| | about 50% of the cytosines are pyrrolo-cytidine |
| 5-methyl-cytidine | 5-methyl-cytidine/5-iodo-uridine |
| | 5-methyl-cytidine/N1-methyl-pseudouridine |
| | 5-methyl-cytidine/α-thio-uridine |
| | 5-methyl-cytidine/5-methyl-uridine |
| | 5-methyl-cytidine/pseudouridine |
| | about 25% of cytosines are 5-methyl-cytidine |
| | about 50% of cytosines are 5-methyl-cytidine |
| | 5-methyl-cytidine/5-methoxy-uridine |
| | 5-methyl-cytidine/5-bromo-uridine |
| | 5-methyl-cytidine/2-thio-uridine |
| | 5-methyl-cytidine/about 50% of uridines are 2-thio-uridine |
| | about 50% of uridines are 5-methyl-cytidine/about 50% of uridines are 2-thio-uridine |
| N4-acetyl-cytidine | N4-acetyl-cytidine/5-iodo-uridine |
| | N4-acetyl-cytidine/N1-methyl-pseudouridine |
| | N4-acetyl-cytidine/α-thio-uridine |
| | N4-acetyl-cytidine/5-methyl-uridine |
| | N4-acetyl-cytidine/pseudouridine |
| | about 50% of cytosines are N4-acetyl-cytidine |
| | about 25% of cytosines are N4-acetyl-ytidine |
| | N4-acetyl-cytidine/5-methoxy-uridine |
| | N4-acetyl-cytidine/5-bromo-uridine |
| | N4-acetyl-cytidine/2-thio-uridine |
| | about 50% of cytosines are |

TABLE 9-continued

| Modified Nucleotide | Modified Nucleotide Combination |
|---|---|
| | N4-acetyl-cytidine/about 50% of uridines are 2-thio-uridine |

Further examples of modified nucleotide combinations are provided below in Table 10. These combinations of modified nucleotides can be used to form the polypeptides, primary constructs, or mmRNA of the invention.

TABLE 10

| Modified Nucleotide | Modified Nucleotide Combination |
|---|---|
| modified cytidine having one or more nucleobases of Formula (b10) | modified cytidine with (b10)/pseudouridine |
| | modified cytidine with (b10)/N1-methyl-pseudouridine |
| | modified cytidine with (b10)/5-methoxy-uridine |
| | modified cytidine with (b10)/5-methyl-uridine |
| | modified cytidine with (b10)/5-bromo-uridine |
| | modified cytidine with (b10)/2-thio-uridine |
| | about 50% of cytidine substituted with modified cytidine (b10)/about 50% of uridines are 2-thio-uridine |
| modified cytidine having one or more nucleobases of Formula (b32) | modified cytidine with (b32)/pseudouridine |
| | modified cytidine with (b32)/N1-methyl-pseudouridine |
| | modified cytidine with (b32)/5-methoxy-uridine |
| | modified cytidine with (b32)/5-methyl-uridine |
| | modified cytidine with (b32)/5-bromo-uridine |
| | modified cytidine with (b32)/2-thio-uridine |
| | about 50% of cytidine substituted with modified cytidine (b32)/about 50% of uridines are 2-thio-uridine |
| modified cytidine having one or more nucleobases of Formula (b1) | modified uridine with (b1)/N4-acetyl-cytidine |
| | modified uridine with (b1)/5-methyl-cytidine |
| modified cytidine having one or more nucleobases of Formula (b8) | modified uridine with (b8)/N4-acetyl-cytidine |
| | modified uridine with (b8)/5-methyl-cytidine |
| modified cytidine having one or more nucleobases of Formula (b28) | modified uridine with (b28)/N4-acetyl-cytidine |
| | modified uridine with (b28)/5-methyl-cytidine |
| modified cytidine having one or more nucleobases of Formula (b29) | modified uridine with (b29)/N4-acetyl-cytidine |
| | modified uridine with (b29)/5-methyl-cytidine |
| modified cytidine having one or more nucleobases of Formula (b30) | modified uridine with (b30)/N4-acetyl-cytidine |
| | modified uridine with (b30)/5-methyl-cytidine |

In some embodiments, at least 25% of the cytosines are replaced by a compound of Formula (b10)-(b14) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the uracils are replaced by a compound of Formula (b1)-(b9) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the cytosines are replaced by a compound of Formula (b10)-(b14), and at least 25% of the uracils are replaced by a compound of Formula (b1)-(b9) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* 3*rd Ed.* (Plenum Press) Vols A and B(1992).

Example 1

DNA Template with GCSF Gene

Figure 5:
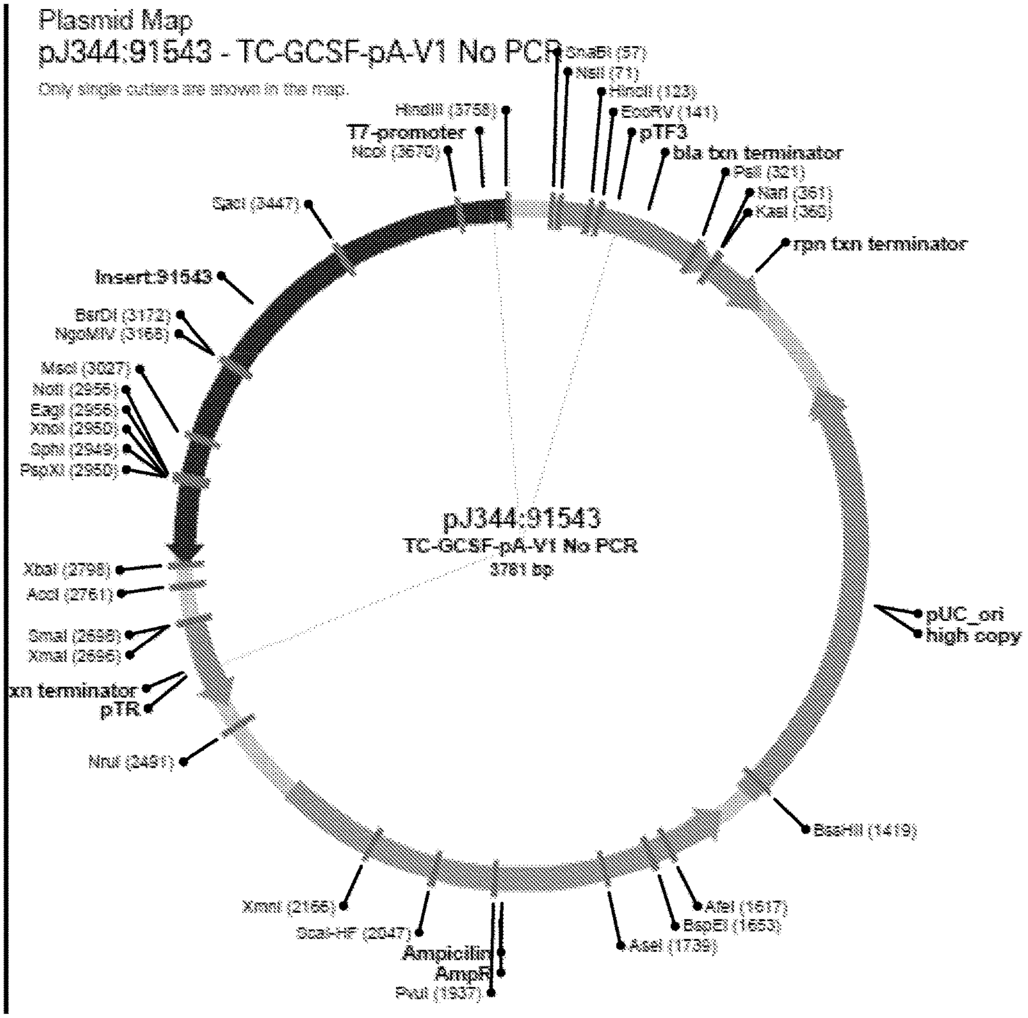
FIG. 5 is a map of plasmid pJ344:91543-TC-GCSF-pA-V1, according to one embodiment.

The plasmid pJ344:91543-TC-GCSF includes the coding sequence for GCSF (granulyte colony stimulating factor) and 141 nucleotide sequence coding for Poly A Tail and an XBaI restriction endonuclease recognition site immediately downstream of the poly A tail sequence tract. A plasmid map is shown in FIG. 5, and a plasmid DNA sequence is shown in FIG. 6.

An *E. coli* strain DH10B harboring above plasmid was grown in 250 ml animal-free broth with ampicillin. This process generated 1107 μg of plasmid DNA. The plasmid DNA was isolated and purified according to DNA2.0 standard operating procedures. Plasmid DNA yield and DNA homogeneity was determined using agarose gel electrophoresis. The insert (but not vector backbone) was sequence verified in both orientations using a capillary electrophoresis DNA analyzer.

Example 2

Linearization of DNA Template

The plasmid DNA template was linearized using the restriction endonuclease XbaI. The XbaI restriction digest reaction conditions were as follows:

| | |
|---|---|
| Water | 25573.6 μL |
| Plasmid DNA (1145 μg/μL | 1879.9 μL |
| BSA (100X) | 430.5 μL |
| Buffer 4 (10X) | 4305.0 μL |
| XbaI (20000 U/ml | 861 μL |
| Total vol | 43050 μL |

The reaction proceeded at 37° C. overnight. The linearized plasmid was diafiltered into 10 mM Tris HCl pH 7.5 and concentrated to 959 ng/uL prior to use using 100 kDa MWCO Amicon spin filters (EMD Millipore).

Example 3

In Vitro Transcription

The non-amplified, linearized DNA plasmid was used as a template for in vitro transcription. A 1 mL transcription reaction was performed utilizing 250 μg of plasmid template. Nucleotides ATP, GTP, 5mCTP (5-methyl cytosine triphosphate) and N-1-methylpseudouridine triphosphate were added at 7.5 mM each. RNase inhibitor (1000 U), inorganic pyrophosphatase (1U) and T7 RNA polymerase (7000U) were added. The final buffer conditions (1×) were as follows: 40 mM Tris HCl pH8, 40 mM magnesium acetate, 5 mM dithiothreitol (DTT), and 1 mM spermidine.

The in vitro transcription reaction proceeded for 4 hours at 37° C. under constant mixing. The total reaction yield was 5.4 mg RNA transcript. A 400 uL (40%) portion of the reaction was diafiltered into water and concentrated to 622 ng/μL using 100 kDa MWCO Amicon spin filters (EMD Millipore).

The results demonstrate successful, milligram scale production of RNA transcript with in vitro transcription using a non-PCT amplified, linearized plasmid DNA template.

Example 4

Oligo dT Removal of DNA Template

The full length poly A containing RNA transcript was purified from truncated RNA, DNA template, and residual enzymes using oligo dT chromatography. A 20 mer polythymidine Sepharose (3 ml) was packed in a 5 mL SPE column on a solid phase extraction vacuum manifold. The RNA transcript (2.18 mg) was applied to column, followed by washing and elution. The oligo dT purified RNA transcript was diafiltered into water and concentrated to 1.22 mg/mL using 100 kDa MWCO Amicon spin filters (EMD Millipore). Approximately 1.82 mg of 2.18 mg was recovered (83%) as determined by Bioanalyzer gel elctrophoresis.

Example 5

Characterization of Uncapped RNA Transcript, Pre and Post Oligo dT

Figure 7A:
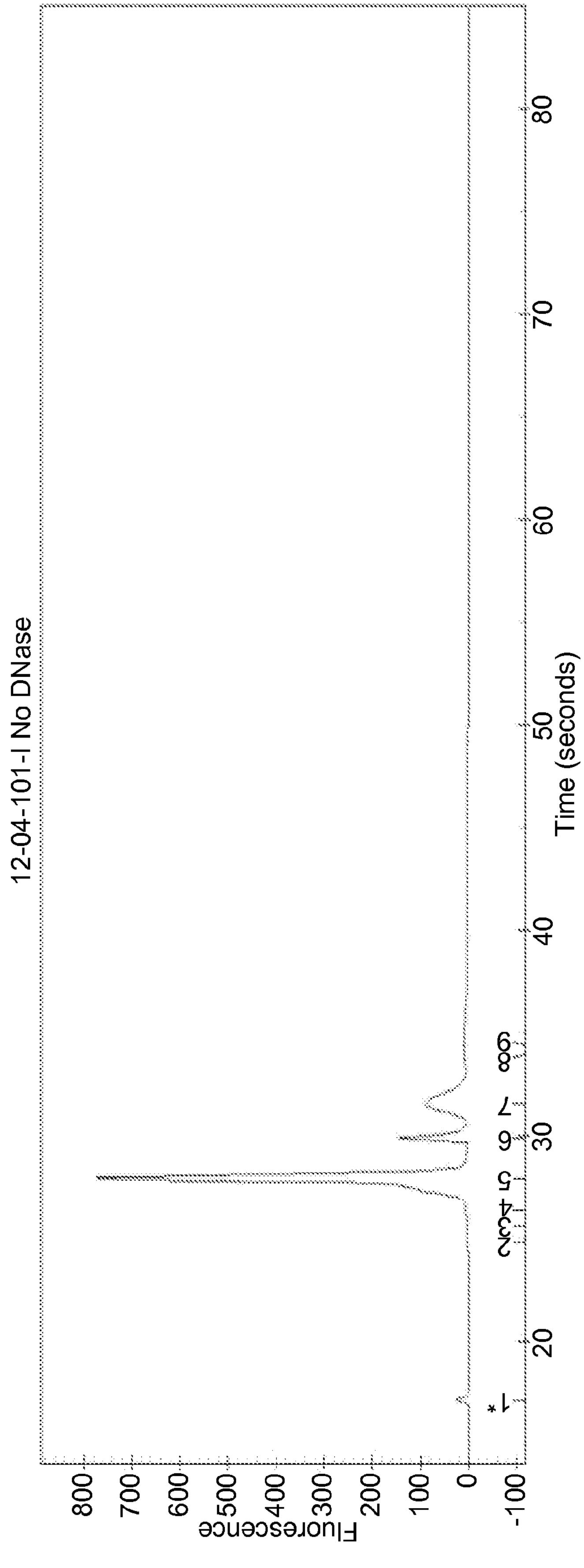
FIGS. 7A and 7B are electropherograms of RNA transcripts, according to one embodiment.
Figure 7B:
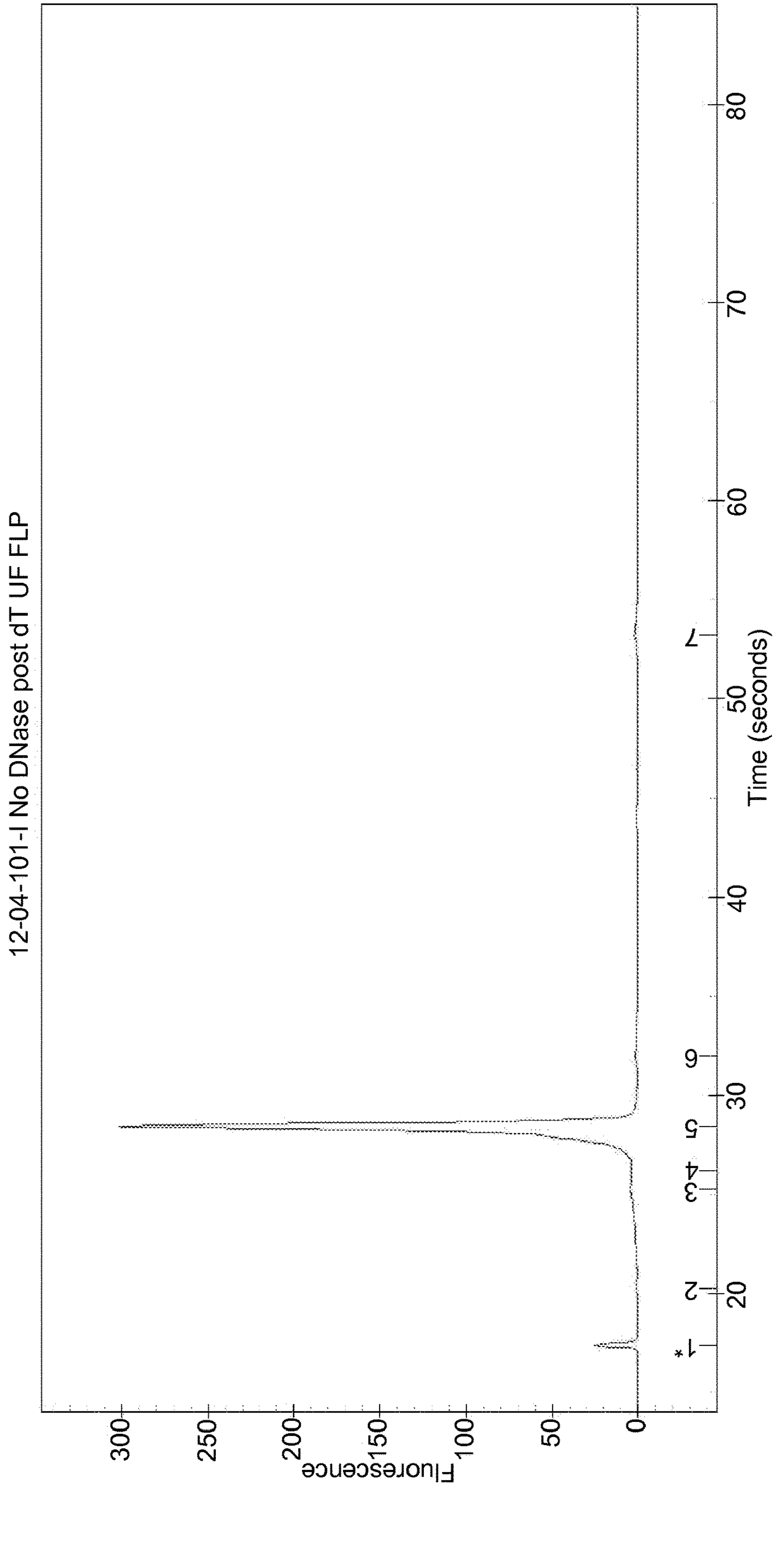

The RNA transcript was analyzed using a Bioanalyzer gel electrohphoresis. Sample taken both before and after oligo dT purification were analyzed. The results are shown in the electopherograms in FIGS. 7A and 7B.

The results demonstrate recovery of >80% RNA transcript using oligo dT purification and virtual elimination of impurities.

Example 6

Capping of RNA Transcript

A 5' cap was enzymatically added to the RNA transcript. Approximately 0.98 mg of oligo dT purified RNA transcript (1225 ng/uL) was capped to obtain a 5' Cap 1 structure. GTP was added at a final reaction concentration of 0.9 mM. SAM (S-adenosyl-L-methionine) was added at a final reaction concentration of 0.4 mM. 907 units of RNase inhibitor, 3630 units of 2'O-methyltransferase, and 363 units of vaccinia guanylyltransferase were added to the reaction. The final 1× buffer conditions consist of the following: 50 mM Tris HCl pH 8, 5 mM KCl, 1 mM MgCl2, and 1 mM dithiothreitol. Final reaction volume was 1070 µL. The reaction proceeded at 37° C. for 2 hours under constant mixing. Reaction setup for capped RNA (lot 12-04-155-C) is shown below.

| mRNA Capping Worksheet (Molar Calc) | | | | | | |
|---|---|---|---|---|---|---|
| Total RNA | | | 10X Capping Buffer | Conc(mM) | | |
| mRNA length | 1.5 | mg | Tris HCl pH8 | 500 | | |
| mRNA MW | 900 | Bases | KCl | 50 | | |
| mRNA (amt) | 306,000 Da | | MgCl2 | 10 | | |
| mRNA amount | 0.0049 umol | | DTT | 10 | | |
| | 4.90 nmol | | | | | |
| Target Final mRNA Conc in RXN | 3.64 uM | | | | | |
| Target RXN Volume | 1348 uL | | | | | |
| mRNA Volume | 971 uL | | | | | |
| Target mRNA Conc: | 1.55 mg/mL | | | | | |
| Target mRNA Conc: | 1546 ng/uL | | | | | |
| Acceptable Range (+/- 5%) | 1468 ng/uL | to | 1623 ng/uL | | | |
| | Stock conc | Volume | | Stoichiometry | | Effective Conc: |
| 10X Capping Buffer | | 134.8 uL | | | | |
| GTP | 100 mM | 13.5 uL | | 275.2:1 mol/mol | | 100 mM |
| SAM | 20 mM | 33.8 uL | | 137.8:1 mol/mol | | 0.50 mM |
| | Stock conc | Volume | | | Total Units | Effective Conc: |
| Rnase Inhibitor | 40000 U/mL | 33.7 uL | | 275 U/nmol | 1348.0 Units | 1000 U/mL |
| 2'Ome Transferase | 50000 U/mL | 107.9 uL | | 1100.2 U/nmol | 5393.1 Units | 4001 U/mL |
| Vaccinia Cap | 10000 U/mL | 53.9 uL | | 109.9 U/nmol | 538.7 Units | 400 U/mL1 |
| Mastermix Volume | 378 uL | | | | | |
| mRNA Volume | 971 uL | | | | | |
| Total Volume | 1348 uL | | | | | |

The projected sequence of the RNA transcript is below:

```
mRNA Sequence: 12-04-101-I and 12-04-111-I
(Capped: 12-04-154-C) and 12-04-155-C)
Parent Gene ID 91543 and 103294
5' G*GGGAAAUAAG AGAGAAAAGA AGAGUAAGAA GAAAUAUAAG

AGCCACCAUG GCCGGUCCCG CGACCCAAAG CCCCAUGAAA

CUUAUGGCCC UGCAGUUGCU GCUUUGGCAC UCGGCCCUCU

GGACAGUCCA AGAAGCGACU CCUCUCGGAC CUGCCUCAUC

GUUGCCGCAG UCAUUCCUUU UGAAGUGUCU GGAGCAGGUG

CGAAAGAUUC AGGGCGAUGG AGCCGCACUC CAAGAGAAGC

UCUGCGCGAC AUACAAACUU UGCCAUCCCG AGGAGCUCGU

ACUGCUCGGG CACAGCUUGG GGAUUCCCUG GGCUCCUCUC

UCGUCCUGUC CGUCGCAGGC UUUGCAGUUG GCAGGGUGCU

UUUCCCAGCU CCACUCCGGU UUGUUCUUGU AUCAGGGACU

GCUGCAAGCC CUUGAGGGAA UCUCGCCAGA AUUGGGCCCG

ACGCUGGACA CGUUGCAGCU CGACGUGGCG GAUUUCGCAA

CAACCAUCUG GCAGCAGAUG GAGGAACUGG GGAUGGCACC

CGCGCUGCAG CCCACGCAGG GGGCAAUGCC GGCCUUUGCG

UCCGCGUUUC AGCGCAGGGC GGGUGGAGUC CUCGUAGCGA

GCCACCUUCA AUCAUUUUUG GAAGUCUCGU ACCGGGUGCU

GAGACAUCUU GCGCAGCCGU GAUAAGCUGC CUUCUGCGGG

GCUUGCCUUC UGGCCAUGCC CUUCUUCUCU CCCUUGCACC

UGUACCUCUU GGUCUUUGAA UAAAGCCUGA GUAGGAAGGC

GGCCGCUCGA GCAUGCAAAA AAAAAAAAAA AAAAAAAAAA

AAAAAAAAAA AAAAAAAAAA AAAAAAAAAA AAAAAAAAAA

AAAAAAAAAA AAAAAAAAAA AAAAAAAAAA AAAAAAAAAA

AAAAAAAAAA AAAAAAAAAA AAAAAAAAAA AAAAAAAUCU

AG 3'
G* = cap
```

Example 7

Oligo dT Purification of Capped RNA Transcript

Figure 8:
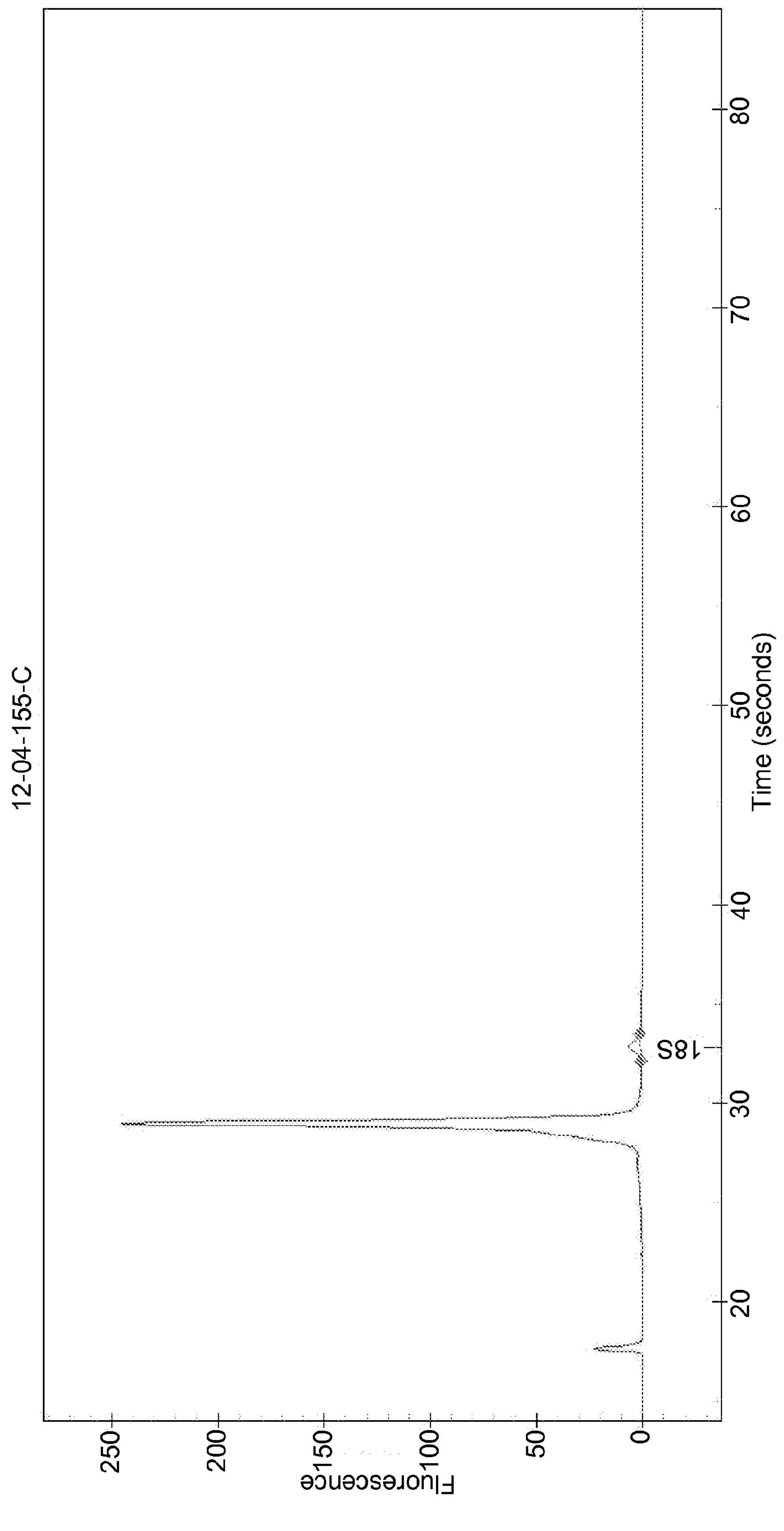
FIG. 8 is an electropherogram of capped RNA, according to one embodiment.

The capped RNA transcript was purified using 2 mL of 20mer polythymidine Sepharose packed in a 5 mL SPE column on a solid phase extraction vacuum manifold. 0.82 mg was recovered in the elution (84% recovery) The RNA was diafiltered into water and harvested at a concentration of 366 ng/uL using 100 kDa MWCO Amicon spin filters (EMD Millipore). The results are shown in FIG. 8.

Example 8

Figure 9:
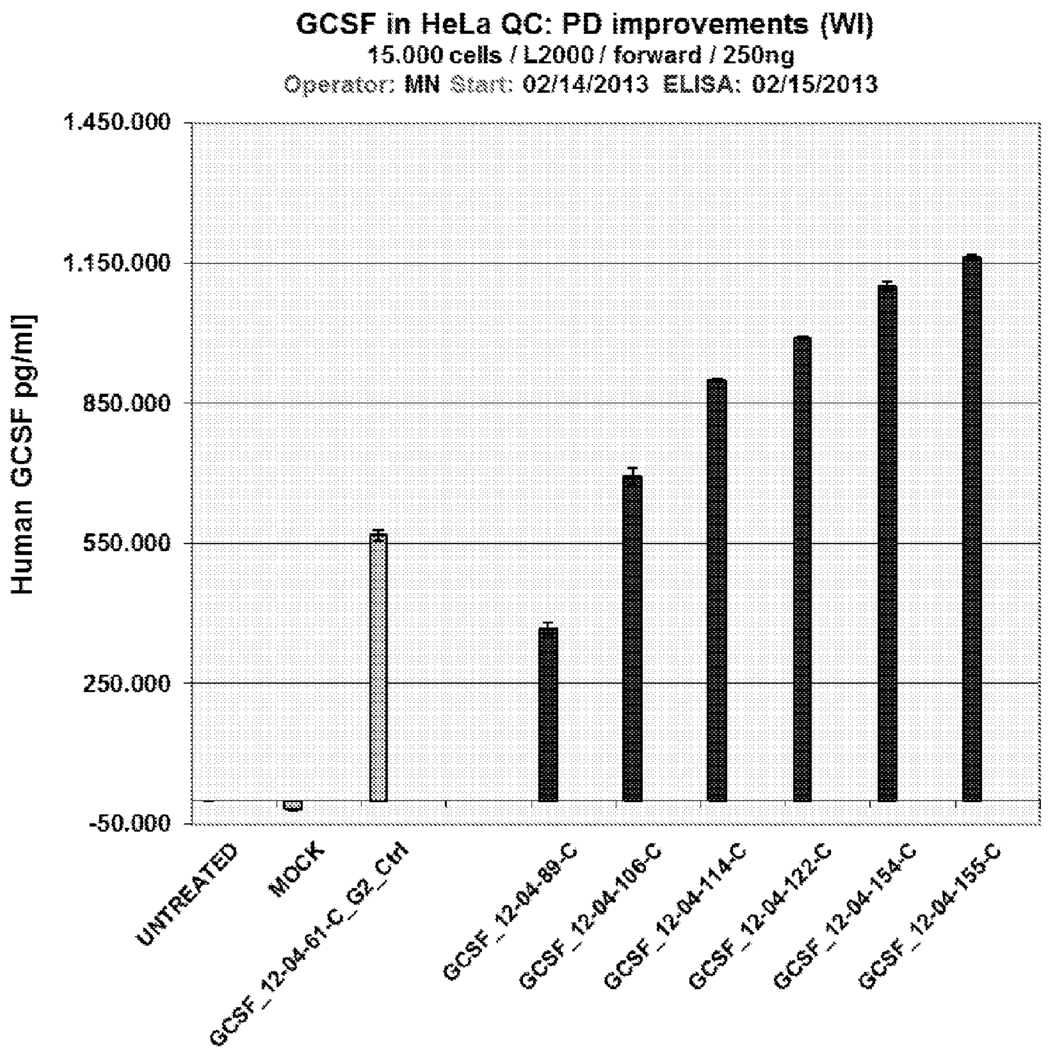
FIG. 9 illustrates a bar graph showing results of an ELISA used to quantify expressed protein data, according to one embodiment.

Protein Expression Using Capped RNA Transcript Produced by the Method of the Invention Assessment of protein expression was conducted via forward transfection of RNA into HeLa cells. GCSF ELISA was used to quantify expressed protein ELISA data; data are shown in FIG. 9.

12-04-155-C produced using a linearized Poly A:T tract DNA template and enzymatic capping yielded ~1,150 ng/mL GCSF expression, significantly higher than the four lots that utilized PCR product as a DNA template: 12-04-89-C, 12-04-106-C, 12-04-114-C, and 12-04-122-C.

Example 9

Figure 10:
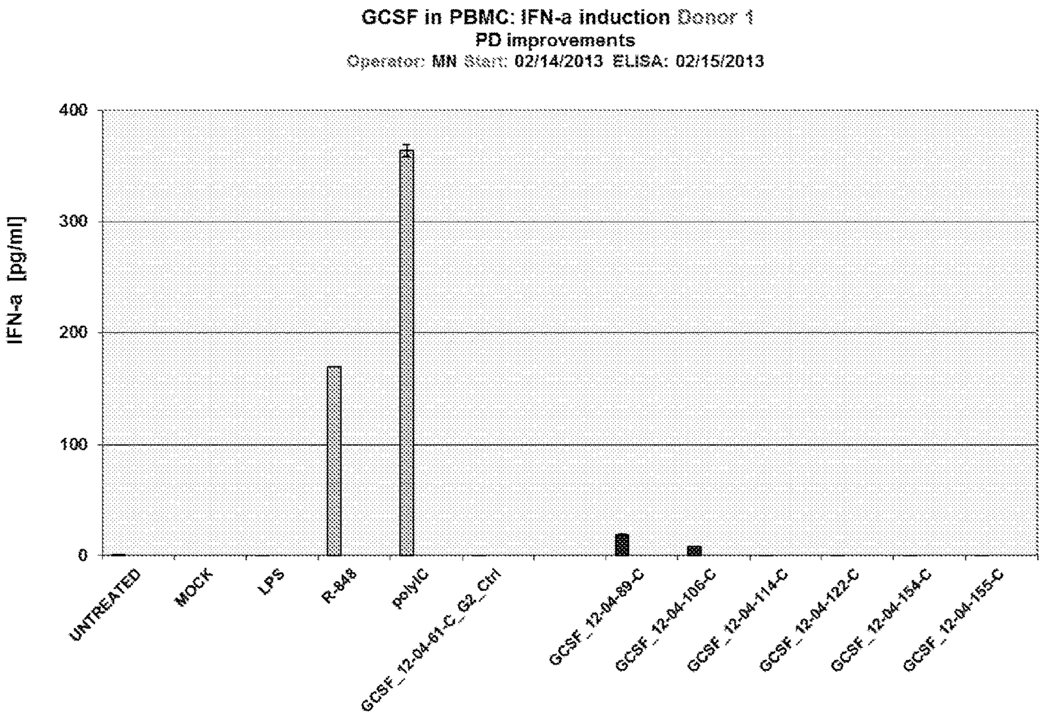
FIG. 10 illustrates a bar graph showing results of an assay for determination of IFN-α induction following transfection of RNAs into PBMC, according to one embodiment.

Interferon-a Induction Assessment Using Capped RNA Transcript Produced by the Method of the Invention RNAs were transfected into Peripheral blood mononuclear cells (PBMC) to assay in vitro cytokine induction. The results are shown in FIG. 10. The RNA transcript 12-04-155-C produced using a linearized Poly A:T tract DNA template and enzymatic capping resulted in undetectable levels of interferon-α as determined by IFN-α ELISA. In contrast, two of four samples that utilized PCR product as a DNA template: 12-04-89-C, 12-04-106-C showed some level of interferon-α induction. Poly IC (Polyinosinic:polycytidylic acid) is an immune stimulatory positive control and R-848 is an imidazoquinoline compound that is also used as a positive control.

Example 10

DNA Template with Factor IX Gene

The plasmid pJ204109475 includes the coding sequence for Factor IX and 141 nucleotide sequence coding for Poly A Tail and an SapI restriction endonuclease recognition site immediately downstream of the poly A tail sequence tract.

Figure 11A:
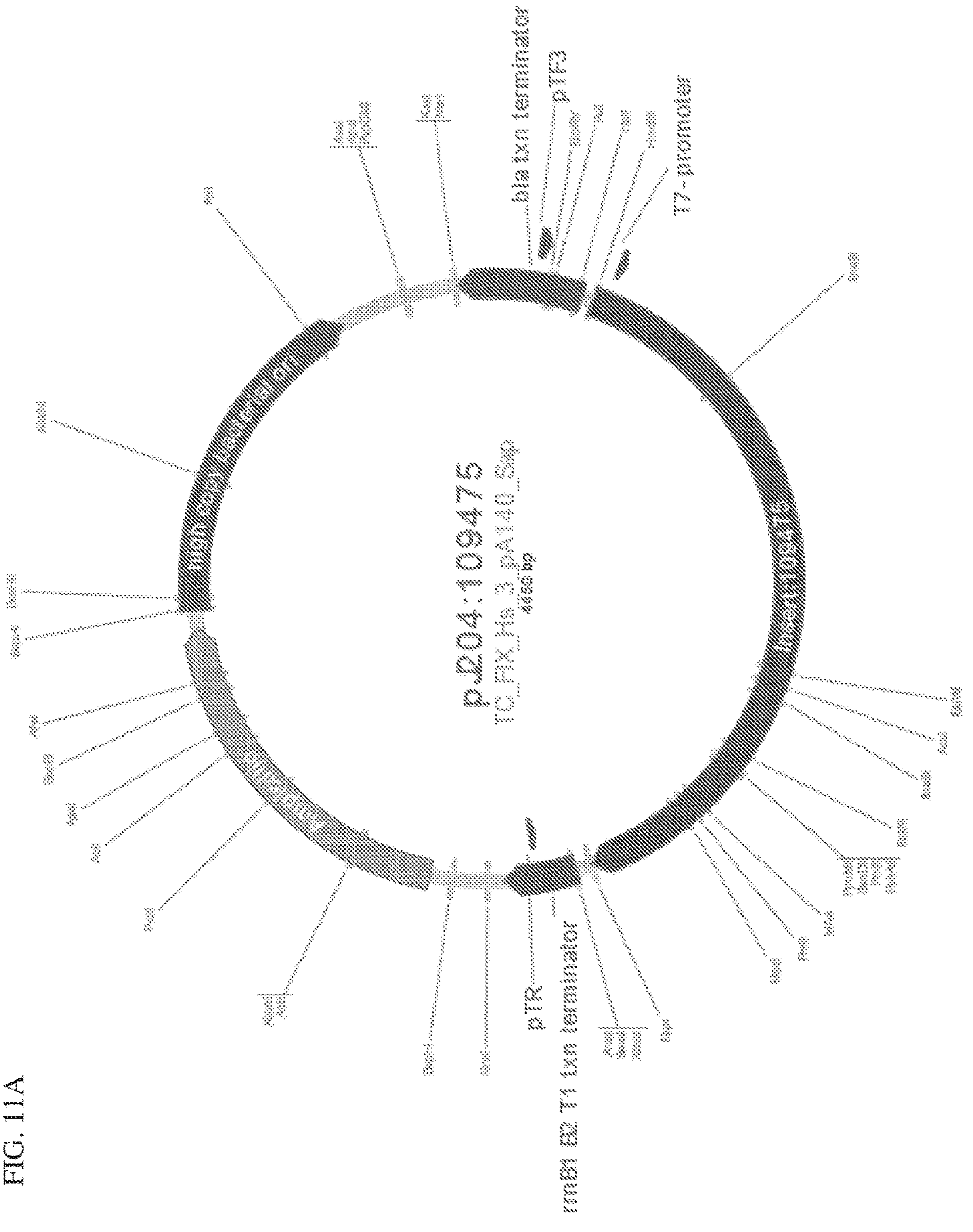
FIG. 11A is a map of plasmid pJ204:109475-TC-FIX-Hs-3-pA140-Sap, according to one embodiment.

A plasmid map and DNA sequence are shown in FIGS. 11A and 11B.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method for producing a purified composition comprising a capped RNA transcript for a gene of interest, the method comprising:

(a) providing a sample comprising a linear, non-amplified DNA template, the DNA template comprising an RNA polymerase promoter sequence operatively linked to a target sequence coding for the gene of interest, a poly A tail sequence of 60-160 nucleotides, an endonuclease recognition site sequence immediately downstream of the poly A tail sequence, and a 5' untranslated region (UTR) and/or a 3' UTR;

(b) contacting the sample with a RNA polymerase and ribonucleotides under conditions sufficient for vitro transcription to produce a first composition comprising an uncapped RNA transcript wherein at least 80% of the RNA transcript is full-length uncapped RNA transcript;

(c) purifying the uncapped RNA transcript using oligo dT affinity purification;

(d) capping the uncapped RNA transcript by contacting the RNA transcript with quanlyltransferase, s-adenosyl-L-methionine, guanosine triphosphate, and 2'-O-methyltransferase to produce a second composition comprising a capped RNA transcript;

(e) purifying the capped RNA transcript from the second composition by anion exchange chromatography; and (f) filtering the capped RNA transcript by ultrafiltration or tangential flow filtration, thereby producing the purified composition comprising a capped RNA transcript, wherein the method does not comprise treating the composition with DNase.

2. The method of claim 1, wherein at least at least 95% of the uncapped RNA transcript in the first composition is full-length uncapped RNA transcript.

3. The method of claim 1, wherein the percent full length uncapped RNA transcript is determined by reverse phase HPLC and measured by peak area of full length relative to total peak area.

4. The method of claim 1, wherein the method does not comprise a polymerase chain reaction (PCR) amplification step.

5. The method of claim 1, wherein the endonuclease recognition site sequence is recognized by Xbal or Sapl.

6. The method of claim 1, wherein the method further comprises producing the DNA template, wherein producing the DNA template comprises contacting a circular plasmid DNA template with an endonuclease that recognizes the endonuclease recognition site sequence.

7. The method of claim 6, wherein the method further comprises producing the circular plasmid DNA template at a microgram scale, a milligram scale, or a gram scale.

8. The method of claim 1, wherein the RNA polymerase is a T7polymerase.

9. The method of claim 1, wherein at least one nucleotide is a modified nucleotide.

* * * * *

SEQUENCE LISTING

```
<160> NUMBER OF SEQ ID NOS: 13

<210> SEQ ID NO 1
<211> LENGTH: 923
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1

ggggaaauaa gagagaaaag aagaguaaga agaaauauaa gagccaccau ggccggucce     60

gcgacccaaa gccccaugaa acuuauggcc cugcaguugc ugcuuuggca cucggcccuc    120

uggacagucc aagaagcgac uccucucgga ccugccucau cguugccgca gucauuccuu    180

uugaaguguc uggagcaggu gcgaaagauu cagggcgaug gagccgcacu ccaagagaag    240

cucugcgcga cauacaaacu uugccauccc gaggagcucg uacugcucgg gcacagcuug    300

gggauucccu gggcuccucu cucguccugu ccgucgcagg cuuugcaguu ggcagggugc    360

cuuucccagc uccacuccgg uuuguucuug uaucagggac ugcugcaagc ccuugaggga    420

aucucgccag aauugggccc gacgcuggac acguugcagc ucgacguggc ggauuucgca    480

acaaccaucu ggcagcagau ggaggaacug ggauggcac ccgcgcugca gcccacgcag    540

ggggcaaugc cggccuuugc guccgcguuu cagcgcaggg cggguggagu ccucguagcg    600

agccaccuuc aaucauuuuu ggaagucucg uaccgggugc ugagacaucu ugcgcagccg    660

ugauaagcug ccuucugcgg ggcuugccuu cuggccaugc ccuucuucuc ucccuugcac    720

cuguaccucu uggucuuuga auaaagccug aguaggaagg cggccgcucg agcaugcaaa    780

aaaaaaaaaa aaaaaaaaaa aaaaaaaaaa aaaaaaaaaa aaaaaaaaaa aaaaaaaaaa    840

aaaaaaaaaa aaaaaaaaaa aaaaaaaaaa aaaaaaaaaa aaaaaaaaaa aaaaaaaaaa    900
```

-continued aaaaaaaaaa aaaaaaaauc uag 923

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2
aaaaaaaaaa tctaga 16

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 3
aaaaaaaaaa gaagagc 17

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 4
tctagatttt tttttt 16

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5
gctcttcttt ttttttt 17

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
aaaaaaaaaa t 11

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
ctagattttt ttttt 15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaaaaaaaaa tctag 15

<210> SEQ ID NO 9
<211> LENGTH: 3781
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ggtctcctat acgtctctta tacgacatca ccgatgggga acccagacgc tgagtacgta 60
ttctaaatgc ataataaata ctgataacat cttatagttt gtattatatt ttgtattatc 120
gttgacatgt ataattttga tatcaaaaac tgattttccc tttattattt tcgagattta 180
ttttcttaat tctctttaac aaactagaaa tattgtatat acaaaaaatc ataaataata 240
gatgaatagt ttaattatag gtgttcatca atcgaaaaag caacgtatct tatttaaagt 300
gcgttgcttt tttctcattt ataaggttaa ataattctca tatatcaagc aaagtgacag 360
gcgcccttaa atattctgac aaatgctctt tccctaaact ccccccataa aaaaacccgc 420
cgaagcgggt ttttacgtta tttgcggatt aacgattact cgttatcaga accgcccagg 480
gggcccgagc ttaagactgg ccgtcgtttt acaacacaga aagagtttgt agaaacgcaa 540
aaaggccatc cgtcaggggc cttctgctta gtttgatgcc tggcagttcc ctactctcgc 600
cttccgcttc ctcgctcact gactcgctgc gctcggtcgt tcggctgcgg cgagcggtat 660
cagctcactc aaaggcggta atacggttat ccacagaatc aggggataac gcaggaaaga 720
acatgtgagc aaaaggccag caaaaggcca ggaaccgtaa aaaggccgcg ttgctggcgt 780
ttttccatag gctccgcccc cctgacgagc atcacaaaaa tcgacgctca agtcagaggt 840
ggcgaaaccc gacaggacta taaagatacc aggcgtttcc ccctggaagc tccctcgtgc 900
gctctcctgt tccgaccctg ccgcttaccg gatacctgtc cgcctttctc ccttcgggaa 960
gcgtggcgct ttctcatagc tcacgctgta ggtatctcag ttcggtgtag gtcgttcgct 1020
ccaagctggg ctgtgtgcac gaaccccccg ttcagcccga ccgctgcgcc ttatccggta 1080
actatcgtct tgagtccaac ccggtaagac acgacttatc gccactggca gcagccactg 1140
gtaacaggat tagcagagcg aggtatgtag gcggtgctac agagttcttg aagtggtggg 1200
ctaactacgg ctacactaga agaacagtat ttggtatctg cgctctgctg aagccagtta 1260
ccttcggaaa aagagttggt agctcttgat ccggcaaaca aaccaccgct ggtagcggtg 1320
gtttttttgt ttgcaagcag cagattacgc gcagaaaaaa aggatctcaa gaagatcctt 1380
tgatcttttc tacggggtct gacgctcagt ggaacgacgc gcgcgtaact cacgttaagg 1440
gattttggtc atgagcttgc gccgtcccgt caagtcagcg taatgctctg cttttaccaa 1500
tgcttaatca gtgaggcacc tatctcagcg atctgtctat ttcgttcatc catagttgcc 1560
tgactccccg tcgtgtagat aactacgata cgggagggct taccatctgg ccccagcgct 1620

```
gcgatgatac cgcgagaacc acgctcaccg gctccggatt tatcagcaat aaaccagcca   1680

gccggaaggg ccgagcgcag aagtggtcct gcaactttat ccgcctccat ccagtctatt   1740

aattgttgcc gggaagctag agtaagtagt tcgccagtta atagtttgcg caacgttgtt   1800

gccatcgcta caggcatcgt ggtgtcacgc tcgtcgtttg gtatggcttc attcagctcc   1860

ggttcccaac gatcaaggcg agttacatga tcccccatgt tgtgcaaaaa agcggttagc   1920

tccttcggtc ctccgatcgt tgtcagaagt aagttggccg cagtgttatc actcatggtt   1980

atggcagcac tgcataattc tcttactgtc atgccatccg taagatgctt ttctgtgact   2040

ggtgagtact caaccaagtc attctgagaa tagtgtatgc ggcgaccgag ttgctcttgc   2100

ccggcgtcaa tacgggataa taccgcgcca catagcagaa ctttaaaagt gctcatcatt   2160

ggaaaacgtt cttcggggcg aaaactctca aggatcttac cgctgttgag atccagttcg   2220

atgtaaccca ctcgtgcacc caactgatct tcagcatctt ttactttcac cagcgtttct   2280

gggtgagcaa aaacaggaag gcaaaatgcc gcaaaaaagg gaataagggc gacacggaaa   2340

tgttgaatac tcatattctt cctttttcaa tattattgaa gcatttatca gggttattgt   2400

ctcatgagcg gatacatatt tgaatgtatt tagaaaaata aacaaatagg ggtcagtgtt   2460

acaaccaatt aaccaattct gaacattatc gcgagcccat ttatacctga atatggctca   2520

taacacccct tgtttgcctg gcggcagtag cgcggtggtc ccacctgacc ccatgccgaa   2580

ctcagaagtg aaacgccgta gcgccgatgg tagtgtgggg actccccatg cgagagtagg   2640

gaactgccag gcatcaaata aaacgaaagg ctcagtcgaa agactgggcc tttcgcccgg   2700

gctaattagg ggggctggat cgcttcgtgt tccccatcgg tgatgtcgta taggaagcag   2760

tatacgagac ctataggaga cgtatatggt cttcttttct agattttttt tttttttttt   2820

tttttttttt tttttttttt tttttttttt tttttttttt tttttttttt tttttttttt   2880

tttttttttt tttttttttt tttttttttt tttttttttt tttttttttt tttttttttt   2940

ttttgcatgc tcgagcggcc gccttcctac tcaggcttta ttcaaagacc aagaggtaca   3000

ggtgcaaggg agagaagaag ggcatggcca gaaggcaagc cccgcagaag gcagcttatc   3060

acggctgcgc aagatgtctc agcacccggt acgagacttc caaaaatgat tgaaggtggc   3120

tcgctacgag gactccaccc gccctgcgct gaaacgcgga cgcaaaggcc ggcattgccc   3180

cctgcgtggg ctgcagcgcg ggtgccatcc ccagttcctc catctgctgc cagatggttg   3240

ttgcgaaatc cgccacgtcg agctgcaacg tgtccagcgt cgggcccaat tctggcgaga   3300

ttccctcaag ggcttgcagc agtccctgat acaagaacaa accggagtgg agctgggaaa   3360

ggcaccctgc caactgcaaa gcctgcgacg gacaggacga gagaggagcc cagggaatcc   3420

ccaagctgtg cccgagcagt acgagctcct cgggatggca aagtttgtat gtcgcgcaga   3480

gcttctcttg gagtgcggct ccatcgccct gaatctttcg cacctgctcc agacacttca   3540

aaaggaatga ctgcggcaac gatgaggcag gtccgagagg agtcgcttct tggactgtcc   3600

agagggccga gtgccaaagc agcaactgca gggccataag tttcatgggg ctttgggtcg   3660

cgggaccggc catggtggct cttatatttc ttcttactct tcttttctct cttatttccc   3720

tatagtgagt cgtattagct tctgtacgag ggtccaaaag cttgaccccg aagacactat   3780

a                                                                   3781
```

<210> SEQ ID NO 10
<211> LENGTH: 4450
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10

```
aaaagatcaa aggatcttct tgagatcctt tttttctgcg cgtaatctgc tgcttgcaaa     60
caaaaaaacc accgctacca gcggtggttt gtttgccgga tcaagagcta ccaactcttt    120
ttccgaaggt aactggcttc agcagagcgc agataccaaa tactgttctt ctagtgtagc    180
cgtagttagc ccaccacttc aagaactctg tagcaccgcc tacatacctc gctctgctaa    240
tcctgttacc agtggctgct gccagtggcg ataagtcgtg tcttaccggg ttggactcaa    300
gacgatagtt accggataag gcgcagcggt cgggctgaac ggggggttcg tgcacacagc    360
ccagcttgga gcgaacgacc tacaccgaac tgagatacct acagcgtgag ctatgagaaa    420
gcgccacgct tcccgaaggg agaaaggcgg acaggtatcc ggtaagcggc agggtcggaa    480
caggagagcg cacgagggag cttccagggg gaaacgcctg gtatctttat agtcctgtcg    540
ggtttcgcca cctctgactt gagcgtcgat ttttgtgatg ctcgtcaggg gggcggagcc    600
tatggaaaaa cgccagcaac gcggcctttt tacggttcct ggccttttgc tggccttttg    660
ctcacatgtt ctttcctgcg ttatcccctg attctgtgga taaccgtatt accgcctttg    720
agtgagctga taccgctcgc cgcagccgaa cgaccgagcg cagcgagtca gtgagcgagg    780
aagcggaagg cgagagtagg gaactgccag gcatcaaact aagcagaagg cccctgacgg    840
atggcctttt tgcgtttcta caaactcttt ctgtgttgta aaacgacggc cagtcttaag    900
ctcgggcccc ctgggcggtt ctgataacga gtaatcgtta atccgcaaat aacgtaaaaa    960
cccgcttcgg cgggtttttt tatgggggga gtttagggaa agagcatttg tcagaatatt   1020
taagggcgcc tgtcactttg cttgatatat gagaattatt taaccttata aatgagaaaa   1080
aagcaacgca ctttaaataa gatacgttgc tttttcgatt gatgaacacc tataattaaa   1140
ctattcatct attatttatg atttttttgta tatacaatat ttctagtttg ttaaagagaa  1200
ttaagaaaat aaatctcgaa aataataaag ggaaaatcag tttttgatat caaaattata   1260
catgtcaacg ataatacaaa atataataca aactataaga tgttatcagt atttattatg   1320
catttagaat aaattttgtg tcgcccttcg ctgaatcaag cttttggacc ctcgtacaga   1380
agctaatacg actcactata gggaaataag agagaaaaga agagtaagaa gaaatataag   1440
agccaccatg cagcgcgtca acatgattat ggccgaatcg ccgggactca tcacaatctg   1500
cctcttgggt tatctcttgt cggcagaatg taccgtgttc ttggatcacg aaaacgcgaa   1560
caaaattctt aatcgcccga agcggtataa ctccgggaaa cttgaggagt ttgtgcaggg   1620
caatcttgaa cgagagtgca tggaggagaa atgctccttt gaggaggcga gggaagtgtt   1680
tgaaaacaca gagcgaacaa cggagttttg gaagcaatac gtagatgggg accagtgtga   1740
gtcgaatccg tgcctcaatg gggatcatg taaagatgac atcaatagct atgaatgctg    1800
gtgcccgttt gggtttgaag ggaagaactg tgagctggat gtgacgtgca acatcaaaaa   1860
cggacgctgt gagcagtttt gtaagaactc ggctgacaat aaggtagtat gctcgtgcac   1920
agagggatac cggctggcgg agaaccaaaa atcgtgcgag cccgcagtcc cgttcccttg   1980
tgggagggtg agcgtgtcac agactagcaa gttgacgaga gcggagactg tattccccga   2040
cgtggactac gtcaacagca ccgaagccga aacaatcctc gataacatca cgcagagcac   2100
tcagtccttc aatgacttta cgagggtcgt aggtggtgag gacgcgaaac ccggtcagtt   2160
cccctggcag gtggtattga acggaaaagt cgatgccttt tgtggaggtt ccattgtcaa   2220
```

```
cgagaagtgg attgtcacag cggcacactg cgtagaaaca ggagtgaaaa tcacggtagt   2280
ggcgggagag cataacattg aagagacaga gcacacggaa caaaagcgaa atgtcatcag   2340
aatcattcca caccataact ataacgcggc aatcaataag tacaatcacg acatcgcact   2400
tttggagctt gacgaacctt tggtgcttaa ttcgtacgtc acccctattt gtattgccga   2460
caaagagtat acaaacatct tcttgaaatt cggctccggg tacgtatcgg gctggggcag   2520
agtgttccat aagggtagat ccgcactggt gttgcaatac ctcagggtgc ccctcgtgga   2580
tcgagccact tgtctgcggt ccaccaaatt cacaatctac aacaatatgt tctgtgcggg   2640
attccatgaa ggtgggagag atagctgcca gggagactca gggggtcccc acgtgacgga   2700
agtcgagggg acgtcatttc tgacgggaat tatctcatgg ggagaggaat gtgcgatgaa   2760
ggggaaatat ggcatctaca ctaaagtgtc acggtatgtc aattggatca aggaaaagac   2820
gaaactcacg tgataatagg ctggagcctc ggtggccatg cttcttgccc cttgggcctc   2880
cccccagccc ctcctcccct tcctgcaccc gtacccccgt ggtctttgaa taaagtctga   2940
gtgggcggca aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaag aagagccgtc aatcgagttc gtacctaagg   3120
gcgacacccc ataattagcc cgggcgaaag gcccagtctt tcgactgagc ctttcgtttt   3180
atttgatgcc tggcagttcc ctactctcgc atggggagtc cccacactac catcggcgct   3240
acggcgtttc acttctgagt tcggcatggg gtcaggtggg accaccgcgc tactgccgcc   3300
aggcaaacaa ggggtgttat gagccatatt caggtataaa tgggctcgcg ataatgttca   3360
gaattggtta attggttgta acactgaccc ctatttgttt atttttctaa atacattcaa   3420
atatgtatcc gctcatgaga caataaccct gataaatgct tcaataatat tgaaaaagga   3480
agaatatgag tattcaacat ttccgtgtcg cccttattcc cttttttgcg gcattttgcc   3540
ttcctgtttt tgctcaccca gaaacgctgg tgaaagtaaa agatgctgaa gatcagttgg   3600
gtgcacgagt gggttacatc gaactggatc tcaacagcgg taagatcctt gagagttttc   3660
gccccgaaga acgttttcca atgatgagca cttttaaagt tctgctatgt ggcgcggtat   3720
tatcccgtat tgacgccggg caagagcaac tcggtcgccg catacactat tctcagaatg   3780
acttggttga gtactcacca gtcacagaaa agcatcttac ggatggcatg acagtaagag   3840
aattatgcag tgctgccata accatgagtg ataacactgc ggccaactta cttctgacaa   3900
cgatcggagg accgaaggag ctaaccgctt ttttgcacaa catgggggat catgtaactc   3960
gccttgatcg ttgggaaccg gagctgaatg aagccatacc aaacgacgag cgtgacacca   4020
cgatgcctgt agcgatggca acaacgttgc gcaaactatt aactggcgaa ctacttactc   4080
tagcttcccg gcaacaatta atagactgga tggaggcgga taaagttgca ggaccacttc   4140
tgcgctcggc ccttccggct ggctggttta ttgctgataa atccggagcc ggtgagcgtg   4200
gttctcgcgg tatcatcgca gcgctggggc cagatggtaa gccctcccgt atcgtagtta   4260
tctacacgac ggggagtcag gcaactatgg atgaacgaaa tagacagatc gctgagatag   4320
gtgcctcact gattaagcat tggtaaaagc agagcattac gctgacttga cgggacggcg   4380
caagctcatg accaaaatcc cttaacgtga gttacgcgcg cgtcgttcca ctgagcgtca   4440
gaccccgtag                                                          4450
```

<210> SEQ ID NO 11

-continued

```
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(300)
<223> OTHER INFORMATION: This sequence may encompass 5-300 nucleotides,
      wherein some positions may be absent

<400> SEQUENCE: 11

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300


<210> SEQ ID NO 12
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(160)
<223> OTHER INFORMATION: This sequence may encompass 60-160 nucleotides,
      wherein some positions may be absent

<400> SEQUENCE: 12

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa                          160


<210> SEQ ID NO 13
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120
```